(12) United States Patent
Håkansson et al.

(10) Patent No.: US 9,796,777 B2
(45) Date of Patent: Oct. 24, 2017

(54) METHODS OF TREATING MALIGNANT TUMORS

(71) Applicant: Canimguide Therapeutics AB, Höllviken (SE)

(72) Inventors: Leif Håkansson, Höllviken (SE); Birgitta Clinchy, Ljungsbro (SE)

(73) Assignee: CANIMGUIDE THERAPEUTICS AB, Höllviken (SE)

( * ) Notice: Subject to any disclaimer, the term of this patent is extended or adjusted under 35 U.S.C. 154(b) by 0 days.

(21) Appl. No.: 14/815,471

(22) Filed: Jul. 31, 2015

(65) Prior Publication Data

US 2016/0046702 A1 Feb. 18, 2016

Related U.S. Application Data

(63) Continuation of application No. 12/599,484, filed as application No. PCT/SE2008/000314 on May 8, 2008, now Pat. No. 9,120,874.

(30) Foreign Application Priority Data

| May 8, 2007 | (SE) | 0701099 |
| May 8, 2007 | (SE) | 0701100 |
| Nov. 15, 2007 | (SE) | 0702520 |

(51) Int. Cl.
| *A61K 39/395* | (2006.01) |
| *C07K 16/18* | (2006.01) |
| *C07K 14/765* | (2006.01) |
| *G01N 33/50* | (2006.01) |
| *G01N 33/574* | (2006.01) |
| *A61K 38/00* | (2006.01) |
| *A61K 39/00* | (2006.01) |

(52) U.S. Cl.
CPC ............ *C07K 16/18* (2013.01); *C07K 14/765* (2013.01); *G01N 33/5044* (2013.01); *G01N 33/57484* (2013.01); *A61K 38/00* (2013.01); *A61K 2039/505* (2013.01); *C07K 2317/34* (2013.01); *G01N 2333/55* (2013.01); *G01N 2333/765* (2013.01); *G01N 2500/10* (2013.01)

(58) Field of Classification Search
None
See application file for complete search history.

(56) References Cited

U.S. PATENT DOCUMENTS

| 5,284,750 A | 2/1994 | Silvestrini et al. |
| 5,948,609 A | 9/1999 | Carter et al. |
| 6,737,057 B1 | 5/2004 | Zaghouani |
| 7,960,126 B2 | 6/2011 | Håkansson et al. |
| 8,133,688 B2 | 3/2012 | Håkansson et al. |
| 8,232,066 B2 | 7/2012 | Van Eyk et al. |
| 8,455,624 B2 | 6/2013 | Finan et al. |
| 8,771,969 B2 | 7/2014 | Van Eyk et al. |
| 9,120,874 B2 | 9/2015 | Høkansson et al. |
| 2003/0021792 A1 | 1/2003 | Roben et al. |
| 2005/0153329 A1 | 7/2005 | Høkansson et al. |
| 2009/0081649 A1 | 3/2009 | Høkansson et al. |
| 2010/0323370 A1 | 12/2010 | Høkansson et al. |
| 2011/0262470 A1 | 10/2011 | Høkansson et al. |
| 2011/0287969 A1 | 11/2011 | Høkansson et al. |
| 2014/0161812 A1 | 6/2014 | Håkansson et al. |

FOREIGN PATENT DOCUMENTS

| CA | 2 526 950 | 12/2003 |
| CN | 103694342 | 4/2014 |
| JP | 62-016430 | 1/1987 |
| JP | 2005089325 | 4/2005 |
| RU | 2360924 | 7/2009 |
| WO | WO 91/09619 | 7/1991 |
| WO | WO 00/28072 | 5/2000 |
| WO | WO 02/30465 | 4/2002 |
| WO | WO 03/099312 | 12/2003 |
| WO | WO 2004/048933 | 6/2004 |
| WO | WO 2004/082617 | 9/2004 |
| WO | WO 2004/082617 A2 | 9/2004 |
| WO | WO 2006/043891 | 4/2006 |
| WO | WO 2006/043891 A | 4/2006 |
| WO | WO 2006/068440 | 6/2006 |

(Continued)

OTHER PUBLICATIONS

Communication under Rule 71(3) in EP App No. 12164229.2 dated Apr. 21, 2016, appended with the amended claims filed Dec. 7, 2015 in EP App No. 12164229.2.
European Patent Office Communication dated Jul. 28, 2015 in European Patent Application No. 12 164 229.2, dated May 8, 2008.
Lindh Christian H et al: "Characterization of adducts formed between human serum albumin and the butadiene metabolite epoxybutanediol", Rapid Communications in Mass Spectrometry, vol. 19, No. 18, 2005, pp. 2488-2496.
Search Report and Search Opinion issued by European Patent Office in European Patent Application No. 12 164 229.2 dated Jul. 17, 2012.
Amendment to the claims of European Application No. 12 164 229.2, submitted on Feb. 25, 2013.
Rule 112(1) Communication in European Patent Application No. 12 164 229.2 dated Mar. 14, 2013.
Amendment and Response to Office Action in European Patent Application No. 12 164 229.2, submitted on May 3, 2013.
Office Action in European Patent Application No. 12 164 229.2 dated Oct. 25, 2013.

(Continued)

*Primary Examiner* — Dong Jiang
(74) *Attorney, Agent, or Firm* — Knobbe, Martens, Olson & Bear, LLP

(57) ABSTRACT

The present invention relates to isolated protein sequences that correspond to cell binding peptides, fragments, neo-structures and/or neo-epitopes of a normally occurring serum protein present in human tissue, wherein the peptide, fragment, neo-structure and/or neo-epitope has an immuno-regulatory activity and is the result of either an enhanced proteolytic activity and/or conformational changes in a tissue, or a malignant tumor. In the present patent application, a common structure of several of these peptides, fragments, neo-structures and/or neo-epitopes, having immunoregulatory activity by binding to receptors on immune cells, has been identified. The present invention further also relates to monoclonal and/or polyclonal antibodies directed to a cell binding fragment of a normally occurring serum protein present in human tissue, as described above.

5 Claims, 36 Drawing Sheets

(56) References Cited

FOREIGN PATENT DOCUMENTS

| WO | WO 2006/068440 A1 | 6/2006 |
|---|---|---|
| WO | WO 2006/110091 | 10/2006 |
| WO | WO 2008/136736 | 11/2008 |
| WO | WO 2015/035332 | 9/2013 |

OTHER PUBLICATIONS

Amendment and Response to Office Action for European Patent Application No. 12 164 229.2, submitted on May 5, 2014.
Office Action in European Patent Application No. 12 164 229.2 dated Jun. 2, 2014.
Amendment and Response to Office Action in European Patent Application No. 12 164 229.2, submitted on Oct. 9, 2014.
Office Action in European Patent Application No. 12 164 229.2 dated Dec. 23, 2014.
Response to Office Action for European Patent Application No. 12 164 229.2, submitted on Apr. 29, 2015.
Amendment and Declaration under Rule 37 C.F.R. 1.312 filed Jun. 15, 2015 in U.S. Appl. No. 14/096,878.
Office Action dated Oct. 13, 2016 in U.S. Appl. No. 14/096,878.
Office Action dated Mar. 16, 2016 in U.S. Appl. No. 14/096,878.
Office Action dated Sep. 10, 2015 in U.S. Appl. No. 14/096,878.
Extended European Search Report dated Jan. 18, 2017 in European Patent Application No. 16189090.0.
Anderson et al., "Contributions of the Mac-1 Glycoprotein Family to Adherence-Dependent Granulocyte Functions: Structure-Function Assessments Employing Subunit-Specific Monoclonal Antibodies" The Journal of Immunology, Jul. 1, 1986, pp. 15-27, vol. 137 No. 1.
Bajpai et al., "Immunomodulating Activity of Analogs of Noninflammatory Fragment 163-171 of Human Interleukin-1 B", Immunopathology, 1998, 38:237-245.
Belluco et al., "Interleukin-6 Blood Level Is Associate With Circulating Carcinoembryonic Antigen and Prognosis in Patients With Colorectal Cancer" Annals of Surgical Oncology, 2000, pp. 133-138, vol. 7, No. 1.
Bhol et al., "The autoantibodies to alpha 6 beta 4 integrin of patients affected by ocular cicatricial pemphigoid recognize predominantly epitopes within the large cytoplasmic domain of human beta 4." J. Immunol. Sep. 1, 2000;165(5):2824-9.
Brevig et al., "The recognition of adsorbed and denatured proteins of different topographies by beta2 integrins and effects on leukocyte adhesion and activation." Bismaterials. Jun. 2005;26(16):3039-53.
Brooks et al., "Radioimmunoassay of Laminin in Serum and its Application to Cancer Patients", Clinical Chemistry, 1986, 32/5: 787-791.
Chung et al., "Serum Interleukin-6 Levels Reflect the Disease Status of Colorectal Cancer" Journal of Curgical Oncology, 2003, pp. 222-226, vol. 83.
Cioli et al., "A New Protein Antidenaturant Agent, Bindarit, Reduces Secondary Phase of Adjuvant Arthritis in Rats", Journal of Rheumatology 1992 vol. 19, No. 11 pp. 1735-1742.
Clinchy et al., "Preoperatvie interleukin-6 production by mononuclear blood cells predicts survival after radical surgery for colorectal carcinoma." Cancer. May 1, 2007;109(9):1742-9.
Davis et al., "The α4β1 integrin can mediate leukocyte adhesion to casein and denatured protein substrates" Journal of Leukocyte Biology, 1997, pp. 318-328, vol. 62.
Davis, George E., "The Mac-1 and p150, 95 β2 Integrins Bind Denatured Proteins to Mediate Leukocyte Cell-Substrate Adhesion" Experimental Cell Research, 1992, pp. 242-252, vol. 200.
Drachenberg et al., "Circulating Levels of interleukin-6 in Patients with Hormone Refractory Prostate Cancer", The Prostate, 41:127-133 (1999). (Abstract).
Evans, Rachel et al,, "Integrins in immunity" Journal of Cell Science, 2009, pp. 215-225, vol. 122.
Falconer, J. Stuart et al., "Acute-Phase Protein Response and Survival Duration of Patients with Pancreatic Cancer" Cancer, Apr. 15, 1995, pp. 2077-2082, vol. 75, No. 8.

File History of U.S. Appl. No. 12/599,484, filed Nov. 9, 2009.
Galizia et al., "Prognostic Significance of Circulating IL-10 and IL-6 Serum Levels in Colon Cancer Patients Undergoing Surgery" Clinical Immunology, Feb. 2002, pp. 169-178, vol. 102, No. 2.
Gruel et al., "Bypassing tumor-specific and bispecific antiboides: triggering of antitumor immunity by expression of anti-FcγR scFv on cancer cell surface" Gene Therapy (2001) 8: 1721-1728.
Håkansson, A. et al., "Biochemotherapy of metastatic malignant melanoma. Predictive value of tumor-infiltrating lymphocytes" British Journal of Cancer, 2001, pp. 1871-1877, vol. 85, No. 12.
Håkansson, A. et al., "Tumor-infiltrating lymphocytes in metastatic malignant melanoma and response to interferon alpha treatment" British Journal of Cancer, 1996, pp. 670-676, vol. 74.
Hallström et al., S-Nitroso Human Serum Albumin Treatment Reduces Ischemia/Reperfusion Injury in Skeletal Muscle via Nitric Oxide Release. Circulation 2002, vol. 105, pp. 3032-3038.
Hauptman et al., "A Monoclonal IgM Protein with Antibody-like Activity for Human Albumin", The Journal of Clinical Investigation, vol. 53, Mar. 1974, pp. 932-940.
Hauptman et al., "Antibodies to human albumin in cirrhotic sera." J. Clin Invest. Jul. 1974;54(1):122-7.
International Preliminary Report on Patentability, dated Dec. 4, 2006, issued in PCT/SE06/000440.
International Search Report, dated Nov. 4, 2003, issued in PCT/SE03/00869.
International Search Report, dated Feb. 6, 2006, issued in PCT/SE05/001582.
International Search Report, dated Jul. 13, 2006, issued in PCT/SE06/000440.
International Search Report, dated Jan. 5, 2009, issued in PCT/SE08/000314.
Kaminska et al., "Clinical Significance of Serum Cytokine Measurements in Untreated Colorectal Cancer Patients: Soluble Tumor Necrosis Factor Receptor Type I—An Independent Prognostic Factor" Tumor Biology, 2005, pp. 186-194, vol. 26.
Kaminska et al., "CRP, TNF☐, IL-1ra, IL-6, IL-8 and IL-10 in Blood Serum of Colorectal Cancer Patients" Pathology Oncology Research, 2000, pp. 38-41, vol. 6, No. 1.
Kinoshita et al., "Serum Interleukin-6 Level Reflects the Tumor Proliferative Activity in Patients with Colorectal Carcinoma" Cancer, Jun. 15, 2009, pp. 2526-2531, vol. 85, No. 12.
Koch et al., "High dose human serum albumin for the treatment of acute ischemic stroke: a safety study" Neurocrit Care, 2004, 1(3):335-41.
Kuntz "Structure-based strategies for drug design and discovery." Science. 1992 257(5073):1078-1082.
Maccio et al., "High Serum Levels of Soluble IL-2 Receptor, Cytokines, and C Reactive Protein Correlate with Impairment of T Cell Response in Patients with Advanced Epithelial Ovarian Cancer", Gynecological Oncology, 1998, 69: 248-252.
Miller et al., "Ligand binding to proteins: the binding landscape model." Protein Sci, Oct. 1997;6(10):2166-79.
Neuwelt, M.D., Edward A. "Permeability of human brain tumor to 99mTc-gluco-heptonate and 99mTc-albumin" J Neurosurg, 1986, pp. 194-198, vol. 65.
Nikiteas et al., "Serum IL-6, TNF☐ and CRP levels in Greek colorectal cancer patients: Prognostic implications" World Journal of Gastroenterology, 2005, pp. 1639-1643, vol. 11.
Oyama, et al., "Autoantibodies to extracellular matrix protein 1 in lichen sclerosus." Lancet. Jul. 12, 2003;362(9378):118-23.
Piancatelli et al., "Local Expression of Cytokines in Human Colorectal Carcinoma: Evidence of Specific Interleukin-6 Gene Expression", Journal of Immunotherapy, 1999, vol. 22, p. 25-32.
Rich et al., "Elevated Serum Cytokines Correlated with Altered Behavior, Serum Cortisol Rhythm, and Dampened 24-Hour Rest-Activity Patterns in Patients with Metastatic Colorectal Cancer" Clinical Cancer Research, Mar. 1, 2005, pp. 1757-1764, vol. 11.
Rouard et al, "Fc Receptors as Targets for Immunotherapy" Intern. Rev. Immunol. (1997) 16: 147-185.
Ruka et al., "Alterations of routine blood tests in adult patients with soft tissue sarcomas: Relationships to cytokine serum levels and prognostic significance" Annals of Oncology (2001) 12: 1423-1432.

(56) References Cited

OTHER PUBLICATIONS

Saso et al., "Inhibition of Protein Denaturation by Fatty Acits, Bile Salts and Other Natural Substances: A New Hypothesis for the Mechanism of Action of Fish Oil in Rheumatic Diseases" Japan Journal of Pharmacology, 1999, vol. 79 pp. 89-99.

Shacter, E. et al. "Stimuation of interleukin-6 and prostaglandin E2 secretion from peritoneal macrophages by polymers of albumin", Blood, 82:2853-2864 (1993). 13 pages.

Shinoda et al., "immunopathological role of pulpal tissue components in periapical pathosis. I. Detection of "new" antigens in modified dog pulpal extracts", Journal of Endodontics, 12 (11):528-533, 1986.

Siedlar et al., "Depressed Tumor Necrosis Factor Alpha and Interleukin-12p40 Production by Peripheral Blood Mononuclear Cells of Gastric Cancer Patients: Associate with IL-IR-Associated Kinase-1 Protein Expression and Disease State", Internation Journal Cancer, 2005, vol. 114, p. 144-152.

Tamura et al., "Anti-albumin antibodies in sera of patients with liver disease." Gastroenterol Jpn. Oct. 1982;17(5):469-75.

Tockman et al., "Considerations in Bringing a Cancer Biomarker to Clinical Application", Cancer Research, 1992, 52:2711s-2718s.

Ueda et al., "Serum levels of cytokines in patients with colorectal cancer: Possible involvement of interleukin-6 and interleukin-8 in hematogenous metastasis" J. Gastroenterol. (1994) 29: 423-429.

Wood et al., "The Clinical Significance of the Pattern of Elevated Serum Carcinoembryonic Antigen (CEA) Levels in Recurrent Colorectal Cancer", Br. J. Surg., 1980, 67(1): 46-48 (Abstract).

Wu et al., "Serum Interleukin-6 Levels Reflect Disease Status of Gastric Cancer", American Journal of Gastroenterology, 1996, 91(7): 1417-1422 (Abstract).

Tamura et al. Structural Correlates of an Anticarcinoma Antibody: Identification of Specificity-Determining Residues (SDRs) and Development of a Minimally Immunogenic Antibody Variant by Retention of SDRs Only. J. Immunol. 2000, 164: pp. 1432-1441.

Vaswami et al. "Humanized antibodies as potential therapeutic drugs." Ann. Allergy Asthma Immunol. 1998, 81: 105-119.

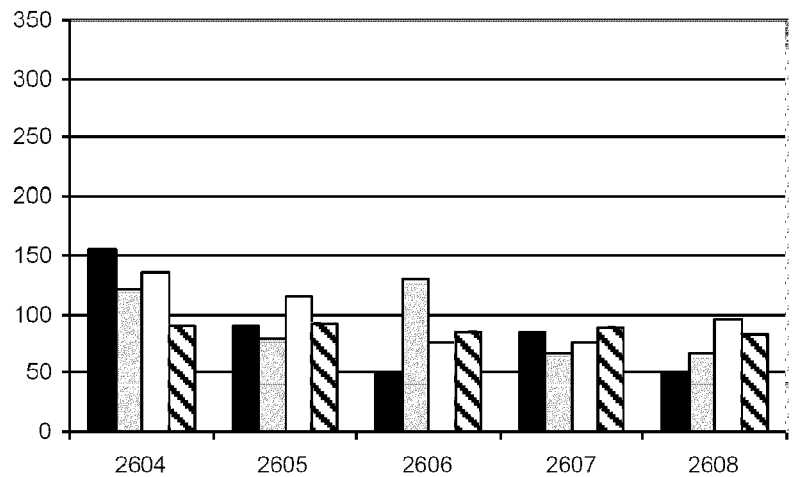
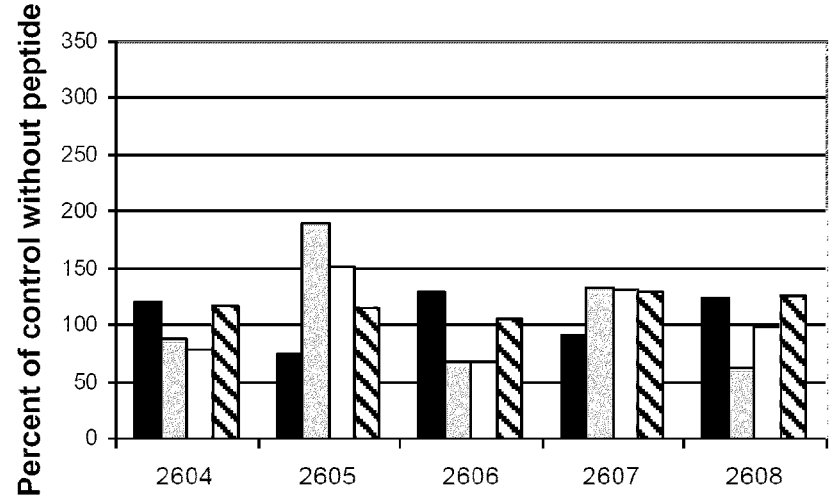
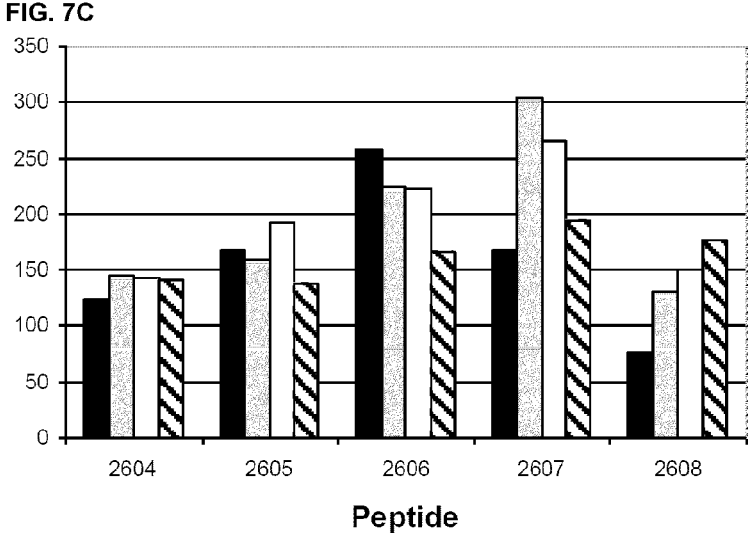
FIG. 7A
FIG. 7B
FIG. 7C

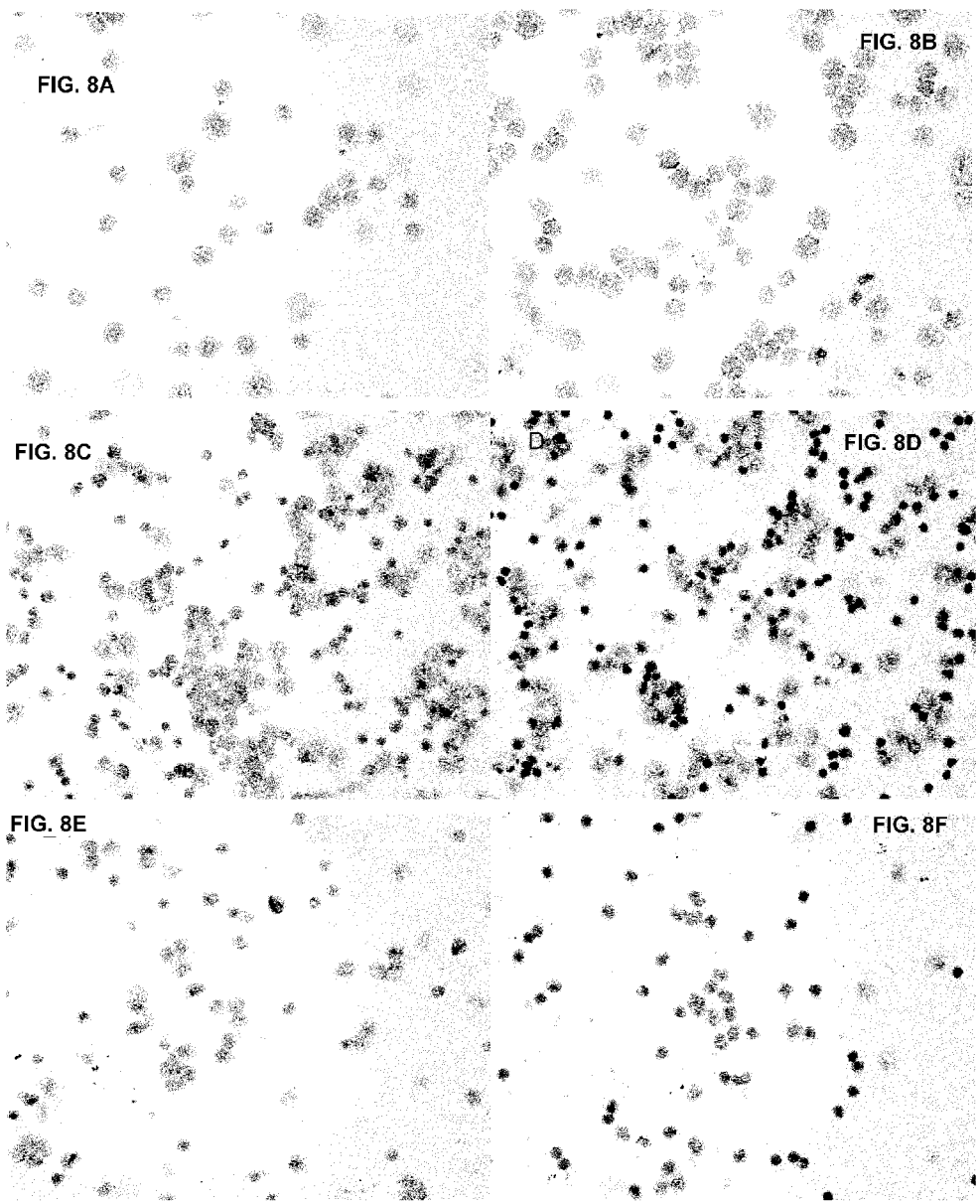

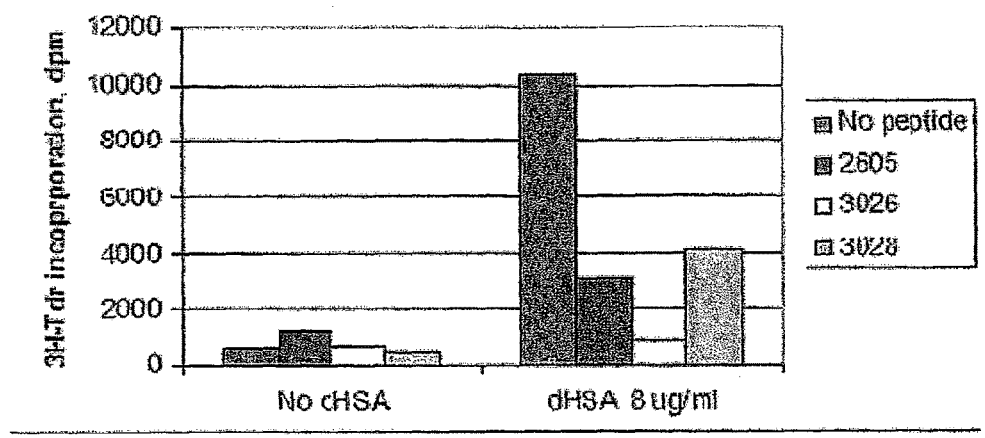
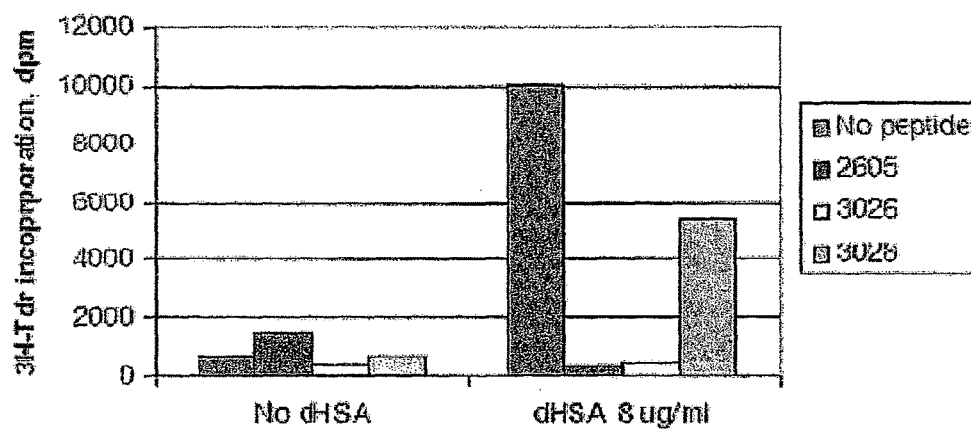
fig.9

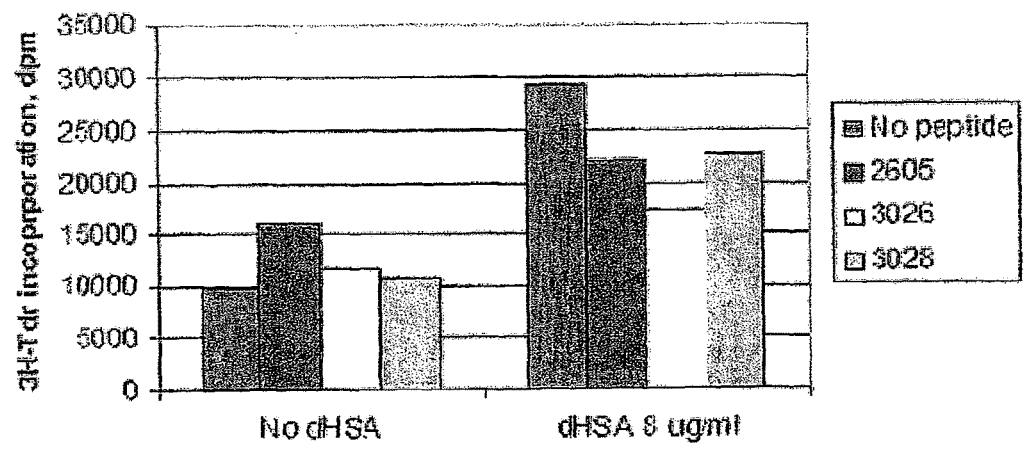
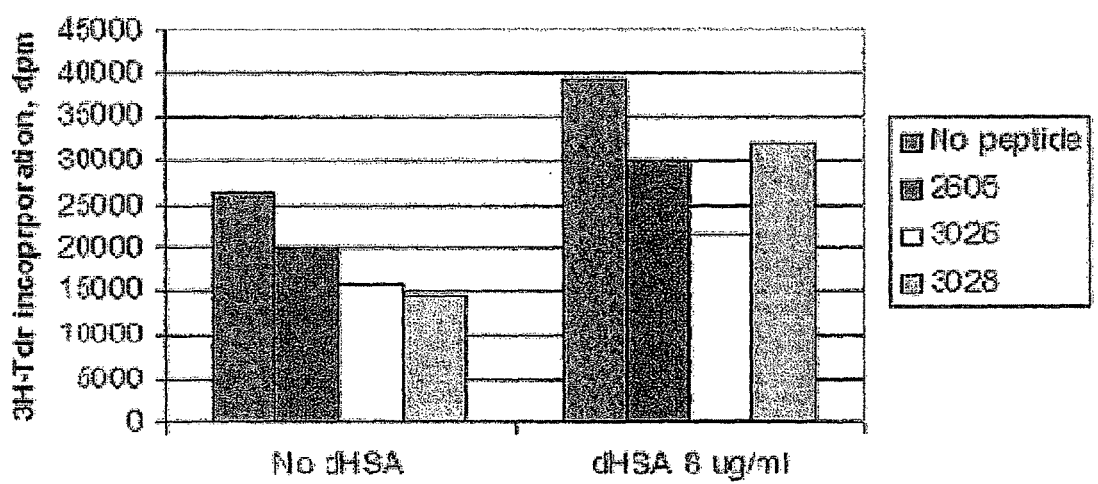
fig.9 continued

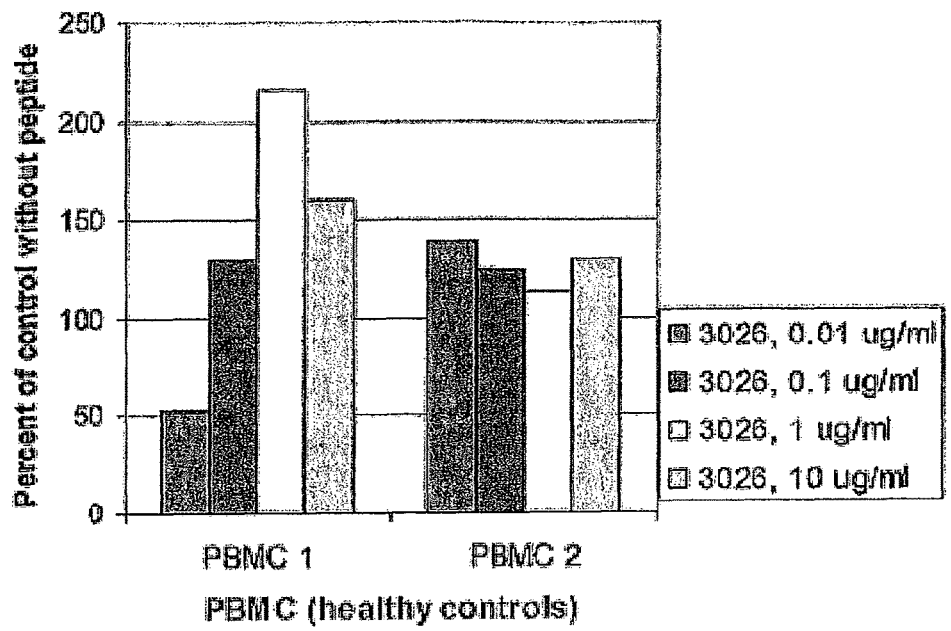
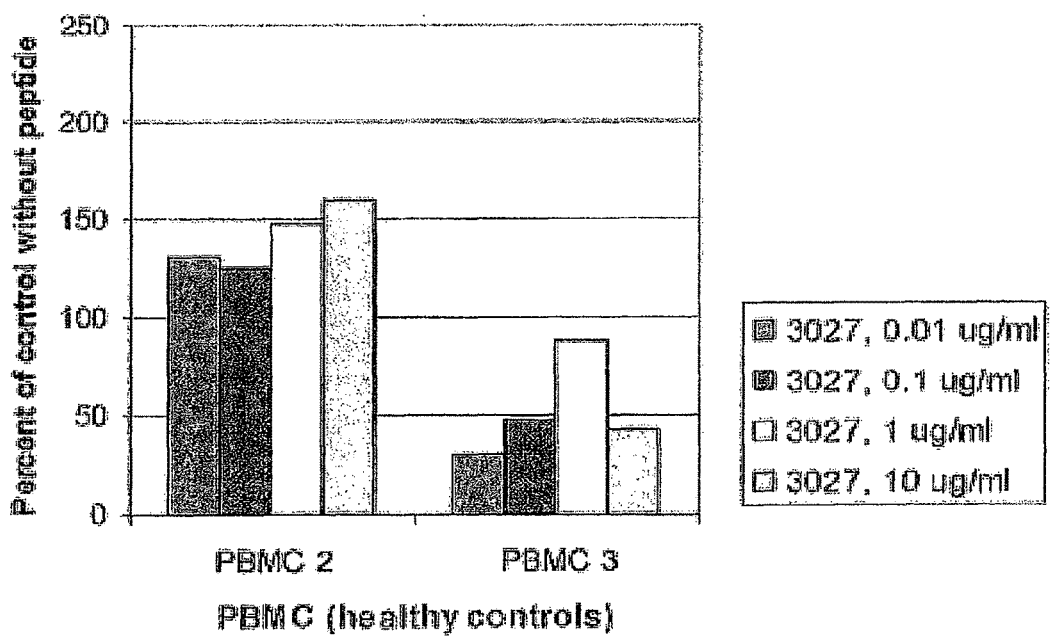
fig. 11

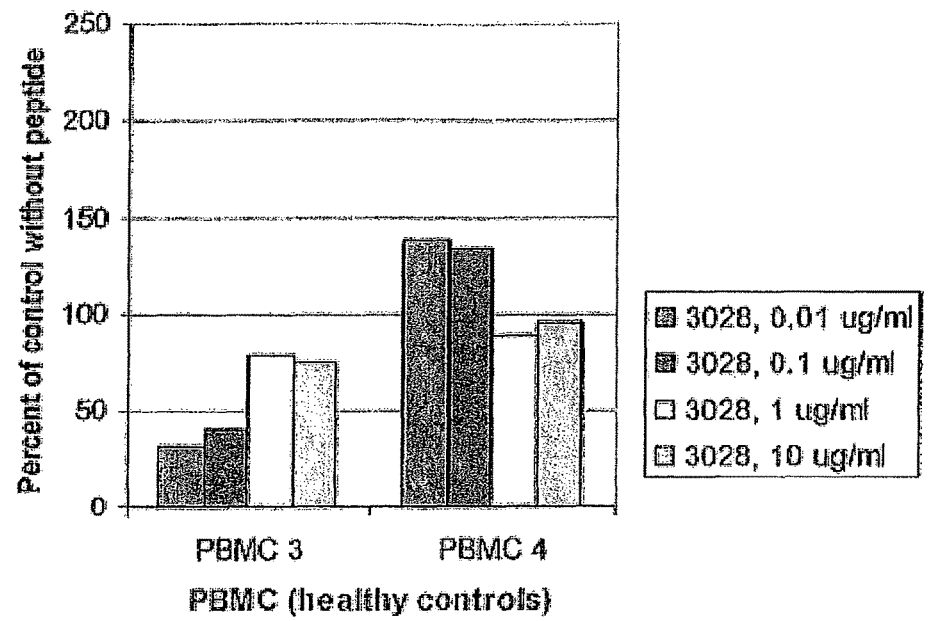
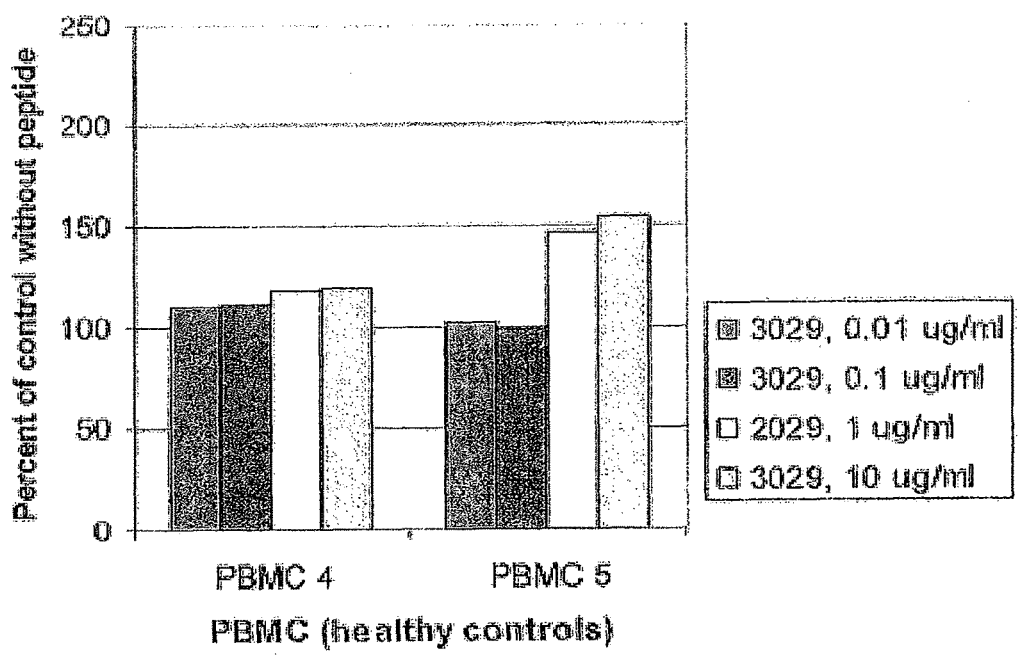
fig.11 continued

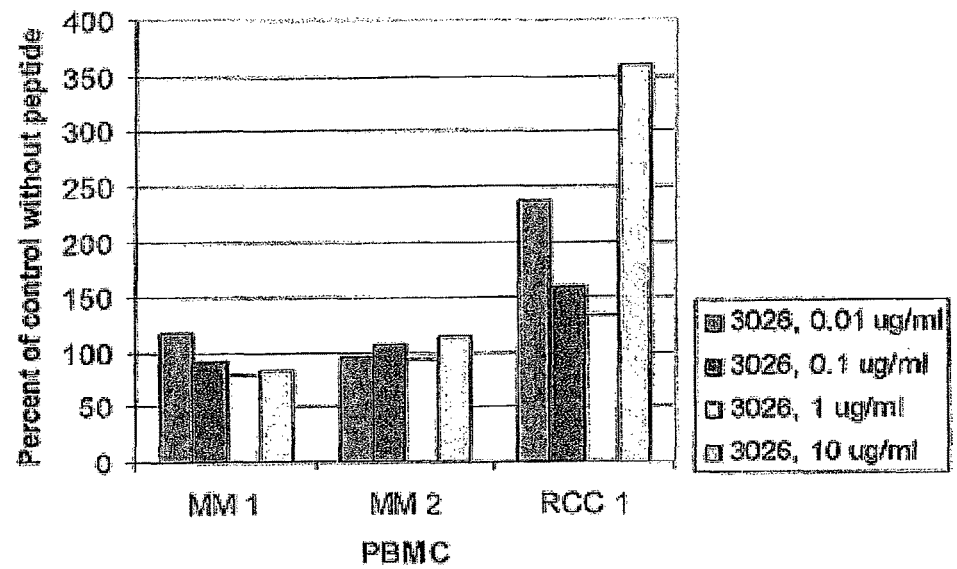
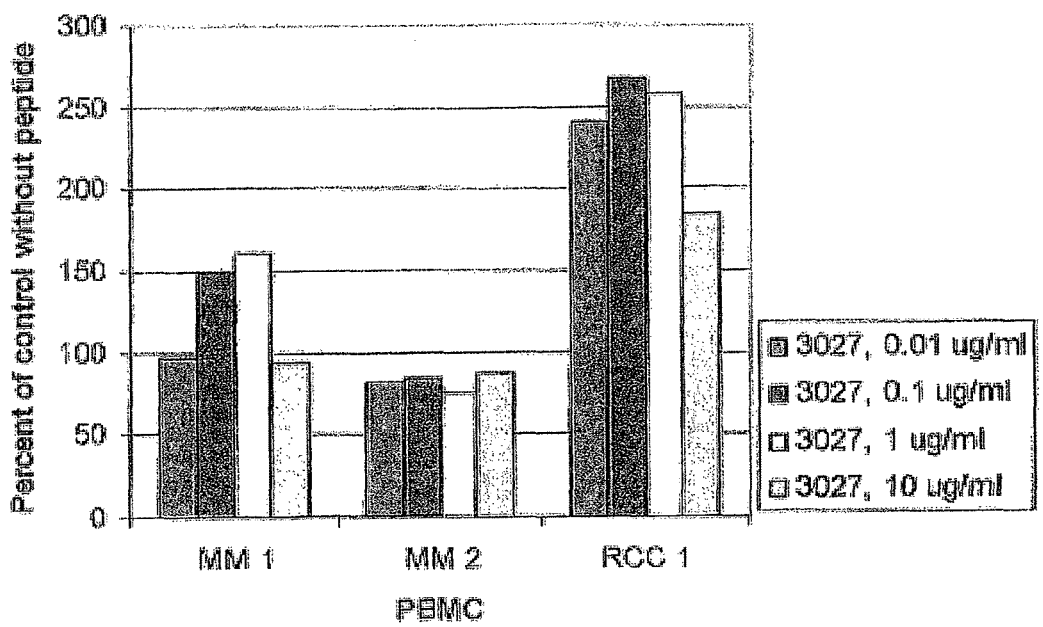
Fig. 12

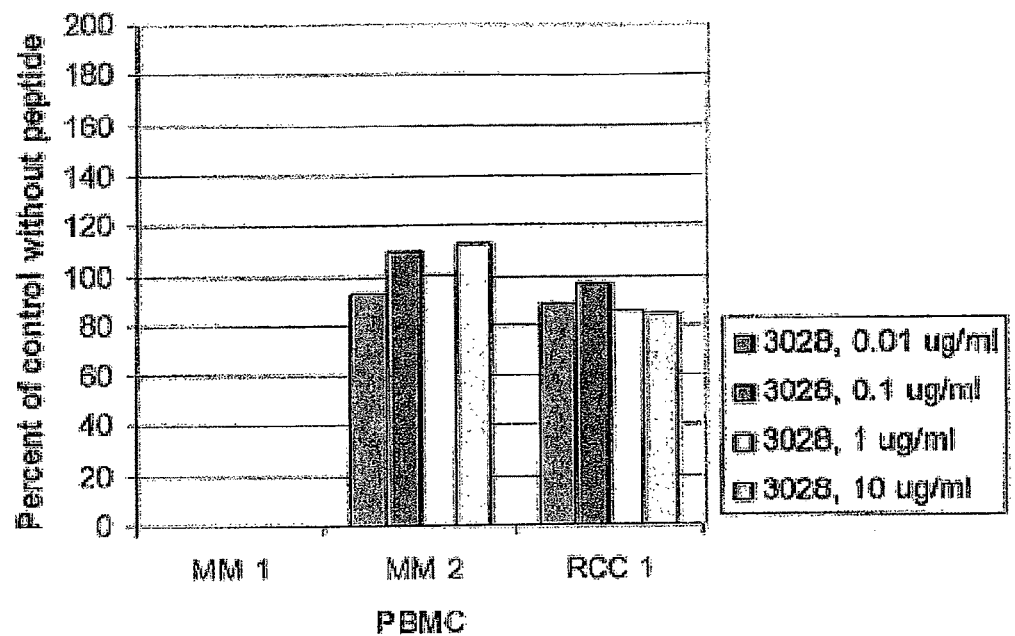
Effect of 3028 on LPS-induced IL-6 production
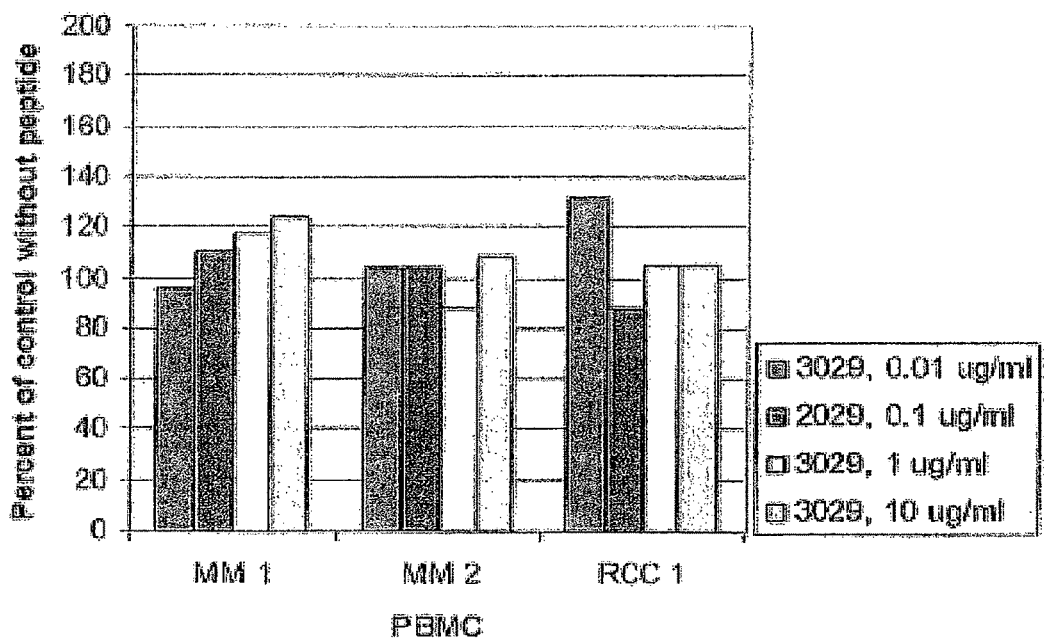
Effect of 3029 on LPS-induced IL-6 production
fig.12 continued

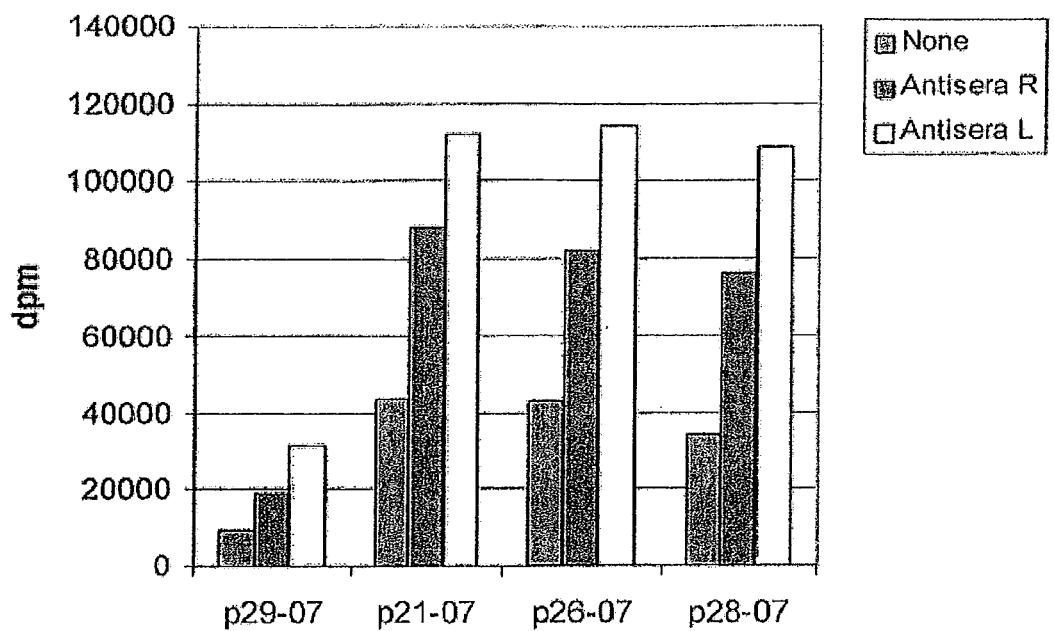
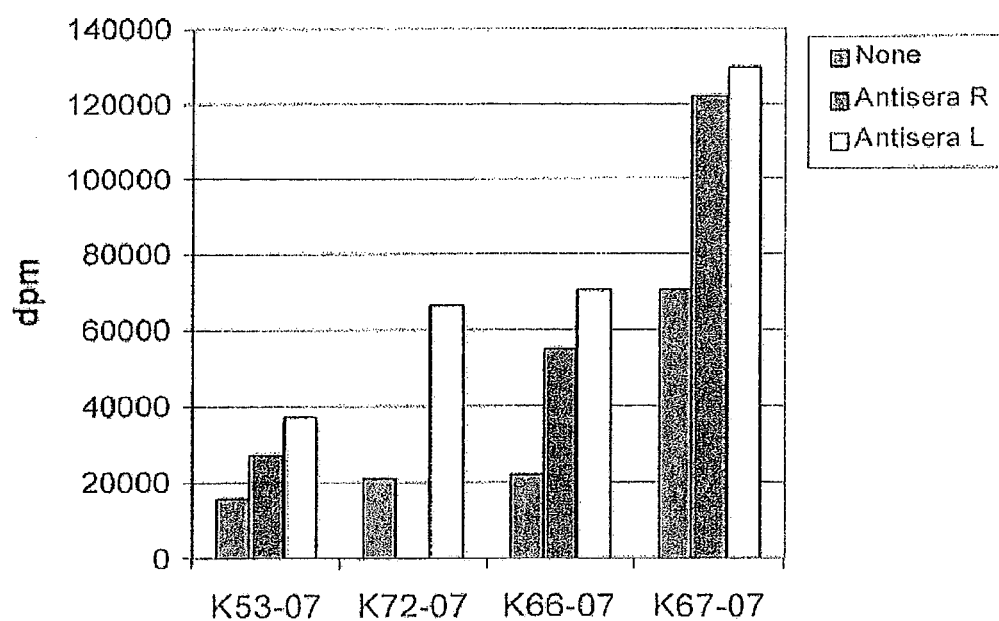
fig.22

3028 (SEQ ID NO:164)

PHECYAK

| 3325 | 3218 |
|---|---|
| VFDEFKPLVE (SEQ ID NO:81) | EPQNLIK (SEQ ID NO:172) *QNCELFEQ* |
| Some antiproliferative activity | Some antiproliferative activity |
| Weak binding to LFA-1 | Weak binding to LFA-1 |
| Binds to affinity purified antibodies | Does not bind to affinity purified antibodies |

Figure 26

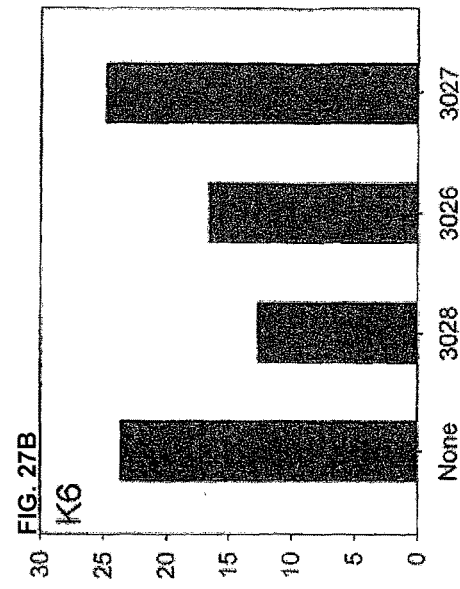
FIG. 27B K6
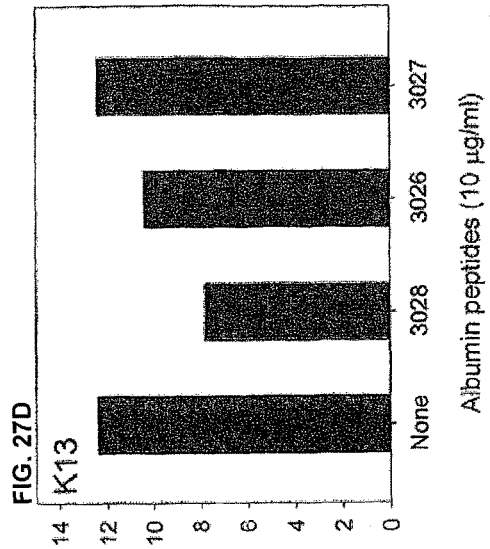
FIG. 27D K13
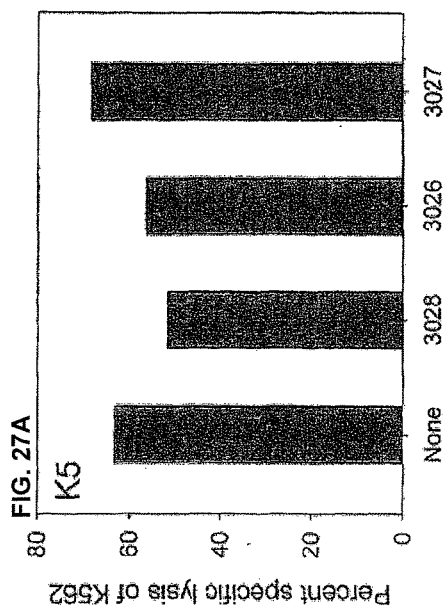
FIG. 27A K5
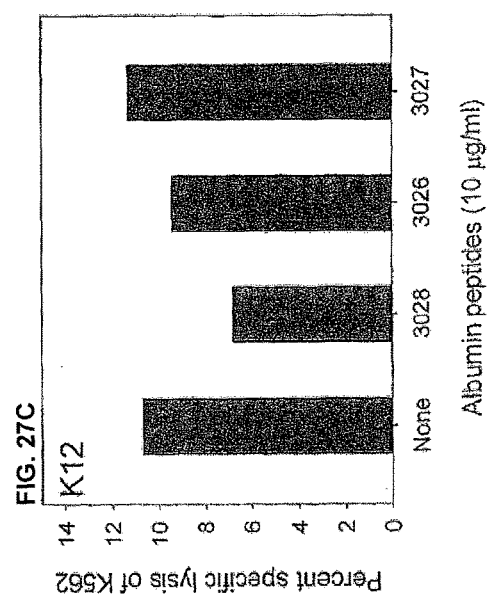
FIG. 27C K12

Figure 28

Table 4A. E3-7K sequences in HSA

| E7K sequence | | E4K sequence | | E5K sequence | | E6K sequence | | E7K sequence | |
|---|---|---|---|---|---|---|---|---|---|
| Sequence start | Sequence | Sequence start | Sequence | Sequence start | Sequence | Sequence start | Sequence | Sequence start | Sequence |
| 040 | EENFK (SEQ ID NO:1) | 155 | EETFLK (SEQ ID NO:11) | 030 | EVAHRFK (SEQ ID NO:17) | 081 | ESAENCDK (SEQ ID NO:29) | 290 | ENQDSISSK (SEQ ID NO:37) |
| 061 | EDHVK (SEQ ID NO:2) | 156 | ETFLKK (SEQ ID NO:12) | 068 | EVTEFAK (SEQ ID NO:18) | 110 | EMADCCAK (SEQ ID NO:30) | 580 | EKCCKADDK (SEQ ID NO:38) |
| 084 | ENCDK (SEQ ID NO:3) | 378 | ETLLEK (SEQ ID NO:13) | 124 | ECFLQHK (SEQ ID NO:19) | 191 | ECCQAADK (SEQ ID NO:31) | 589 | ETCFAEEGK (SEQ ID NO:39) |
| 156 | ETFLK (SEQ ID NO:4) | 519 | ETYVPK (SEQ ID NO:14) | 155 | EETFLKK (SEQ ID NO:20) | 212 | EGKASSAK (SEQ ID NO:32) | | |
| 232 | ERAFK (SEQ ID NO:5) | 544 | ERQIKK (SEQ ID NO:15) | 177 | ELLFFAK (SEQ ID NO:21) | 406 | EEPQNLIK (SEQ ID NO:33) | | |
| 301 | ECCEK (SEQ ID NO:6) | 555 | ELVKHK (SEQ ID NO:16) | 208 | ELRDEGK (SEQ ID NO:22) | 449 | EVSRNLGK (SEQ ID NO:34) | | |
| 391 | ECYAK (SEQ ID NO:7) | | | 251 | EFAEVSK (SEQ ID NO:23) | 542 | EKERQIKK (SEQ ID NO:35) | | |
| 544 | ERQIK (SEQ ID NO:8) | | | 304 | EKPLLEK (SEQ ID NO:24) | 555 | ELVKHKPK (SEQ ID NO:36) | | |

Figure 28 continued

| E3K sequence | | E4K sequence | | E5K sequence | | E6K sequence | | E7K sequence | |
|---|---|---|---|---|---|---|---|---|---|
| Sequence start | Sequence | Sequence start | Sequence | Sequence start | Sequence | Sequence start | Sequence | Sequence start | Sequence |
| 580 | EKCCK (SEQ ID NO:9) | | | 335 | ESKDVCK (SEQ ID NO:25) | | | | |
| 594 | EEGKK (SEQ ID NO:10) | | | 407 | EPQNLIK (SEQ ID NO:26) | | | | |
| | | | | 420 | EQLGEYK (SEQ ID NO:27) | | | | |
| | | | | 542 | EKERQIK (SEQ ID NO:28) | | | | |

Figure 29

Table 4B. K3-7E sequences in HSA

| K3E sequence | | K4E sequence | | K5E sequence | | K6E sequence | | K7E sequence | |
|---|---|---|---|---|---|---|---|---|---|
| Sequence start | Sequence | Sequence start | Sequence | Sequence start | Sequence | Sequence start | Sequence | Sequence start | Sequence |
| 036 | KDLGE (SEQ ID NO:40) | 036 | KDLGEE (SEQ ID NO:54) | 075 | KTCVADE (SEQ ID NO:61) | 065 | KLVNEVTE (SEQ ID NO:69) | 183 | KRYKAAFTE (SEQ ID NO:76) |
| 065 | KLVNE (SEQ ID NO:41) | 160 | KKYLYE (SEQ ID NO:55) | 298 | KLKECCE (SEQ ID NO:62) | 117 | KQEPERNE (SEQ ID NO:70) | 337 | KDVCKNYAE (SEQ ID NO:77) |
| 117 | KQEPE (SEQ ID NO:42) | 186 | KAAFTE (SEQ ID NO:56) | 310 | KSHCIAE (SEQ ID NO:63) | 205 | KLDELRDE (SEQ ID NO:71) | 558 | KHKPKATKE (SEQ ID NO:78) |
| 161 | KYLYE (SEQ ID NO:43) | 249 | KAEFAE (SEQ ID NO:57) | 460 | KCCKHPE (SEQ ID NO:64) | 375 | KTYETTLE (SEQ ID NO:72) | 581 | EKDDAKCCK (SEQ ID NO:79) |
| 264 | KVHTE (SEQ ID NO:44) | 402 | KPLVEE (SEQ ID NO:58) | 468 | KRMPCAE (SEQ ID NO:65) | 412 | KQNCELFE (SEQ ID NO:73) | | |
| 286 | KYICE (SEQ ID NO:45) | 523 | KEFNAE (SEQ ID NO:59) | 549 | KQTALVE (SEQ ID NO:66) | 548 | KKQTALVE (SEQ ID NO:74) | | |
| 300 | KECCE (SEQ ID NO:46) | 584 | KADDKE (SEQ ID NO:60) | 560 | KPKATKE (SEQ ID NO:67) | 588 | KETCFAEE (SEQ ID NO:75) | | |
| 305 | KPLLE (SEQ ID NO:47) | | | 588 | KETCFAE (SEQ ID NO:68) | | | | |

Figure 29 continued

| K3E sequence | | K4E sequence | | K5E sequence | | K6E sequence | | K7E sequence | |
|---|---|---|---|---|---|---|---|---|---|
| Sequence start | Sequence | Sequence start | Sequence | Sequence start | Sequence | Sequence start | Sequence | Sequence start | Sequence |
| 341 | KNYAE (SEQ ID NO:48) | | | | | | | | |
| 396 | KVFDE (SEQ ID NO:49) | | | | | | | | |
| 402 | KPLVE (SEQ ID NO:50) | | | | | | | | |
| 413 | KQNCE (SEQ ID NO:51) | | | | | | | | |
| 499 | KCCTE (SEQ ID NO:52) | | | | | | | | |
| 562 | KATKE (SEQ ID NO:53) | | | | | | | | |

METHODS OF TREATING MALIGNANT TUMORS

The present Application is a continuation of U.S. patent application Ser. No. 12/599,484 filed Nov. 9, 2009, now U.S. Pat. No. 9,120,874 issued Sep. 1, 2015, which is the US National Phase of PCT Application No. PCT/SE2008/000314 filed May 8, 2008, which claims the benefit of Swedish Patent Application No. 0701099-4 filed May 8, 2007, Swedish Patent Application No. 0701100-0 filed May 8, 2007, and Swedish Patent Application No. 0702520-8 filed Nov. 15, 2007, each of which is hereby incorporated by reference in its entirety. The present Application is accompanied by an electronic sequence listing entitled CANIG004C1.TXT, created Jun. 9, 2015, last modified Aug. 3, 2015 which is 34,570 bytes in size.

TECHNICAL FIELD

The present invention relates to certain identified protein sequences having an immunoregulatory effect, as well as antibodies directed to such protein sequences and to methods for identifying such.

BACKGROUND OF THE INVENTION

Although data indicate that the immune system is of major importance for cancer control, malignant tumours continue to grow and the efficacy of immunotherapy is rather poor with an objective remission rate of 15-30%. There can be several reasons for this apparent paradox:
  Tumours avoid the recognition by the immune system by not expressing tumour associated antigens properly
  Tumour associated antigens (often self antigens), which are too weak to elicit an adequate immune response
  Induction of tolerance
  Cancer related immunosuppression, which prevents an adequate immune response These alternatives require completely different therapeutic strategies, either proper stimulation of the immune system or control of cancer related immunosuppressor mechanisms.

Immunosuppression in cancer is mainly characterized by: Reduced proliferative and cytotoxic capacity of lymphocytes, in particular tumour infiltrating lymphocytes, poor migration of inflammatory cells, reduced production and response to IL-2, difficulties to elicit an immune response by vaccination, also against other than tumour related antigens and pathological cytokine production. This dysregulation of the immune system results in poor immune mediated cancer control and a paraneoplastic syndrome (subfebrility, fatigue, anorexia, weight loss and deterioration of laboratory parameters).

Immunostimulatory therapeutic strategies using cytokines (e.g. interferons, interleukins) or vaccination, in order to enhance the immune mediated reactivity to the tumour, has been tried for several decades, but have so far had only very limited success. This indicates that immunostimulation in order to overcome a poor immune response in cancer patients might be suppressed by other so far unidentified mechanisms.

We have in two previous patent applications described two fundamental immunoregulatory mechanisms of relevance to all types of malignant tumours. In the first of these applications the importance of Fc-receptor modulation and ways to overcome this cancer related immunosuppression by modulating Fc-receptor cross-linking was demonstrated. In this patent application also proteolytic fragments of normally occurring proteins were demonstrated to induce pathological monokine production. In the second patent application some of these neo-structures were found to be integrin binding/blocking and their occurrence and immunoregulatory activity was further analysed by using monoclonal antibodies directed against albumin derived neo-structures. In the latter patent application also the occurrence and importance of auto-antibodies to these neo-structures is described.

SUMMARY OF THE PRESENT INVENTION

In the present patent application, several protein sequences, such as peptides, peptide fragments, neo-structures and/or neo-epitopes, of a protein normally occurring in serum, which are binding to immune cells are disclosed. Some of their immunoregulatory activities are described.

What is more, in the present patent application, the structure of several of these peptides, peptide fragments, neo-structures and/or neo-epitopes, having immunoregulatory activity by binding to receptors on immune cells, have been identified.

DETAILED DESCRIPTION OF THE PRESENT INVENTION

The present invention relates to an immune cell binding protein sequence of a protein normally occurring in serum, such as to an isolated cell binding peptide, peptide fragment, neo-structure and/or neo-epitope of a protein normally occurring in serum, which is present in a human tissue, wherein said peptide, peptide fragment, neo-structure and/or neo-epitope has an immunoregulatory activity and said peptide, peptide fragment, neo-structure and/or neo-epitope is the result of an enhanced proteolytic activity and/or denaturing in an inflammatory tissue and/or a malignant tumour. Specific examples of such immune cell binding protein sequences are selected from the amino acid sequences listed e.g. as SEQ.ID.NO(s). 1-81, such as in particular from the sequences corresponding to SEQ.ID.NO(s). 26, 80, and 81.

Consequently, the present invention also relates to the use as a medicine of an immune cell binding protein sequence of a protein normally occurring in serum, such as an isolated cell binding peptide, peptide fragment, neo-structure and/or neo-epitope, which is present in a human tissue, wherein said peptide, peptide fragment, neo-structure and/or neo-epitope has an immunoregulatory activity and said peptide, peptide fragment, neo-structure and/or neo-epitope is the result of an enhanced proteolytic activity and/or denaturing in an inflammatory tissue and/or a malignant tumour, selected from the amino acid sequences listed as SEQ.ID.NO(s). 1-81, such as in particular selected from the sequences corresponding to SEQ.ID.NO(s). 26, 80, and 81.

In particular, the present invention relates to the use of an immune cell binding protein sequence of a protein normally occurring in serum, according to the present invention, selected from the amino acid sequences listed as SEQ.ID.NO(s). 1-81, such as in particular selected from the sequences corresponding to SEQ.ID.NO(s). 26, 80, and 81, for diagnosing, treating and/or preventing cancer in a patient in need thereof.

A preferred embodiment thereof is a monoclonal antibody directed to an immune cell binding protein sequence of a protein normally occurring in serum, such as an isolated cell binding peptide, peptide fragment, neo-structure and/or neo-epitope, which is present in a human tissue, wherein said peptide, peptide fragment, neo-structure and/or neo-epitope has an immunoregulatory activity and said peptide, peptide fragment, neo-structure and/or neo-epitope is the result of an enhanced proteolytic activity and/or denaturing in an inflammatory tissue and/or a malignant tumour. In a presently preferred embodiment, such a monoclonal antibody is directed against at least one of the protein sequences corresponding to a sequence selected from the amino acid sequences listed as SEQ.ID.NO(s). 1-81, such as in particular selected from the sequences corresponding to SEQ.ID. NO(s). 26, 80, and 81.

Another, equally preferred embodiment of the present invention is a polyclonal rabbit anti-3028 antibody, which is herein demonstrated, as well as a polyclonal rabbit anti-3218 or anti-3315 antibody, i.e. a polyclonal rabbit antibody that is directed against at least one of the protein sequences corresponding to SEQ.ID.NO(s). 26, 80 or 81. Such an antibody is typically used for different diagnose and/or research methods.

A further aspect of the invention relates to a method for diagnosing the presence of a malignant tumour by determining the response to an antibody as described above.

A still further aspect of the invention relates to a compound inhibiting the activity of an immune cell binding protein sequence of a protein normally occurring in serum, such as an isolated cell binding peptide, peptide fragment, neo-structure and/or neo-epitope, which is present in a human tissue, wherein said peptide, peptide fragment, neo-structure and/or neo-epitope has an immunoregulatory activity and said peptide, peptide fragment, neo-structure and/or neo-epitope is the result of an enhanced proteolytic activity and/or denaturing in an inflammatory tissue and/or a malignant tumour.

A further aspect of the invention relates to a method for treating any malignant tumour by administering a compound inhibiting the occurrence of an immune cell binding protein sequence of a protein normally occurring in serum, such as an isolated cell binding peptide, peptide fragment, neo-structure and/or neo-epitope, according to the present invention, which said peptide, peptide fragment, neo-structure and/or neo-epitope has an immunoregulatory activity and is the result of a cancer or malign tumour.

A preferred embodiment of the method consists in that an antibody raised against said cell binding peptide, peptide fragment, neo-structure and/or neo-epitope is administered in an amount sufficient to raise an immune response to any malignant tumour.

A further aspect of the invention relates to a method for treating a malignant tumour by inhibiting the activity of said immunoregulatory peptide, peptide fragment, neo-structure and/or neo-epitope by using standard drug developing pharmacological principles producing receptor blocking drugs or drugs inhibiting signal transduction from the receptors of said peptide, peptide fragment, neo-structure and/or neo-epitope.

In particular again, the present invention for the first time discloses that an immune cell binding protein sequence of a protein normally occurring in serum, according to the present invention, such as an isolated cell binding peptide, peptide fragment, neo-structure and/or neo-epitope, being the result of an enhanced proteolytic activity and/or denaturing in an inflammatory tissue and/or a malignant tumour, has immunoregulatory, inhibitory activity, i.e. that it is a physiological immunoinhibitor. The present invention thus further relates to the use of an isolated immune cell binding peptide, peptide fragment, neo-structure and/or neo-epitope of a protein normally occurring in serum, according to the present invention, for immunoregulation not only in cancer, but also in interleukin-2 dependent and/or inflammatory conditions and/or diseases, such as psoriasis, T-cell lymphoma, allograft rejection, GVH, ischemia-reperfusion injury, chronic inflammatory diseases and/or autoimmune diseases.

A still further aspect of the invention relates to a method for treating interleukin-2 dependent and/or inflammatory conditions and/or diseases by administering a therapeutically effective amount of the immunosuppressive peptide, peptide fragment, neo-structure and/or neo-epitope of a protein normally occurring in serum, according to the present invention.

One presently preferred embodiment of the present invention relates to a protein sequence, such as a peptide, peptide fragment, neo-structure and/or neo-epitope of normal serum albumin having a first glutamic acid at a distance of 3 to 7 amino acids from any lysine present in said sequence, preferably 4 to 6 amino acids from any lysine present in said sequence, more preferably 5 to 6 amino acids from any lysine present in said sequence, and having immunoregulatory activity.

In a preferred embodiment of the present invention said sequence contains a further glutamic acid at a distance of from 2 to 3 amino acids from said first glutamic acid.

In a preferred embodiment of the present invention the peptide, peptide fragment, neo-structure and/or neo-epitope of normal serum albumin has a peptide sequence selected from the amino acid sequences listed as SEQ.ID.NO(s). 1-81.

In a preferred embodiment of the present invention said sequence further contains an acidic amino acid at a distance of −12±1 amino acids from the first glutamic acid, and at a distance of +3±1 amino acids from the lysine.

A further aspect of the invention relates to a monoclonal antibody directed against one or more of a protein sequence, such as a peptide, peptide fragment, neo-structure and/or neo-epitope of normal serum albumin having a first glutamic acid at a distance of 3 to 7 amino acids from any lysine present in said sequence, preferably 4 to 6 amino acids from any lysine present in said sequence, more preferably 5 to 6 amino acids from any lysine present in said sequence, and having immunoregulatory activity.

In a preferred embodiment of the present invention the antibody is directed against a peptide, peptide fragment, neo-structure and/or neo-epitope of normal serum albumin corresponding to one or more of the peptide sequences selected from the amino acid sequences listed as SEQ.ID. NO(s). 1-81.

Another aspect of the invention relates to a method for diagnosing the optional presence of an immunosuppressing cancer or malignant tumour, by determining the presence of a peptide, peptide fragment, neo-structure and/or neo-epitope of normal human serum albumin having a first glutamic acid at a distance of 3 to 7 amino acids from any lysine present in said peptide, peptide fragment, neo-structure and/or neo-epitope, preferably 4 to 6 amino acids from any lysine present in said peptide, peptide fragment, neo-structure and/or neo-epitope, more preferably 5 to 6 amino acids from any lysine present in said peptide, peptide fragment, neo-structure and/or neo-epitope, and having immunoregulatory activity, as shown in one or more standard immune tests/standard tests on immune function, such as cytokine production, lymphocyte proliferation, blocking binding of anti-integrin antibody to its receptor.

Presently Preferred Sequences of a Peptide, Peptide Fragment, Neo-Structure and/or Neo-Epitope According to the Present Invention are Listed as Follows:

| Sequence | SEQ ID NO. |
|---|---|
| EENFK | 1 |
| EDHVK | 2 |
| ENCDK | 3 |
| ETFLK | 4 |
| ERAFK | 5 |
| ECCEK | 6 |
| ECYAK | 7 |
| ERQIK | 8 |
| EKCCK | 9 |
| EEGKK | 10 |
| EETFLK | 11 |
| ETFLKK | 12 |
| ETTLEK | 13 |
| ETYVPK | 14 |
| ERQIKK | 15 |
| ELVKHK | 16 |
| EVAHRFK | 17 |
| EVTEFAK | 18 |
| ECFLQHK | 19 |
| EETFLKK | 20 |
| ELLFFAK | 21 |
| ELRDEGK | 22 |
| EFAEVSK | 23 |
| EKPLLEK | 24 |
| ESKDVCK | 25 |
| EPQNLIK | 26 |
| EQLGEYK | 27 |
| EKERQIK | 28 |
| ESAENCDK | 29 |
| EMADCCAK | 30 |
| ECCQAADK | 31 |
| EGKASSAK | 32 |
| EEPQNLIK | 33 |
| EVSRNLGK | 34 |
| EKERQIKK | 35 |
| ELVKHKPK | 36 |
| ENQDSISSK | 37 |
| EKCCKADDK | 38 |
| ETCFAEEGK | 39 |
| KDLGE | 40 |
| KLVNE | 41 |
| KQEPE | 42 |
| KYLYE | 43 |
| KVHTE | 44 |
| KYICE | 45 |
| KECCE | 46 |
| KPLLE | 47 |
| KNYAE | 48 |
| KVFDE | 49 |
| KPLVE | 50 |
| KQNCE | 51 |
| KCCTE | 52 |

| Sequence | ID |
|---|---|
| KATKE | SEQ. ID. NO. 53 |
| KDLGEE | SEQ. ID. NO. 54 |
| KKYLYE | SEQ. ID. NO. 55 |
| KAAFTE | SEQ. ID. NO. 56 |
| KAEFAE | SEQ. ID. NO. 57 |
| KPLVEE | SEQ. ID. NO. 58 |
| KEFNAE | SEQ. ID. NO. 59 |
| KADDKE | SEQ. ID. NO. 60 |
| KTCVADE | SEQ. ID. NO. 61 |
| KLKECCE | SEQ. ID. NO. 62 |
| KSHCIAE | SEQ. ID. NO. 63 |
| KCCKHPE | SEQ. ID. NO. 64 |
| KRMPCAE | SEQ. ID. NO. 65 |
| KQTALVE | SEQ. ID. NO. 66 |
| KPKATKE | SEQ. ID. NO. 67 |
| KETCFAE | SEQ. ID. NO. 68 |
| KLVNEVTE | SEQ. ID. NO. 69 |
| KQEPERNE | SEQ. ID. NO. 70 |
| KLDELRDE | SEQ. ID. NO. 71 |
| KTYETTLE | SEQ. ID. NO. 72 |
| KQNCELFE | SEQ. ID. NO. 73 |
| KKQTALVE | SEQ. ID. NO. 74 |
| KETCFAEE | SEQ. ID. NO. 75 |
| KRYKAAFTE | SEQ. ID. NO. 76 |
| KDVCKNYAE | SEQ. ID. NO. 77 |
| KHKPKATKE | SEQ. ID. NO. 78 |
| EKDDAKCCK | SEQ. ID. NO. 79 |
| VFDEFKPLVEEPQNLIK | SEQ. ID. NO. 80 |
| VFDEFKPLVE | SEQ. ID. NO. 81 |

In the following the term "tissue" as used herein shall mean whole blood, serum, plasma, lymphatic fluid, saliva, urine, faeces, ascites, pleural effusion, pus, as well as any tissue, including muscle, fat, and connective tissue, including inflammatory cells.

In the present context, the term "protein sequence" is used to describe one or more of a protein, polypeptide, peptide, peptide fragment, neo-structure and/or neo-epitope that is generated as a result of proteolytic fragmentation, denaturation and/or conformational change(s) of a protein normally occurring in serum. As is easily understood by the person skilled in the art, a conformational change of a protein will of course not necessarily always lead to its fragmentation, but might as well simply result in the formation and/or presentation of a new structure and/or epitope. In the present context several new structures and/or epitopes are disclosed that are still attached to and presented by the original protein normally occurring in serum.

A fragment of a protein normally occurring in serum is in the present context defined as including fragments of proteins, polypeptides and or peptides, without reference to a specific length of said protein sequence.

In the present context, "denaturation" means any change of a protein's structure from the normal, natural structure, such as for example brought on by oxidative stress.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides, oligopeptides or polypeptides. In the context of the present invention, a "peptide" or "peptide fragment" for use in accordance with the present invention, refers to a polypeptide which may be, but is not limited to, being 5-50 amino acids in length, such as 5, 10, 15, 20, 25, 30, 35, 40, 41, 42, 43, 44, 45, 46, 47, 47, 48, 49 or 50 amino acids. Such peptides may also be longer than 50 amino acids.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of a peptide and/or peptide fragment of a sequence as listed in SEQ.ID.NO: 1-81, according to the invention, is also considered to be inside the scope of the present invention.

By a peptide, peptide fragment, neo-structure and/or neo-epitope having an amino acid sequence at least, for example 95% identical to a reference amino acid sequence, is intended that the amino acid sequence of e.g. the peptide is identical to the reference sequence, except that the amino acid sequence may include up to 5 point mutations per each 100 amino acids of the reference amino acid sequence. In other words, to obtain a peptide having an amino acid sequence at least 95% identical to a reference amino acid sequence: up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino and/or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

Results

Epitope Mapping with Mass Spectrometry of a Monoclonal Mouse Antibody Specific for Denatured Human Serum Albumin (dHSA)

Two monoclonal antibodies directed against denatured HSA were shown to have immunomodulatory activity. The structure of the epitope of one of these mAbs was further investigated.

Two Similar Approaches for Epitope Mapping with Matrix-Assisted Laser

Desorption/Ionisation Time-of-Flight mass spectrometry (MALDI-TOF ms) were used in order to define the possible site/s on human serum albumin to which a mouse monoclonal antibody specific for denatured albumin binds. One approach takes advantage of the fact that tryptic peptides to which an antibody is bound will not generate characteristic mass spectra in MALDI as they are "hidden" from the analysis (3). Another approach takes advantage of the fact that sites on a protein where an antibody has bound are protected from proteolysis (1, 2).

Binding of Peptides Generated by Trypsination of dHSA by Monoclonal Antibody A (mAb A)

Purified human serum albumin (HSA) was denatured with urea, reduced with DTT and alkylated as described (4). The denatured HSA was then subjected to trypsin treatment with a low concentration (0.02-2 ng/ml) of trypsin. However, the spectra obtained with MALDI were unsatisfactory, as the peptides masses typical for albumin were not found. Based on gel electrophoresis this preparation (digested by 0.02 ng/ml of trypsin) was found to contain substantial amounts of undigested albumin. Therefore, trypsin digestion was continued, at a higher concentration (5 µg/ml) in order to obtain the mass spectra usually used for identification of proteins by MALDI.

Some of the now completely cleaved albumin solution was incubated with the mAb A. MALDI-TOF ms was performed and spectra of enzyme-treated denatured albumin obtained in the presence or absence of mAb A were compared. Fourteen albumin massed were absent or reduced after incubation with mAb A (Table 1 A, Column D). The amino acid sequence of these peptides is shown in Table 1B. The spectra represent multiple areas encompassing residues 66 to 508 of the albumin molecule.

TABLE 1

A. Peptide residues of HSA binding to mAb A. Column C: Peak area of peptides before adsorption with mAb A. Column D: Peak area of peptides after adsorption with mAb A. Column E: Peak area of peptides when digestion of dHSA was protected by binding to mAb A

| A MH+ (m/z) | B Residue | C Peak area before Antibody incub. 2 spectra | D Peak area after antibody incub. 5 spectra | E Peak area tryps. Albumin + antib. 6 spectra |
|---|---|---|---|---|
| 1149.67 | 066-075 | 1970, 4092 | 0, 0, 0, 0, 0, | 0, 0, 0, 0, 0, 0, |
| 1017.59 | 089-097 | 1695, 5089 | 0, 0, 0, 0, 0, | 0, 0, 0, 0, 0, 0, |
| 933.56 | 098-105 | 1862, 4869 | 0, 0, 132, 0, 0 | 0, 0, 0, 0, 0, 0, |
| 1434.65 | 106-117 | 809, 1010 | 0, 0, 0, 0, 0, | 0, 0, 0, 0, 0, 0, |
| 927.55 | 162-168 | 6036, 13066 | 504, 118, 473, 281, 288 | 448, 895, 216, 724, 2346, 1571 |
| 1074.63 | 206-214 | 3064, 7917 | 0, 0, 0, 0, 0 | 0, 0, 0, 0, 0, 0, |
| 1443.74 | 287-298 | 583, 1394 | 0, 0, 0, 0, 0, | 0, 0, 53, 0, 0, 0, |
| 1546.91 | 299-310 | 2283, 4675 | 0, 0, 0, 0, 0, | 0, 0, 0, 0, 0, 0, |
| 1311.84 | 362-372 | 1036, 1482 | 0, 0, 0, 0, 0, | 0, 0, 51, 0, 407 (1312), 226(1312) |
| 1552.71 | 384-396 | 2186, 3327 | 0, 0, 0, 0, 0, | 0, 0, 0, 0, 0, 0, |
| 1657.87 | 414-426 | 2519, 2978 | 0, 0, 0, 0, 0, | 0, 0, 0, 0, 0, 212(1656.64) |
| 960.62 | 427-434 | 15276, 32846 | 267, 315, 931, 494, 309 | 591, 1284, 199, 1015, 2963, 1998 |
| 1138.56 | 500-508 | 1360, 4659 | 0, 0, 0, 0, 0, | 0, 258, 0, 0, 0, 204 (1139) |
| 1342.72 | 570-581 | 2720, 3758 | 0, 0, 0, 0, 0 | 0, 0, 0, 0, 0, 0 |

TABLE 1B

Amino acid sequence of the peptide residues of HSA bound by mAb A.

| MH + (m/z) | Residue | Sequence |
|---|---|---|
| 1149.67 | 066-075 | LVNEVTEFAK (SEQ ID NO: 104) |
| 1017.59 | 089-097 | SLHTLFGDK (SEQ ID NO: 84) |
| 933.56 | 098-105 | LCTVATLR (SEQ ID NO: 85) |
| 1434.65 | 106-117 | ETYGEMADCCAK (SEQ ID NO: 86) |
| 927.55 | 162-168 | YLYEIAR (SEQ ID NO: 87) |
| 1074.63 | 206-214 | LDELRDEGK (SEQ ID NO: 88) |
| 1443.74 | 287-298 | YICENQDSISSK (SEQ ID NO: 89) |
| 1546.91 | 299-310 | LKECCEKPLLEK (SEQ ID NO: 90) |
| 1311.84 | 362-372 | HPDYSVVLLLR (SEQ ID NO: 91) |
| 1552.71 | 384-396 | CCAAADPHECYAK (SEQ ID NO: 92) |
| 1657.87 | 414-426 | QNCELFEQLGEYK (SEQ ID NO: 93) |
| 960.62 | 427-434 | FQNALLVR (SEQ ID NO: 94) |
| 1138.56 | 500-508 | CCTESLVNR (SEQ ID NO: 95) |
| 1342.72 | 570-581 | AVMDDFAAFVEK (SEQ ID NO: 96) |

In order to further confirm these results the monoclonal antibody mAb A was allowed to bind to the denatured albumin (previously digested by trypsin at a concentration of 0.02 ng/ml) in order to protect the peptide sequences of the epitope. The complex was then again treated with trypsin. MALDI-TOF ms was then performed and the peptide mass spectra generated from albumin were compared with spectra generated from denatured albumin trypsin-treated in the absence of antibody. The same fourteen masses out of 39 albumin masses disappeared completely or were significantly reduced in the sample were the mAb was present during trypsin treatment (Table 1 A, Column E). Multiple readings were taken to verify the results.

Important peptide fragments might not be identified because of the possibility that the mAb binding epitope of albumin is cleaved by trypsin, resulting in fragments of the epitope with too low binding affinity to bind to the mAb. Therefore, an alternative method was also used.

MALDI epitope mapping of mAb A based on antibody protection of proteolysis was repeated. This time a slightly different approach was used. Denatured HSA was incubated with mAb A. Albumin not bound by the antibody, was removed from the sample by size exclusion on an ultra filter. The remaining free mabs and the complexes of mab-albumin was then digested with trypsin (sequences of the albumin molecule to which mab is bound should resist the trypsin digestion). Small cleaved fragments of mab and unprotected albumin was then removed from the sample by ultrafiltration (30 kD). The complexes of mAb and bound albumin fragments were dissociated by lowering the pH to 2.7. Again ultrafiltration at 30 kD was performed to separate whole mAb from albumin fragments smaller than 30 kD. MALDI TOF analysis of these fragments did not identify spectra typical for albumin. Reasonably, because the fragments containing the epitope of mAb A were still too large. This filtrate (<30 kD) was then further digested with trypsin (for cleavage of sites previously protected by the mAb) in order to generate peptide masses suitable for analysis with MALDI TOF ms.

After this second trypsin treatment, eight of 32 masses detected by MALDI TOF ms matched to albumin (Table 2). Thus, these now identified amino acid sequences comprise a part of the epitope, which also contains sequences on the other side of the trypsin cleavage point.

TABLE 2

Albumin peptides generated by trypsination of larger fragments eluted from mAb A.

| Mass | Albumin residue | Peak area | Database sequence |
|---|---|---|---|
| 875.49 | 243-249 | 481 | LSQRFPK (SEQ ID NO: 97) |
| 927.47* | 162-168 | 1035 | YLYEIAR (SEQ ID NO: 98) |
| 933.51* | 98-105 | 744 | LCTVATLR (SEQ ID NO: 99) |

TABLE 2-continued

Albumin peptides generated by trypsination of larger fragments eluted from mAb A.

| Mass | Albumin residue | Peak area | Database sequence |
|---|---|---|---|
| 940.41 | 131-138 | 534 | DDNPNLPR (SEQ ID NO: 100) |
| 960.55* | 427-434 | 1345 | FQNALLVR (SEQ ID NO: 101) |
| 1074.52* | 206-214 | 644 | LDELRDEGK (SEQ ID NO: 102) |
| 1138.47* | 500-508 | 119 | CCTESLVNR (SEQ ID NO: 103) |
| 1149.53 (1149.61)* | 66-75 | 1918 | LVNEVTEFAK (SEQ ID NO: 104) |

Six of the eight peptide masses (marked with * in Table 2) were peptide masses that also disappeared when analysed previously when completely cleaved albumin was incubated with the mAb A before the MALDI-TOF analysis (Tables 1A and B).

The epitope/s of this antibody was thus established. It is important to note that multiple such structures are present in the albumin molecule, which can then cause cross-linking of the receptors to which they are bound. A previous study into the antigenicity of albumin, based on 13 different monoclonal antibodies, has shown that intramolecular cross-reactivity exists between different domains in human albumin (5), thus multiple epitope sites for mAb A on albumin may be expected.

Based on these consistent results, a common pattern was found. Glutamic acid was found at a distance of 5 or 6 amino acids from lysine, either in the peptide sequences identified by MALDI-TOF or in the sequence adjacent to the peptide sequence identified by this technique (that is on the other side of the trypsin cleavage point, at K (lysine), (Table 3)). It is interesting to note that in 4 of these sequences an additional glutamic acid was found at a distance of 2 or 3 amino acids from the first glutamic acid residue. These additional glutamic acid residues might be of importance for the affinity or signal transduction of these peptides. The biological activity of these peptides might also be influenced by the occurrence of acidic amino acids both at a distance of 12±1 amino acids (position −12) from the first glutamic acid residue E (in the E5K structure) and at a distance of 3±1 amino acids (position +3) from the lysine residue K (in the E5K structure. Due to the length of the two important amino acids, glutamic acid (E) and lysine (K), in the epitope of mAb A, the exact fixed distance between these amino acids is not necessary for the immunoregulatory activity of these fragments. Thus, a sequence of E3-7K can have immunoregulatory activity similar to that of the E5K sequence (Table 4 A and B).

TABLE 3

Peptide sequences surrounding the E5K and E6K structures selected for synthesis of peptides for testing of immunological activity. One peptide with the E6K structure is included in the table (sequence 2).

| Name | SEQ ID NO | Residue / Mass | Sequence |
|---|---|---|---|
| Sequence 1 | SEQ ID NO: 105 | Residue 062-078 | D H V L V N E V T E F F A K T C V A |
| Mass MH+ (m/z) | SEQ ID NO: 104 | 1149.67 | |
| E5K motif | SEQ ID NO: 18 | | L V N E V T E F F A K |
| Synthesized peptide | SEQ ID NO: 106 | 2604 | K L V N E V T E F F A K T |
| Sequence 2 | SEQ ID NO: 107 | Residue 103-124 | T L R E T Y G E M A D C C A K Q E P E R N E |
| Mass MH+ (m/z) | SEQ ID NO: 139 | 1434.65 | |
| E5K motif | SEQ ID NO: 30 | | E T Y G E M A D C C A K |
| Synthesized peptide | SEQ ID NO: 108 | 2607 | E M A D C C A K Q E P E |
| Sequence 3 | SEQ ID NO: 109 | Residue 151-171 | F H D N E E T F L K K Y L Y E I A R R H P |
| Mass MH+ (m/z) | SEQ ID NO: 98 | 927.55 | |
| E5K motif | SEQ ID NO: 20 | | Y L Y E I A R |
| Synthesized peptide | SEQ ID NO: 110 | 2605 | F L K K Y L Y E |
| Sequence 4 | SEQ ID NO: 111 | Residue 202-219 | L L P K L D E L R D E G K A S A K |
| Mass MH+ (m/z) | SEQ ID NO: 136 | 1074.63 | |
| E5K motif | | | E L R D E G K |

TABLE 3-continued

Peptide sequences surrounding the E5K and E6K structures selected for synthesis of peptides for testing of immunological activity. One peptide with the E6K structure is included in the table (sequence 2).

| | | | | | | | | | | | | | | | | | | | | | | | |
|---|---|---|---|---|---|---|---|---|---|---|---|---|---|---|---|---|---|---|---|---|---|---|---|
| Synthesized peptide (SEQ ID NO: 22) | 2606 | | | | | | | | | | | K | L | D | E | L | R | D | E | G | K | A | S |
| Sequence 5 (SEQ ID NO: 113) | Residue 414-437 | Q | N | C | E | L | F | E | Q | L | G | E | Y | K | F | Q | N | A | L | L | V | R | Y | T | K |
| Mass MH+ (m/z) (SEQ ID NO: 101) | 960.62 | | | | | | | | | | | | | | | F | Q | N | A | L | L | V | R |
| E5K motif (SEQ ID NO: 27) | | | | | E | L | F | E | Q | L | G | E | Y | K | F |
| Synthesized peptide (SEQ ID NO: 114) | 2608 | | | | E | L | F | E | Q | L | G | E | Y | K | F |

Five of these peptides were synthesized (Table 3) and their immunoregulatory functions have been investigated. Based on these studies it was postulated that both stimulatory and inhibitory peptide sequences are present in serum albumin.

Conclusion—Epitope Mapping by MALDI-TOF MS

The Epitope of mAb A has Been Identified as the E5-6K Structure

The biologically relevant structure is thus E3-7K, possibly with additional acidic amino acid residues at positions −12 and +3. Taken together, these results indicate that mAb A can bind to multiple regions of the albumin molecule. Since the experiments were performed with denatured albumin, these epitopes are probably not sites generated by combining residues when the molecule is folded.

Binding Activity of E5K Peptides—Inhibition of mAb A Binding to dHSA

In order to test the specificity of the synthesized peptides, they were tested in an ELISA where inhibition of the binding of mAb A to plates coated with dHSA was analysed. A high binding of the antibody to the plate is thus consistent with no inhibitory activity and this binding is reduced when an inhibitory substance is added to the system. As shown in FIG. 1, four out of five peptides showed a dose dependent inhibition of the antibody to the dHSA coated plates, confirming that they contain a structure reacting with the antibody.

Expression of the E5K Epitope in Tumour Cells—Correlation to Survival

It has previously been demonstrated, by using immunohistochemical staining with mAb A, that the E5K epitope/structure is expressed by several types of cancer cells (WO 06/043891). A series of 20 biopsies from melanoma patients were stained using this technique and the staining intensity was scored from + to +++ using a light microscope. A considerable variation in staining intensity was observed. Based on the most intensely stained areas of the sections the patients were ranked from high to low expressors of E5K. The number of patients was then divided into two equal groups, high and low expressors, and a possible difference in survival between these groups was analysed according to Kaplan Meyer and a log rank analyses. As is shown in FIG. 2 a highly statistically significant difference in survival was found for high and low expressors.

Immunomodulatory Activity of E5K Peptides

Effect of Peptides on PHA Induced Proliferation of PBMCs

The effect of two albumin peptides, 2605 and 2608, on PHA induced proliferation of PBMCs from one healthy control and two cancer patients was tested. As shown in FIGS. 3 A and B, the response pattern is quite different between individuals, presumably due to the degree of immune stimulation of PBMCs in vivo and possibly also due to the occurrence of auto-antibodies to the neo-structures represented by the peptides. The importance of the degree of immune stimulation is demonstrated by comparing the effect of the peptides when the PBMCs are stimulated with either 5 or 10 μg/ml of PHA (compare. FIGS. 3 A and B). In addition to the inter-individual differences, also a biphasic response pattern was found, for example using peptide 2605 with PBMCs from K92, the lowest concentration was inhibitory, the middle concentration stimulatory and again at the highest concentration, the proliferative response was inhibited. It is also interesting to note that a clear stimulatory activity was found with the lowest concentration of both peptides in patient P46. There are also some differences in the activity of the two tested peptides especially when PBMCs are stimulated with PHA at a concentration of 5 μg/ml. When a PHA concentration of 10 μg/ml is used the activity of the two peptides is similar. The culture model with the lower degree of stimulation is of course more sensitive to variation in the receptor binding structure. This example thus demonstrates that once a biologically active peptide sequence has been demonstrated, changes of the amino acid sequence can modulate its biological activity.

To further analyse the inter individual differences in the effect of these peptides PBMCs from 5 healthy controls and 4 patients were analysed (FIG. 4). PHA was used at a concentration of 5 μg/ml and the peptides at a concentration of 10 μg/ml. Again a clear difference between individuals was demonstrated. Peptide 2605 had an inhibitory or stimulatory effects in one control each and one patient each. Peptide 2608 had a stimulatory effect in ¼ controls whereas ¾ patients were stimulated.

Effect of dHSA on PHA induced proliferation of peripheral blood mononuclear cells (PBMCs) The effect of dHSA on PHA induced proliferation of PBMCs from healthy controls and cancer patients is quite variable (FIG. 5). Again this can be due to the degree of stimulation of PBMCs in vivo and possibly also to the presence of auto-antibodies against dHSA. Addition of dHSA to these cultures can result both in stimulation and inhibition of the proliferative rate, but frequently resulted in stimulation of the proliferative rate. It is remarkable that one control did not respond at all and this person did not respond to a higher concentration of PHA either. In one patient (P41) addition of dHSA inhibited proliferation, especially at a PHA concentration of 10 μg/ml. The variation in response between patients, demonstrates the need of diagnosing the individual immune status of cancer patients.

Effect of Peptides on dHSA Modulated PHA Induced Proliferation of PBMCs

Next the effect of different peptides, 2605 or 2608, on dHSA enhanced PHA induced proliferation was analysed. As shown in FIGS. 6 A and B addition of dHSA at a concentration of 8 μg/ml significantly increased the proliferative rate of PHA stimulated PBMCs from two different healthy controls. At the lower concentrations of dHSA, the stimulatory activity declined. Interestingly, addition of the peptides at a concentration of 10 μg/ml significantly inhibited the stimulatory activity of the two highest dHSA concentrations, whereas at the lower concentrations the peptides to the contrary stimulated the proliferative rate. Thus, the stimulatory effect of dHSA at 8 □μg/ml was inhibited by addition of the peptides, but the same concentration of the peptides stimulated the proliferative rate at a lower concentration of dHSA. Reasonably, cross-linking of the E5K receptor is involved in the stimulatory activity of dHSA as monomeric binding of the peptides to this receptor inhibits the stimulatory effect of dHSA. The same concentration of the peptides then has quite different activity in the presence of different concentrations of dHSA, at 0.8 μg/ml there is still a slight inhibitory activity whereas at the lower concentrations of dHSA the proliferative rate is significantly enhanced. A reasonable explanation to this is that the stimulatory activity of the peptides is blocked by an inhibitory neo-structure of albumin at dHSA concentration of 8 μg/ml.

Effect of Peptides on Monokine Production by PBMCs

The effect of albumin peptides, 2604-2608, on LPS induced IL-6 production is shown in FIG. 7 A-C. Again, considerable inter-individual differences in the activity of the peptides are observed. Analysing PBMCs from one healthy control, peptide 2604 was stimulatory at the lowest concentration, whereas peptides 2606 and 2608 at this concentration were inhibitory (FIG. 7A). The activity also varied between the two melanoma patients, but in one of these patients all peptides had a stimulatory activity (FIG. 7 C).

Thus all five peptides have immunomodulatory activity, but the effect varies depending the immune status of the investigated individual.

Effect Albumin Peptides on Immunohistochemical Staining of PBMC Using an Anti-Integrin Antibody The immunobiological importance of albumin amino acid sequences was further studied by analysing their influence on the binding of a monoclonal antibody to the $\beta_2$-integrin LFA-1 (CD11a) on immune cells (FIG. 8 A-F). This molecule was chosen for these experiments, as it is known that binding of certain mAb's to this molecule seriously can modulate/inhibit functions of the immune system. The particular antibody chosen for these experiments has been shown to inhibit the binding of LFA-1 to ICAM-1 AND ICAM-3.

Cytospin preparations of mononuclear blood cells from healthy controls, cancer patients and a monocytic cell line, THP-1, were prepared (as described under materials and methods), dried and stored at −70° C. In the immunocytological staining, unspecific staining was blocked by incubation with 10% human AB serum. Some of the slides were preincubated for 60 minutes with albumin peptides at a concentration of 40 μg/ml, added to this 10% AB serum, as indicated in the FIG. 8 A-F. The staining procedure was then continued as described in material and methods. The staining intensity of slides stained with and without preincubation with the peptides was recorded semi quantitatively using a standard light microscope.

As shown in FIG. 8 A-F, binding of the mAb to LFA-1 can be inhibited by preincubation with the peptides. As mentioned in other sections of this document, the immune status of the donor of blood cells might influence the outcome of immunological analyses. Accordingly, the stainability of PBMCs from some donors seems to be uninfluenced by pre-incubation with the peptides and in a few cases with low initial stainability even enhanced staining was observed. The binding of the mAb to LFA-1 to the monocytic cell line THP-1 was clearly enhanced by pre-incubation with peptide 2606 (FIG. 8 A, B). These results clearly show that the structure of E5K interact with the β2-integrin in a way, which is of importance for the function of the immune system.

Binding of Peptides Generated by Trypsination of dHSA by Cell Surface Receptors

Based on the observation that immunoregulatory peptide sequences are present in serum albumin, there is the possibility that other sequences than the epitope of mAb A have immunoregulatory function. Therefore an artificial cell surface (ACS) was prepared as described in materials and methods. The mixture of peptides obtained after trypsination was adsorbed by ACS and the binding peptides were identified by comparing adsorbed and unadsorbed peptide solutions using the MALDI TOF ms technique. These peptides are shown in Table 5 A.

TABLE 5 A

Peptides generated by trypsin degradation of dHSA and the degree of adsorption to the receptors of ACS. The amino acids within brackets show the protease cleavage point and are not included in the identified masses.

| | ACS adsorbed peptides | | Synthesized E5K peptides | | |
|---|---|---|---|---|---|
| Per cent adsorbed | Sequence | Start End | E5K Peptide | Sequence | Start End |
| 0.71 | (K)KYLYEIAR(R) (SEQ ID NO: 115) | 161-168 | 2605 | | 153-168 |
| 0.64 | (K)KVPQVSTPLVEVSR(N) (SEQ ID NO: 116) | 438-452 | | | |
| 0.60 | (K)VFDEFKPLVEEPQNLIK(Q) (SEQ ID NO: 193) | 397-413 | | | |
| 0.59 | (K)VPQVSTPTLVEVSR(N) (SEQ ID NO: 142) | 439-452 | | EMADCCAKQEPE (SEQ ID NO: 108) | |
| 0.42 | (R)RPCFSALEVDETYVPK(E) (SEQ ID NO: 119) | 509-524 | | | |
| 0.41 | (K)FQNALLVR(Y) (SEQ ID NO: 101) | 427-434 | | | |
| 0.36 | (K)SLHTLFGDK(L) (SEQ ID NO: 84) | 89-97 | | ELFEQLGEYKF (SEQ ID NO: 114) | |
| 0.36 | (K)LKECCEKPLLEK(S) (SEQ ID NO: 122) | 299-310 | | EMADCCAKQEPE (SEQ ID NO: 108) | |
| 0.35 | (K)LCTVATLR(E) (SEQ ID NO: 85) | 98-105 | | | |
| 0.34 | (K)YLYEIAR(R) (SEQ ID NO: 115) | 162-168 | 2605 | | 153-168 |
| 0.32 | (K)CCAAADPHECYAK(V) (SEQ ID NO: 125) | 384-396 | | | |

TABLE 5 A-continued

Peptides generated by trypsin degradation of dHSA and the degree of adsorption to the receptors of ACS. The amino acids within brackets show the protease cleavage point and are not included in the identified masses.

| ACS adsorbed peptides | | | Synthesized E5K peptides | | |
|---|---|---|---|---|---|
| Per cent adsorbed | Sequence | Start End | E5K Peptide | Sequence | Start End |
| 0.29 | (K)AAFTECCQAADK (A) (SEQ ID NO: 126) | 187-198 | | KLDELRDEGKAS (SEQ ID NO: 112) | |
| 0.26 | (K)CCTESLVNR (R) (SEQ ID NO: 127) | 500-508 | | | |
| 0.26 | (K)QEPERNECFLQHK (D) (SEQ ID NO: 132) | 118-130 | 2607 | KLVNEVTEFAKT (SEQ ID NO: 106) | 110-122 |
| 0.23 | (K)AVMDDFAAFVEK (C) (SEQ ID NO: 129) | 570-581 | | | |
| 0.22 | (R)NECFLQHK (D) (SEQ ID NO: 130) | 123-130 | | | |
| 0.20 | (K)QNCELFEQLGEYK (F) (SEQ ID NO: 144) | 414-426 | 2608 | | 417-427 |
| 0.18 | (K)QEPERNECFLQHK (D) (SEQ ID NO: 132) | 118-130 | 2607 | | 110-122 |
| 0.13 | (K)VHTECCHGDLLECADDR (A) (SEQ ID NO: 133) | 265-281 | | | |
| 0.08 | (R)FKDLGEENFK (A) (SEQ ID NO: 134) | 35-44 | | EMADCCAKQEPE (SEQ ID NO: 108) | |
| 0.03 | (K)YICENQDSISSK (L) (SEQ ID NO: 135) | 287-298 | | | |
| 0.02 | (K)LDELRDEGK (A) (SEQ ID NO: 136) | 206-214 | 2606 | | 205-217 |
| 0.01 | (K)DDNPNLPR (L) (SEQ ID NO: 137) | 131-138 | | ELFEQLGEYKF (SEQ ID NO: 114) | |
| -0.02 | (K)LVNEVTEFAK (T) (SEQ ID NO: 138) | 66-75 | 2604 | EMADCCAKQEPE (SEQ ID NO: 108) | 65-76 |
| -0.08 | (R)ETYGEMADCCAK (Q) (SEQ ID NO: 139) | 106-117 | | | |
| -0.37 | (R)YKAAFTECCQAADK (A) (SEQ ID NO: 140) | 185-198 | | | |

Based on their degree of binding and their spatial relation to the E5K structures of albumin, four new peptides were selected to be synthesized and investigated for their immunoregulatory activity (Table 5 B).

TABLE 5 B

| ACS adsorbed peptides | | | | Synthesized albumin peptides | | |
|---|---|---|---|---|---|---|
| Per cent Adsorbed | Sequence | Start | End | Peptide | Sequence | Start End |
| 0.71 | (K)KYLYEIAR (R) (SEQ ID NO: 115) | 161 | 168 | 3026 | NEETFLKKYLYEIARRHPYFYAP (SEQ ID NO:145) | 153-176 |
| 0.64 | (K)KVPQVSTPTLVEVSR (N) (SEQ ID NO: 116) | 438 | 452 | 3029 | KVPQVSTPTLVEVSR (SEQ ID NO: 146) | 438-452 |
| 0.60 | (K)VFDEFKPLVEEPQNLIK (Q) (SEQ ID NO: 117) | 397 | 413 | 3028 | VFDEFKPLVEEPQNLIK (SEQ ID NO: 117) | 397-413 |

TABLE 5 B-continued

| | ACS adsorbed peptides | | | | Synthesized albumin peptides | |
|---|---|---|---|---|---|---|
| Per cent Adsorbed | Sequence | Start | End | Peptide | Sequence | Start End |
| 0.20 | (K)QNCELFEQLGEYK(F) (SEQ ID NO: 144) | 414 | 426 | 3027 | ELFEQLGEYKFQNALLVR (SEQ ID NO: 147) | 417-434 |
| Related E5K peptide 2605 (3026) | | | | | NEETFLKKYLYE (SEQ ID NO: 110) | 153-168 |
| Related E5K peptide 2608 (3027) | | | | | ELFEQLGEYKF (SEQ ID NO: 114) | 417-427 |

Immunomodulatory Activity of Peptides Generated by Trypsin

Effect of Peptides on dHSA Modulated PHA Induced Proliferation of PBMCs

Two of the peptides in the new series, 3026 and 3028, were tested and compared to peptide 2605 in an analysis for their effect on dHSA modulated PHA stimulated proliferation (FIG. 9). PHA induced proliferation of PBMCs from two healthy controls was further stimulated by dHSA. As shown in FIG. 9, all peptides inhibited the stimulatory activity of dHSA at the two PHA concentrations used. Also in this experiment, the degree of stimulation of PBMCs has an impact on the results.

Effect of Peptides on Interleukin-2 Induced Proliferation of PBMCs

The peptides of the new series, 3026-3029, were also tested for their effect on IL-2 induced proliferation. As shown in FIG. 10 A, ¾ peptides, 3026, 3027 and 3029, had no statistically significant activity. In contrast, peptide 3028 was highly inhibitory (p=0.005). It is interesting to note that this inhibitory effect was completely reversed by modulation of the Fc-receptor cross-linking (FIG. 10 B) similar to the situation previously described for IL-2 related immunosuppression in renal cell carcinoma (WO 03/099312 A1).

Effect of the New Series of Peptides on Monokine Production by PBMCs

The effect of the new series of peptides showed a considerable difference in effect even between healthy control individuals (FIG. 11). Peptide 3026 had no certain effect in one of the controls (PBMC 2), but had a clear biphasic effect in the other (PBMC1). In the latter case, the IL-6 production was stimulated at the three highest concentrations and was clearly inhibited at the lowest concentration. Peptide 3027 was slightly stimulatory in one of the controls and had an inhibitory effect in the other. Similar results were also found with peptide 3028. Peptide 3029 had a slight stimulatory effect in only one of the controls, at the two highest concentrations. It is interesting to note that all peptides except 3029 had an immunomodulatory effect at a concentration as low 10 ng/ml. Thus, all peptides had an effect in at least one of the analysed controls.

Similar to the effect of the new series of peptides on PBMC from healthy controls, also PBMC from cancer patients showed considerable inter-individual differences (FIG. 12). Peptides 3026 and 3027 both had a stimulatory effect in the renal cell carcinoma patient and in addition peptide 3027 also stimulated one of the melanoma patients. The other two peptides, 3028 and 3029, had essentially no effects in these tests. In contrast to the situation in the controls, no inhibitory effects were seen.

Binding of Peptides Generated by Asparaginase Degradation of dHSA by Cell Surface Receptors The full peptide sequence of albumin is not recovered using the MALDI-TOF technique after trypsin degradation. In addition, some sequences with the capacity to bind to cell surface receptors of immune cells, might have been degraded by trypsin treatment. Therefore, the same experimental procedure as described above was used also for a peptide mixture obtained by degradation using asparaginase. The resulting ACS binding peptides are shown in Table 6 A and B.

In addition to the peptides generated by trypsin degradation another six peptides with a molecular weight of 700-3600 Da were found to be efficiently adsorbed (≥65%) by the cell surface structures on the ACS column (Table 6A)

TABLE 6 A.

| | ACS Adsorbed ASP-DHSA | |
|---|---|---|
| Per cent adsobed | Sequence | Start End |
| 1.00 | DHVKLVNEVTEFAKTCVA (SEQ ID NO: 105) | 62-79 |
| 1.00 | DDKETCFAEEGKKLVAASQAALGL (SEQ ID NO: 151) | 586-609 |
| 0.87 | DRVTKCCTESLVNRRPCFSALEV (SEQ ID NO: 152) | 495-517 |
| 0.86 | DETYVPKEFNAETFTHA (SEQ ID NO: 153) | 518-535 |
| 0.65 | DSISSKLKECCEKPLLEKSHCIAEVEN (SEQ ID NO: 154) | 293-319 |
| 0.65 | DKLCTVATLRETYGEM (SEQ ID NO: 155) | 96-112 |

Seven peptides of a molecular weight between 3200 and 9000 Da were found to be completely adsorbed by ACS and for one of the peptides of this group, 37% was bound. In this analysis another 9 peptides were not at all bound by ACS.

TABLE 6 B

| | ACS Adsorbed ASP-DHSA | |
|---|---|---|
| Per cent adsorbed | Sequence | Start End |
| 1.00 | YSVVLL LRLAKTYETT LEKCCAAADP HECYAKVF (SEQ ID NO: 156) | 364-398 |

TABLE 6 B-continued

ACS Adsorbed ASP-DHSA

| Per cent adsorbed | Sequence | Start End |
|---|---|---|
| 1.00 | KLCT VATLRETYGE MA DCCAKQEP ERNECFLQHK (SEQ ID NO: 157) | 96-130 |
| 1.00 | ICTLSEKERQIKKQ TALVELVKHK PKATKEQLKA VM (SEQ ID NO: 158) | 536-572 |
| 1.00 | LAKYICE NQDSISSKLK ECCEKPLLEK SHCIAEVEN (SEQ ID NO: 159) | 283-319 |
| 1.00 | VF LGMFLYEYAR RHPDYSVVLL LRLAKTYETT LEKCCAAA (SEQ ID NO: 160) | 348-388 |
| 1.00 | LGE ENFKALVLIA FAQYLQQCPF EDHVKLVNEV TEFAKTCVA (SEQ ID NO: 161) | 37-79 |
| 1.00 | RVTKC CTESLVNRRP CFSALEVDET YVPKEFNAET FTFHA (SEQ ID NO: 162) | 495-535 |
| 0.37 | YLSVVLNQLCVLHEK TPVS DRVTKC CTESLVNRRP CFSALEV (SEQ ID NO: 163) | 475-517 |

Two peptides in this group did not bind at all and for one peptide (SISSKLKECCEKPLLEK SHCIAEVEN DEMPA) (SEQ ID NO:195) contradictory results were obtained regarding adsorption by ACS.

Thus, asparaginase treatment generates peptide sequences other than those generated by trypsin, which efficiently bind to cell surface structures of immune cells. Based on results described above these structures will most likely have an immunomodulating activity.

Occurrence of ACS Binding Fragments of IgG in Cancer Patients

In order to further identify the occurrence of immune cell binding structures in vivo, blood plasma was prepared and affinity chromatography was performed as described above. The substances bound by the ACS column were eluted, fractionated on 2D gel-electrophoresis and identified using the MALDI TOF technique. As expected the areas of the 2D gel corresponding to albumin and immunoglobulins were identified. In addition, other immune cell binding substances were also identified (FIG. 13). The binding of some variety of albumin, presumably damaged albumin carrying conformational changes, to immune cells has been previously described by several groups. The new immune cell binding structures found in this investigation are summarized in Table 7.

TABLE 7

Proteins identified by MALDI-TOF ms.

| | | |
|---|---|---|
| 1. | IgA heavy chain variable region | Acc. #: 3004672 |
| 2. | Immunoglobulin heavy chain variable and joining regions | Acc. #: 2198477 |
| 3. | Immunoglobulin heavy chain | Acc. #: 1669777 |
| | Ig heavy chain V region (clone LUNm03) | Acc. #: 484974 |
| 4. | SERTA domain-containing protein 2 (TRIP-Br2) | Acc. #: Q14140 |
| 5. | Immunoglobulin heavy chain variable region | Acc. #: 42632530 |

Thus, besides serum albumin also other normally occurring proteins are substrates for generation of immunoregulatory fragments.

Thus it can be concluded and as it is clearly shown in the present patent application that sequences of normally occurring proteins such as serum albumin and IgG bind to cell surface receptors of immune cells and have immunoregulatory activity. Both stimulatory and inhibitory sequences have been identified. In addition, cross-linking of receptors on immune cells was found to be one mechanism whereby the function of these cells can be modulated.

Human Ex Vivo Model for Evaluation of Immunosuppression in Cancer Patients

IL-2 is of fundamental importance for initiation and stimulation of an immune response and the activity of this cytokine is often inhibited in cancer related immunosuppression. Therefore, a human ex vivo model for immunosuppression in cancer patients (FIGS. 14 and 15) was set up for evaluation of possible inhibitory immunoregulatory peptides.

The response to IL-2 in this model was demonstrated to correlate to over-all survival of the patients (FIG. 15). Immunosuppression in this human ex vivo model is mediated by serum factors, as the proliferative capacity of PBMCs from healthy controls is significantly inhibited if these cells are cultured with cancer patient sera in the medium (FIG. 16).

Identification of Additional Immunoregulatory Peptides

Artificial cell surface columns (ACS) were used in order to identify peptide sequences from albumin binding to immune cell surface receptors. After biotinylation, such receptors were bound to streptavidin beads. Peptides binding to such columns were after elution identified by the MALDI-TOF technique. Based on these results and their relation to previously identified albumin peptides, five peptides were synthesized. Their immunoregulatory activity was primarily tested on the response to IL-2.

The effect of different peptides on IL-2 induced proliferation was analysed in the human ex vivo model. The 3028 peptide regularly inhibits IL-2 induced proliferation, but none of the other peptides identified by their binding to the artificial cell surface had any inhibitory activity (FIG. 17). As the C-terminal part of peptide 3028 contains a previously identified immunoregulatory structure, E5K, the effect of five peptides containing this structure was also tested on IL-2 induced proliferation, but these showed only a minimal or no inhibitory activity.

The inhibitory activity of peptide 3028 on IL-2 induced proliferation can be demonstrated also in cultures with cancer patient PBMCs, even if the response to IL-2 was already suppressed (FIG. 18) As immunosuppression in cancer is characterized by a poor response to IL-2, inhibition of the activity of this albumin neo-structure in cancer patients has a great capacity to overcome cancer related immunosuppression. This peptide inhibits one of the fundamental mechanisms in initiation and up-regulation of an immune response, it will therefore most likely be of great value in down-regulation of the immune reactivity in chronic inflammatory and auto-immune diseases.

Further Characterization of the Effect of Peptide 3028 on IL-2-Induced Proliferation of PBMCs As certain albumin neo-structures have previously been found to have immunomodulatory activity and the C-terminal part of peptide 3028 has a similar structure, the C- and N-terminal parts of peptide 3028 were synthesized and analyzed separately and in combination. Obviously the inhibitory activity of the two parts of peptide 3028 is much weaker (FIG. 19).

Characterization of a Rabbit Antiserum and Affinity Purified Rabbit Antibodies Directed Against the 3028 Peptide Rabbit antisera directed against the albumin peptide 3028 Binds to dHSA and to a lesser extent to kHSA. Two antisera, R and L, from two different rabbits were tested. These serum antibodies bind preferentially to the 3325 but not to the 3218 fragment of 3028. Similar results are also obtained with the affinity purified antibodies (see FIG. 21).

Immunomodulatory Effect of Affinity Purified Rabbit Antibodies Directed Against the 3028 Peptide As shown in FIG. 22, inhibition of the proliferative response to IL-2 was over-come in immunosuppressed cancer patients (FIG. 22A) and normal controls with down-regulation of the immune reactivity (FIG. 22 B) having a proliferative rate of less than 100 000 dpm in the human ex vivo model. The anti-3028 antibodies had no effect when the proliferative rate is in the normal range.

Polyclonal rabbit IgG was added to control cultures in order to make sure that the effect of the affinity purified antibodies was not due to an unspecific activity of rabbit IgG in this model. Rabbit IgG had only minimal activity. The specificity of the anti-3028 antibodies was further demonstrated as the stimulatory effect of these antibodies was neutralized by a small amount of peptide 3028 having no inhibitory activity per se. In addition adsorption of inhibitory sera by gel to which anti-3028 antibodies were bound reduced the inhibitory activity of such sera.

Similar to the results in the autologous ex vivo model the immunosuppressor activity of sera from persons with a low proliferative response to IL-2 was over-come by addition of the anti-3028 antibodies to the cultures.

Binding of Anti-3028 Antibodies to/Expression of the 3028 Epitope in/Malignant Tumours Structures to which anti-3028 antibodies bind are widely expressed in human malignant tumours, e.g. malignant melanoma, renal cell carcinoma and colorectal cancer (see FIG. 23).

The Receptor of Peptide 3028:

Binding of 3028 to LFA-1

Similar to the results described above for cancer patients sera and the previously identified immunoregulatory peptides the 3028 peptide have the capacity to modulate the binding of the LFA-1 antibody (HI 111) to LFA-1 of mononuclear blood cells. Both inhibition (FIG. 24) and enhancement of the binding have been demonstrated, reasonably depending on the structure of LFA-1 (activated or inactivated form) when the cytospin preparations of the cells were prepared. Also the C- and N-terminal parts of this peptide has been shown to have some inhibitory activity (FIG. 24).

In agreement with these results and the effect of the 3028 peptide on IL-2 induced proliferation, it is of quite some interest to note that the anti-LFA-1 antibody used in these experiments is a potent inhibitor of IL-2 induced proliferation. Similar results have previously been published by Vyth-Dreese et al. (1993).

Binding of 3028 to the α-Chain (CD25) of the IL-2 Receptor

As peptide 3028 significantly inhibits the proliferative response to IL-2, the amino acid sequence of this peptide was compared to that of IL-2 and certain similarities were found at the receptor binding site of IL-2 (Table 8).

TABLE 8

Homologies in amino acid sequence of albumin peptide 3028 and a segment of human interleukin-2, which participate in the interaction of interleukin-2 with interleukin-2 receptor alpha (CD25).

| Peptide 3028 (SEQ ID NO: 117): | V F D E F K P L V E E P Q N L I K |
|---|---|
| Human IL-2 (SEQ ID NO: 194): (a.a. 61-72) | E L K P L E E |

Based on this observation, the effect of peptide 3028 on the binding of IL-2 to CD25 was studied. The fusion protein of CD25 and the Fc-part of IgG was bound to protein G coated micro-plates/ELISA plates and the plates were incubated with biotinylated IL-2 with or without peptide 3028 present. Amazingly, the binding of IL-2 to CD25 was enhanced by peptide 3028, indicating a three-part interaction between IL-2, CD25 and 3028. Even if the binding of IL-2 to CD25 is enhanced the proper assembly of the high affinity receptor and/or signal transduction is blocked as peptide 3028 is a potent inhibitor of IL-2 induced proliferation (see above).

Next, it was demonstrated using computer assisted molecular modeling that peptide 3028 binds to CD25 at the IL-2 binding site (FIG. 25). It can thus be concluded that peptide 3028 has a dual immunoregulatory capacity by binding both to LFA-1 and the IL-2 receptor.

Peptide 3028, Optimal Immunosuppressive Structure:

The Physiological Inhibitory Peptide

Based on the results described above (difference in anti-proliferative activity of peptides 3218 an 3325, specificity of the affinity purified antibodies directed to peptide 3325 and not to peptide 3218, immunomodulatory activity these antibodies, and the effect of these peptides on the binding of the anti-LFA-1 mAb to immune cells) it can be concluded that neither of the minor peptides, 3218 or 3325, are as efficient as the complete peptide, 3028 (FIG. 26). However, both peptides inhibit the binding of mAb HI 111 to LFA-1. One reasonable explanation to this is that both of the minor peptides contribute to the full activity of the inhibitory effect of peptide 3028. It is thus logic to extend peptide 3325 with the N-terminal amino acids of peptide 3218. As the C-terminal extension of peptide 3325 is a lysine it would be of quite some interest to produce longer peptides in order test the possibility that the longer peptides are even more efficient than peptide 3028.

In order to maintain the physiological nature of this inhibitory peptide, the only relevant modifications of its structure is to change its length as discussed above.

This program will thus clarify the optimal structure of peptide 3028 to be used as an immunosuppressive drug for treatment of IL-2 related/dependent pathological conditions/diseases such as T-cell malignancies, allograft rejection of organ transplants, graft versus host disease (GVH), chronic inflammatory diseases such as psoriasis and some autoimmune diseases. The rational for the therapeutic use the immunoinhibitory peptide 3028 in these conditions is demonstrated by the therapeutic activity of monoclonal antibodies directed against CD25 (the Tac-receptor)

TABLE 9

| | 3028 | | |
|---|---|---|---|
| | 3325 | 3218 | |
| PHECYAK | VFDEFKPLVE (SEQ ID NO: 81) Some antiproliferative activity Weak binding to LFA-1 Binds to affinity purified antibodies | EPQNLIK (SEQ ID NO: 172) Some antiproliferative activity Weak binding to LFA-1 Does not bind to affinity purified antibodies | QNCELFEQ |

Comments on the Present Immunoregulatory Mechanism

As immunosuppression in cancer is characterized by a poor response to IL-2, inhibition of the activity of this albumin neo-structure in cancer patients have a great capacity to overcome cancer related immunosuppression. This peptide inhibits one of the fundamental mechanisms in initiation and up-regulation of an immune response, it will therefore most likely be of great value in down-regulation of the immune reactivity in chronic inflammatory and autoimmune diseases.

The immunoregulatory 3028-structure described in the present patent application is generated by a physiological mechanism present in inflammation and cancer. Therapeutic strategies based on these targets will therefore be generally applicable.

Based on current data the mechanism of action is species specific therefore analogous animal models are not applicable. Proof of concept is obtained in a human ex vivo model where the results correlates to over-all survival of cancer patients Antibodies Specific for Albumin Peptide 3028 for Therapeutic Use Antibodies, full-length or fragments, with specificity for 3028, as well as for any of the fragments disclosed in SEQ.ID.NO(s). 1-81, should preferably be either humanized or fully human for therapeutic applications. Such antibodies can be produced utilizing a number of established technologies.

To humanize an animal (e.g. mouse) monoclonal antibody, recombinant approaches are used to graft the complementary determining regions (CDRs) from an animal-derived hybridoma immunoglobulin cDNA to the corresponding regions of a matched human immunoglobulin cDNA. The resulting recombinant antibody can then be expressed and produced in a variety of organisms, f.ex. bacteria or mammalian cell lines.

Fully human antibodies can be obtained primarily through three different approaches; 1) by rescuing naturally occurring antibodies from immune human donors through Epstein Barr virus (EBV) transformation of B cells or through PCR-cloning and phage display. 2) by immunizing and producing hybridomas from transgenic mice, which have been created with a repertoire of human immunoglobulin germline gene sequences. 3) by screening synthetic phage libraries containing human antibody variable (V–) region genes and selecting antigen-binding V-regions through phage display. The selected antibody is then cloned.

There are now multiple commercial companies that develop human antibodies towards a defined protein/peptide on a for-fee basis. In addition, new "antibody-like" molecules (f.ex. anticalins, affilin, affibodies) are rapidly being developed and produced as potential drug candidates. (For a review, see for example: Peterson N C. Advances in monoclonal antibody technology: Genetic engineering of mice, cells and immunoglobulins. ILAR Journal, 2005, 46:314-9.)

Effect of Albumin Peptides on Cytotoxic Activity of Natural Killer (NK) Cells from Healthy Blood Donors Results The NK cytotoxic activity of blood mononuclear cells from four healthy donors were tested. As seen in figure XX, the presence of peptide 3028 and, to a lesser degree, peptide 3026 reduced the percent specific lysis of K562 target cells by all four donors. Inhibition was not seen in the presence of peptide 3027, however.

Materials and Methods

Preparation of Denatured Human Serum Albumin (dHSA)

Human serum albumin (HSA) infusion solution (Pharmacia, Uppsala, Sweden) was denatured and reduced by resuspending it at a final concentration of 10 mg/ml in 8 M urea and 10 mM dithiothretiol (both from Sigma Chemical Co, St. Louis, Mo.) in 50 mM Tris-HCL (pH 7.9) for 2 h at 25° C. The HSA was then alkylated by the addition of 60 mM iodoacetamide (Sigma) and further incubated for 2 h at 25° C. in the dark. The HSA solution was diluted to a concentration of 100 ug/ml with phosphate buffered saline (PBS, Gibco BRL) and dialyzed extensively against PBS using Spectrapore 4 dialysis tubing with a cut-off of mw 12000 (Spectrum Europe, Breda, The Netherlands). Control HSA was prepared in parallel by incubating HSA at 10 mg/m in Tris-HCL (pH 7.9) followed by dialysis. Before use in tissue culture experiments the dHSA was sterile filtered through a 0.22 μm syringe filter (Millipore Co, MA, USA). DHSA was either stored at 4° C. or freeze dried and stored at −20° C.

Enzymatic Cleavage of dHSA with Low-Dose of Trypsin

Buffer exchange to 25 mM NH$_4$HCO$_3$, pH 8, was performed on denatured HSA with Sephadex-G25 gel filtration (PD-10 desalting columns, Amersham Biosciences Europe, Uppsala, Sweden). Protein exchange was determined with Bio-Rad protein assay based on the Bradford dye-binding procedure following the manufacturer's recommendations (Bio-Rad Laboratories AB, Sundbyberg, Sweden). Sequencing grade modified trypsin (Promega, Madison, concentration after buffer WI) was added at a final concentration of 2, 0.2 or 0.02 ng/ml to denatured HSA (49 ug/ml). Alternatively, as a control, the equivalent amount of trypsin dilution buffer (50 mM $C_2H_4O_2$) was added. The mixture was incubated at 37° C. for 18 hours. Trypsin activity was stopped by passage of the sample over a column with soy bean trypsin inhibitor cross-linked to CNBr activated agarose (Sigma).

Complete Enzymatic Cleavage of dHSA with High Dose Trypsin Followed by Incubation with mAb A for Epitope Mapping Eight μg of low-dose trypsin-treated dHSA was freeze dried and then dissolved in 16 □l of sequencing grade modified trypsin (at 5 μg/ml) (Promega) and incubated at 37° C. for 18 hours. A portion (10 μl) of the tryptic digested peptides was reacted with the monoclonal antibody (mAb A) at a final concentration of 0.3 mg/ml for 2 hours at room temperature. The samples were stored at 4° C. over night and then analysed by MALDI TOF MS (see below).

Incubation of dHSA with mab Followed by Complete Enzymatic Cleavage with Trypsin for Epitope Mapping Denatured, low-dose trypsin-treated HSA (8 μg) in 25 mM NH$_4$HCO$_3$, pH 8, was incubated with 8 μg of the monoclonal antibody (mAb A) or with a PBS control for 2 hours at 4° C. A separate control consisting of 8 µg monoclonal antibody in 25 mM $NH_4HCO_3$ alone was also incubated in parallel. The samples were vortexed briefly every 10 min. The samples were then immediately dried over night in a SpeedVac vacuum concentrator (Savant, Farmingdale, N.Y.). The samples were then dissolved in 16 µl of sequencing grade, modified trypsin at 5 µg/ml (Promega) and incubated at 37° C. for 18 hours. The samples were stored at 4° C. over night and then analysed by MALDI TOF MS (see below).

Incubation of dHSA with mab Followed by Enzymatic Cleavage with Trypsin with Ultrafiltration Under Acidic Conditions for Epitope Mapping Denatured HSA (80 µg) was incubated with mAb A (10 µg) in PBS for 18 h at room temperature. To remove free dHSA, the dHSA-mAb A reaction mixture was centrifuged for 5 min at 3000 rpm in an Amicon Ultra-15 ultrafilter with a molecular weight cut-off at 100 000 Da (Millipore Co., Billerica, Mass.). The retentate was diluted in 25 mM $NH_4HCO_3$ and again centrifuged as described above. The retentate was transferred to a sterile eppendorf microcentrifuge tube in 0.4 ml 25 mM $NH_4HCO_3$ and 0.4 µg sequencing grade modified trypsin (Promega) was added. Digestion was carried out at 37° C. over night with gentle agitation. Trypsin and free (not antibody-bound) albumin fragments were removed by ultrafiltration on a Amicon Ultra-4 filter (mw cut-off 30 000 Da, Millipore Co.) for 5 min at 3000 rpm. This was repeated three times. The retentate was then transferred to a new ultra filter where the mAb A was disassociated from bound albumin by the addition of 600 µl 0.1 M glycine-HCl, pH 2.7, for 30 min at room temperature after which the ultra filter was centrifuged for 10 min at 3000 rpm. The filtrate was transferred to a sterile Eppendorf microcentrifuge tube and neutralized with Tris-HCl, pH 9. The sample was then immediately dried over night in a SpeedVac vacuum concentrator. The samples were then dissolved in 16 µl of sequencing grade modified trypsin (at 5 µg/ml) (Promega) and incubated at 37° C. for 18 hours. Zip Tip pipette tips (Millipore) containing $C_{18}$ chromatorgraphy media were used for desalting before the sample was analysed by MALDI TOF ms (see below).

MALDI TOF Mass Spectrometry

1 µl of each sample of the tryptic digestion was mixed with 1 µl of a saturated solution of α-cyano-4-hydroxycinnamic acid (0.02 mg/ml) in 70% acetonitrile/0.3% trifluoro acetic acid. 1 µl of that mixture was spotted on a stainless steel target plate and analysed using MALDI-TOF ms (Voyager-DE PRO, Applied Biosystems, CA, US) equipped with a 337 nm $N_2$ laser. Database searches for masses corresponding to human serum albumin in the resulting spectra were performed in NCBI or SwissProt with MS-Fit as search engine.

Albumin Peptides

All synthetic albumin peptides used herein were custom prepared by CSBio Co, Menlo Park, Calif. Peptides were >95% pure as confirmed by HPLC. Peptides were kept freeze dried at minus 20° C. Peptides were reconstituted in sterile $H_2O$ (Sigma) for use in ELISA or in RPMI1640 (GIBCO) for use in cell culture experiments. Peptides were sterile filtered through a 0.22 µm syringe filter (Millipore Co) before use in cell culture experiments.

Anti-dHSA ELISA, co-incubation of anti-dHSA mAb A with synthetic albumin peptides Duplicate wells in Hi-binding microtitre plates (Costar 2592, Corning Inc, NY, USA) were coated with 100 µl of dHSA diluted in PBS at 4.5 µg/ml and incubated at room temperature overnight. The wells where then washed with wash buffer consisting of 0.05% Tween-20 in PBS (Sigma) followed by blocking for 1 hr at 25° C. with 200 µl 0.5% gelatin prepared from bovine skin (Sigma) in PBS followed by washing in wash buffer. The monoclonal antibody mAb A, diluted in ELISA reagent diluent (0.01% gelatin and 0.05% Tween-20 in 20 mM Tris buffered saline (TBS, Sigma)) at 4 ug/ml was pre-incubated for 1 hr at room temperature with the indicated concentrations of the peptides. 100 µl of the monoclonal antibody alone, or, alternatively, the monoclonal antibody mixed with peptides, was then added per well and incubated for 1.5 hr at 25° C. followed by washing. Envision-HRP (DakoCytomation Norden A/S, Glostrup, Denmark) diluted 1/10 in ELISA reagent diluent was added and the plates incubated for 15 min at 25° C. followed by washing. Finally, substrate solution consisting of $H_2O_2$ and tetramethylbenzidine (R&D Systems Europe, Ltd, Abingdon, UK) was added. The reaction was stopped with 1M $H_2SO_4$ and the optical density measured as absorbance (A) at dual wavelengths, 450 nm and 570 nm, with a Multiscan EX microplate reader (Labsystems).

Correlation of Immunohistological Staining of Biopsies with an Anti-dHSA mab (mAb A) and Survival in Patients with Malignant Melanoma Biopsies from tumours obtained from twenty patients diagnosed with metastatic malignant melanoma were immediately snap frozen in liquid nitrogen and stored at −70° C. until use. Frozen tissue sections, 6-7 µm thick, were cut, thawed and fixed with acetone for 5 min at room temperature. The sections were first blocked with 10% normal human AB-serum for 1 h before staining. Primary antibody, consisting of monoclonal mouse anti-human denatured albumin (mAb-A) diluted in Tris buffered saline (TBS, pH 7.6) at 10 µg/ml, was then added and the slides incubated for 30 min. The slides were washed in TBS followed by Envision-Alkaline Phosphatase (DakoCytomation) for 30 min. After additional washing in TBS, the slides were incubated in alkaline phoshatase substrate consisting of Fast Red TR salt (Sigma), naphtol AS-MX (Sigma) and 5 mM levamisol (Sigma) to block endogenous alkaline phosphatase activity, for 20 min followed by washing in TBS. They were then counterstained in Mayer's haematoxylin for 1 minute and mounted in Glycergel (Dakopatts). Monoclonal mouse IgG1 against an irrelevant antigen (*Aspergillus niger* glukosoxidase, DakoCytomation) was used as a negative control. All incubations were performed at room temperature in a moist chamber. Intensity of staining was evaluated in a light microscope and was ranked as low, medium or high. Survival between groups was analysed according to Kaplan Meyer and a log rank analyses.

Isolation of Peripheral Blood Mononuclear Cells (PBMC)

Venous blood was drawn from healthy volunteers or from cancer patients in glass vacuum tubes with acid dextrose citrate solution A as anti-coagulant (Vacutainer, Becton Dickinson, Franklin Lakes, N.J.). Erythrocytes were removed by sedimentation on 2% dextran T500 solution (Amersham Pharmacia Biotech AB, Uppsala, Sweden) in 0.9% NaCl (this step was omitted for cultures with PHA-stimulation-see below). PBMC were then isolated by Ficoll-paque Plus (GE Healthcare Bio-Sciences AB, Uppsala, Sweden) density gradient centrifugation after which the cells were washed twice in RPMI 1640 Dutch's modification (Gibco, InVitrogen AB, Stockholm, Sweden) with 2% human serum albumin (HSA) (Pharmacia & Upjohn, Stockholm, Sweden) (RPMI/2% HSA). For cell cultures with PHA-stimulation, PBMC were washed in Hank's Balanced Salt Solution (HBSS) with 10% autologous plasma instead of RPMI/2% HSA. Cell viability was assessed by exclusion of 0.05% Trypan Blue and was always above 95%. The cell suspension was stained with Turk's solution and the number of lymphocytes and monocytes in the PBMC preparation were counted in a hemocytometer. PBMCs were suspended in RPMI/2% HSA and the cell concentration adjusted to $5 \times 10^5$ lymphocytes/ml.

Serum

Human serum was collected i serum collection tubes without additives (Vacutainer, Becton Dickinson, Franklin Lakes, N.J.) at the same time as blood samples for isolation of PBMC. The sera were heat-inactivated at 56° C. for 30 minutes.

PHA-Induced Proliferation of PBMC in the Presence of Albumin Peptides and/or dHSA PBMC from healthy volunteers, were resuspended in RPMI1640 with or without the addition of dHSA and/or albumin peptides, as indicated, at a cell concentration of $5 \times 10^5$ lymphocytes/ml. 100 µl of the cell suspension were seeded into round-bottomed microtiter plates (Corning, N.Y., USA) followed by 100 µl of culture medium consisting of RPMI 1640 (Flow Laboratories, Irvine, Scotland) supplemented with 200 IU/ml Penicillin, 200 µg/ml Streptomycin (Flow laboratories) and 20% heat inactivated autologous serum. Phytohemagglutinin (PHA-P, Sigma Chemical Co, St. Louis, Mo.) at a final concentration of 5 or 10 µg/ml was then added.

All culture conditions were set up in triplicate wells. Cells were cultured for 3 days in a humidified 5% $CO_2$ atmosphere at 37° C. Proliferation was assayed by incorporating of 1.6 µCi/well of [3H]thymidine (Amersham International, UK) during the last 18 hr. Mean values of disintegrations per minute (dpm) of triplicates were used for the calculations.

LPS-Induced IL-6 Production, Effect of Peptides

100 µl of culture medium consisting of RPMI1640 supplemented with 200 IU/ml penicillin, 200 µg/ml streptomycin, 4 mM L-glutamine (Sigma Chemical, Mo., US) and 20% fresh heat-inactivated autologous serum were added to un-coated or -pre-coated microtiter plates followed by 100 µl of PBMC suspension ($5 \times 10^4$ lymphocytes) in RPMI/2% HSA with peptides at the indicated concentrations. Lipoplysaccharide (LPS, Sigma Chemical Co, MO, US) was added at a final concentration of 0.05 ng/ml. Cells were cultured in a humidified, 5% $CO_2$ atmosphere at 37° C. All assay conditions were set up in triplicate wells. Supernatants (SNs) were harvested after 24 hrs and residual cells were removed by centrifugation in a refrigerated centrifuge (Beckman) at 2600×g for 5 minutes. SNs were frozen and stored at −70° C. IL-6 in cell culture SNs was measured by ELISA using the DuoSet® ELISA development kit for human IL-6 (R&D Systems Europe, Ltd., Abingdon, UK) following the manufacturer's recommended procedures. The lower limit of detection was 3.1 pg/ml. Samples were analysed as mean of triplicate wells.

Interleukin-2 (IL-2) Induced Proliferation of PBMC in the Presence of Albumin Peptides in Coated and Uncoated Tissue Culture Plates Round-bottomed, 96-well tissue culture plates (Costar, Corning Inc. NY, US) were pre-coated with HSA only or HSA and pooled human IgG for intravenous injection (Gammagard, Baxter AS, DK) as follows; HSA was diluted in RPMI1640 without supplements to a concentration of 10 mg/ml. A mixture of 1 mg/ml IgG in a solution of 9 mg/ml HSA in RPMI (HSA/IgG) was also prepared. 200 µl of HSA or HSA/IgG were then added to each well of the plate. The plates were incubated at 4° C. for 30 minutes after which the wells were washed twice with 200 µl of RPMI1640. The coated plates were used immediately. 100 µl of RPMI1640 supplemented with 200 IU/ml penicillin, 200 µl/ml streptomycin, 4 mM L-glutamine (all from Sigma Chemical Co. MO, US) and 20% heat-inactivated human serum (autologous) were added to the HSA or HSA/IgG coated tissue culture microtiter wells. PBMC, isolated from healthy individuals, were diluted in RPMI/2% HSA and peptides were added directly to the cell suspension at a concentration of 10 µg/ml. One hundred µl of this cell suspension ($5 \times 10^4$ lymphocytes) was then added per well providing a final concentration of 5 µg/ml peptide per well. IL-2 (Proleukin, Chiron, NL), at a final concentration of 120 IU/well, was added to the wells. Cells were cultured for 7 days in a humidified, 5% $CO_2$-atmosphere at 37° C. Proliferation was assayed by incorporation of 1.6 µCi/well of [3H]-thymidine (Amersham Int., UK) during the last 18 hrs. Mean values of dpm (disintegrations per minute) of triplicates were used for the calculations.

Immunocytochemical Staining of PBMC and a Human, Monocytic Cell Line with an Anti-Integrin (CD11a) Antibody in the Presence or Absence of Albumin Peptides PBMC were separated as described above. Cultured THP-1 cells (obtained from the American Type Culture Collection through LGL Nordic AB, Sweden) were carefully washed and suspended in RPMI1640. PBMC and THP-1 were immediately spun down on pre-cleaned microscope slides in a Shandon Cytospin (Shandon Scientific Ltd, UK) at 1000 RPM for 7 min at 2.5 or $5 \times 10^4$ cells per slide. The slides were left to dry at room temperature over night, after which they were wrapped in parafilm and stored at −70° C. Immediately before use, the cytospins were thawed and fixed with acetone for 5 min at room temperature. The cytospins were first blocked with 10% normal human AB-serum with and without albumin peptides (40 µg/ml) for 1 h before staining. Primary antibody, consisting of a monoclonal mouse anti-human CD11a (clone HI111, BD Biosciences) diluted in Tris buffered saline (TBS, pH 7.6) at 5 µg/ml (THP-1) or 1 µg/ml (PBMC), was added. The slides were incubated for 30 min and then washed in TBS followed by Envision-Alkaline Phosphatase (Dako Norden A/S, Denmark) for 30 min. After additional washing in TBS, the slides were incubated in alkaline phoshatase substrate consisting of Fast Red TR salt (Sigma), naphtol AS-MX (Sigma) and 5 mM levamisol (Sigma) to block endogenous alkaline phosphatase activity, for 20 min followed by washing in TBS. They were then counterstained in Mayer's haematoxylin for 1 minute and mounted in Glycergel (Dako Norden NS). Monoclonal mouse IgG1 against an irrelevant antigen (*Aspergillus niger* glukosoxidase, Dako Norden NS) was used as a negative control. All incubations were performed at room temperature in a moist chamber.

Proteolytic Fragmentation of Denatured Human Serum Albumin (dHSA) with Trypsin or Endoproteinase ASP-N Freeze dried dHSA (0.5 mg) was reconstituted in 25 mM $NH_4HCO_3$, pH 8, containing 10 mg sequencing grade modified trypsin (Promega Corporation, WI) or 2 mg Endoproteinase ASP-N (Sigma) and incubated at 37° C. over night. To remove unfragmented albumin and enzyme, the sample was ultra filtered through an Amicon Ultra 4 (mw cut-off of 5000) or a Centriplus (mw cut-off 10000) centrifugal filter (Millipore AB, Solna, Sweden). The filtrate, containing fragmented dHSA without enzymes, was collected and diluted with PBS with Ca and Mg (GIBCO).

Preparation of Cell Lysate from PBMC with Biotinylated Cell Surface Proteins (ACS)

Buffy coats generated from 450 ml blood each was collected from 4 healthy donors. Erythrocytes were removed by sedimentation on 2% dextran T500 solution (Amersham Pharmacia Biotech AB, Uppsala Sweden) in 0.9% NaCl. Mononuclear cells (PBMC) were then isolated by Ficoll-Paque Plus (GE Healthcare Bioscience AB Sweden) density gradient centrifugation. The PBMC were then suspended in phosphate buffered saline (PBS) containing Ca and Mg (GIBCO) at a concentration of $10 \times 10^6$/ml. EZ Link Sulfo-NHS-biotin (Pierce USA) was added at a final concentration of 0.2 mg/ml and the mixture incubated on a shaker at room temperature for 10 min. Excess biotin was then removed by washing the PBMC in PBS. Biotinylated PBMC were then lysed by adding 1.0 ml ice-cold lysing buffer (50 mM Tris-HCL, pH 7.5, with 0.15 M NaCl, 5 mM $MgCl_2$ containing 100 mM Octyl glucoside and 1 mM Phenylmethyl-sulfonyl fluoride) per $2 \times 10^7$ pelleted cells with gentle shaking, then incubated for 30 min. on ice. Debris was removed by centrifugation at 5000×g at 4° C. for 10 min and the supernatants was collected and pooled from all four donors. The lysate was then stored at −70° C. in polypropylene plastic tubes.

Preparation of affinity column with biotinylated cell surface proteins from mononuclear cells coupled to streptavidin-sepharose (used for adsorption of trypsin fragmented dHSA) 18 ml biotinylated cell lysate in lysate buffer was diluted 1/10 in binding buffer (20 mM $NaH_2PO_4$, 0.15 M NaCl, pH 7.5). This amount of lysate corresponds to $36 \times 10^7$ mononuclear cells. It was added to a 1 ml Hitrap Streptavidin HP affinity column (Amersham Biosciences). To block possible remaining free biotin, 5 ml of 0.1 M glycine (Sigma) was added to the column. Unsaturated streptavidin on the column was then reacted with 150 ug biotin (Sigma) in binding buffer. The column was carefully washed with PBS and stored in PBS with 0.1% $NaN_3$ at 4° C. until use.

Preparation of affinity column with biotinylated cell surface proteins from mononuclear cells coupled to streptavidin-sepharose (used for adsorption of ASP-N fragmented dHSA) Biotinylated cell lysate in lysate buffer underwent buffer exchange by dialysis with Spectrapore 4 dialysis tubing (Spectrum Europe, Breda, The Netherlands) in binding buffer (20 mM $NaH_2PO_4$, 0.15 M NaCl pH 7.5). 27 ml biotinylated cell lysate in binding buffer (corresponding to $54 \times 10^7$ mononuclear cells) was added to 1.5 ml washed Streptavidin Sepharose HP (Amersham Biosciences). To block possible remaining free biotin, 25 ml of 0.1 M glycine (Sigma) was added to the Streptavidin Sepharose. Unsaturated streptavidin was then reacted with 225 µg biotin (Sigma) in binding buffer. The Streptavidin Sepharose was carefully washed in PBS. One ml of the biotinylated cell lysate coupled Streptavidin Sepharose was then packed in an empty column (Tricorn Empty High Performance Column, Amersham Bioscience) and washed with phosphate buffered saline (PBS) containing Ca and Mg (GIBCO).

Adsorption of Enzyme Fragmented dHSA Using an Affinity Column with Biotinylated Cell Surface Proteins (ACS)

Two ml of enzyme-fragmented dHSA in PBS, corresponding to a total of 0.2 mg protein, was passaged over the ACS column, prepared as described above. The flow-through was collected with consideration taken to void volume and dilution of adsorbed sample by collecting in small portions of 0.2 ml. Thirty ul of each sample, including a control sample that has not been adsorbed, were dried in a Speed-Vac centrifuge.

Mass Spectrometry

Dried samples were reconstituted in 10 ul of 0.1% TFA. Zip Tip pipette tips (Millipore, USA) containing $C_{18}$ reversed-phase media were used for desalting reconstituted samples. For analysis of samples in the mass range 700-3600 Da, one µl of each Zip Tip eluted sample was mixed with 1 µl of a saturated solution of α-cyano-4-hydroxycinamic acid (0.02 mg/ml) in 70% acetonitrile/0.3% trifluoro acetic acid. For the analysis of samples in the mass range 1500-9000 Da, one µl of each Zip Tip eluted sample was mixed with 1 µl of sinapinic acid (3-methoxy-4-hydroxycinnamic acid). 1 µl of the mixture was spotted on the MALDI plate and analysed using MALDI-TOF MS (Voyager-DE PRO, Applied Biosystems, CA, US). Mass identity search of resulting spectra was performed in the SwissProt or NCBI databases using MS-Fit.

Identification of Proteins in Human Plasma Binding to ACS

Affinity Chromatography of Plasma with ACS

Plasma was obtained by plasmapheresis from a patient diagnosed with malignant melanoma. The plasma was frozen at −20° C. Upon thawing the plasma was immediately clotted by the addition of $CaCl_2$ to a final concentration of 13 mM. The gelled plasma clot was removed by centrifugation at 3500 RPM for 7 min at 4° C. The plasma was then dialysed extensively against PBS using Spectrapore 4 dialysis tubing (Spectrum Europe, Breda, The Netherlands). An affinity column with biotinylated cell surface proteins from mononuclear cells coupled to streptavidin-sepharose (ACS-sepharose) was prepared as described above. 45 ml of the plasma was incubated with the ACS-sepharose over night at 4° C. with gentle agitation. The plasma-ACS sepharose was extensively washed with PBS. The washed ACS-sepharose was stored for five days at 4° C. in PBS with 0.1% $NaN_3$. The ACS-sepharose was packed in an empty column (Tricorn Empty High Performance Column, Amersham Bioscience) and bound proteins were eluted with 2 ml of 0.1 M Glycine-HCl, pH 2.7. The eluated fraction was immediately neutralized with 1 M Tris buffer at pH 9 and freeze dried.

2-D Gel Electrophoresis

Freeze dried samples were desalted by reconstituting in $H_2O$ and 10% trichloro acetic acid (TCA) with 20 mM DTT in acetone. The samples were centrifuged at 13000 RPM for 5 min. The resulting pellet was washed twice with 20 mM DTT in acetone to remove TCA and finally dissolved in a rehydration buffer (8 M urea, 4% CHAPS, 10 mM DTT, 0.5% IPG buffer and a trace of orange G). Two-dimentional gel electrophoresis was performed in a horizontal 2-DE set-up (Multiphore/IPGphore, Pharmacia Biotech, SE) based on isoelectric focusing (IEF) in the first dimension and molecular mass in the second dimension. Briefly, samples were applied to IPG gels (Immobiline™ Dry strip, pH 3-10 NL, (GE Healthcare)) and focused overnight at 38060 Vh. SDS-PAGE was then carried out with Exelgel XL SDS 12-14 polyacrylamide precasted slab gels (Amersham Biosciences). Molecular weight standards were included in each run. Separated proteins were detected by silver stain according to the method of Shevenco. Tryptic digests of proteins spots were excised from the gel and analysed with MALDI-TOF ms as described above.

Cancer Patients

Patients, included in the analyses of over-all survival according to proliferative response of peripheral blood mononuclear cells (PBMC) to interleukin-2, were diagnosed with systemic metastatic renal cell carcinoma. They were previously untreated and scheduled for Interleukin-2 treatment (Proleukin, Chiron, NL). Blood samples were taken prior to initiation of treatment. Patients included in other studies in this patent application are briefly described as appropriate in the result section.

Ex Vivo Model of IL-2 Related Immunosuppression; Interleukin-2 (IL-2) Induced Proliferation of PBMC PBMC were isolated from venous blood samples from healthy blood donors (controls) or cancer patients. One hundred µl of culture medium (RPMI 1640 Dutch's modification (Gibco, InVitrogen AB, Stockholm, Sweden) supplemented with 200 IU/ml penicillin, 200 µl/ml streptomycin, 4 mM L-glutamine (all from Sigma Chemical Co. MO, US) and 20% heat-inactivated human serum) were added to round-bottomed, 96-well tissue culture plates (Costar, Corning Inc. NY, US). One hundred µl of PBMCs in RPMI/2% HSA ($5\times10^4$ lymphocytes) was then added per well followed by IL-2 (Proleukin, Chiron, NL) at a final concentration of 120 IU/well. Control wells without IL-2 was set up in parallel. Cells were cultured for 7 days in a humidified, 5% $CO_2$-atmosphere at 37° C. Cell proliferation was assayed by incorporation of 1.6 µCi/well of [3H]-thymidine (Amersham Int., UK) during the last 18-24 h hrs. Mean values of dpm (disintegrations per minute) of triplicate wells were used for the calculations. In cultures were serum collected from cancer patients were used instead of autologous serum, PBMCs were from blood type compatible donors.

Interleukin-2 (IL-2) induced proliferation of PBMC in the presence of albumin peptides Cultures for IL-2 induced proliferation was set up with PBMC from healthy donors and autologous serum as described above with the exception that PBMC were first pre-incubated for 30 min at room temperature with the indicated albumin peptides at a concentration of 10 µg/ml.

Generation of Rabbit Antiserum Specific for Albumin Peptide 3028

Peptide 3028 was synthesized with a cysteine added to the N-terminus end and then conjugated with keyhole limpet hemocyanin (KLH) as a carrier protein. Polyclonal antisera were generated by repeated immunizations of rabbits with KLH-conjugated peptide 3028 and Freund's adjuvants. For some experiments, the antisera were affinity purified by chromatography on peptide 3028-conjugated Ultralink Iodoacetyl gels (Pierce Biotechnology Inc.). For cell culture experiments, buffer exchange to RPMI 1640 Dutch's modification (Gibco, InVitrogen AB, Stockholm, Sweden) was performed by passage over PD-10 sephadex columns (Amersham Biosciences, Uppsala, Sweden) followed by filter sterilization on 0.22 µm Millex syringe filters (Millipore Co., MA, USA). Rabbit immunizations and purification of antisera were carried out by Agrisera AB, Sweden.

ELISA with Rabbit-Anti 3028 Antiserum

Duplicate wells in Hi-binding microtitre plates (Costar 2592, Corning Inc, NY, USA) were coated with 100 µl of peptide 3028 (10 ug/ml), denatured HSA (denHSA, 4.5 ug/ml) or control HSA (4.5 ug/ml). All coating reagent were diluted in PBS and incubated at room temperature overnight. The wells where then washed with wash buffer consisting of 0.05% Tween-20 in PBS (Sigma) followed by blocking for 1 hr at 25° C. with 200 µl 0.5% gelatin prepared from bovine skin (Sigma) in PBS followed by washing in wash buffer. Rabbit preimmune sera or anti-3028 sera, diluted 1/1000 000 in ELISA reagent diluent (0.01% gelatin and 0.05% Tween-20 in PBS), were added and incubated for 1 h at 25° C. followed by washing. Biotinylated horse anti-rabbit/mouse IgG (Vectastain ELITE, Vetor Laboratories Inc, CA, USA) diluted 1/5 in ELISA reagent diluent was then added and the plates incubated for 1 h at 25° C. followed by washing. Next, HRP-conjugated streptavidin (R&D systems Europe, Ltd, UK) was added. Finally, after washing in wash buffer, substrate solution consisting of $H_2O_2$ and tetramethylbenzidine (R&D Systems) was added. The reaction was stopped with 1M $H_2SO_4$ and the optical density measured as absorbance (A) at dual wavelengths, 450 nm and 570 nm, with a Multiscan EX microplate reader (Labsystems).

Inhibition of Rabbit Anti-3028 ELISA by Albumin Peptides

To test if albumin peptides inhibited the binding of the rabbit anti-3028 to 3028 coated wells, rabbit antisera, diluted 1/1000 000 in ELISA reagent diluent, was pre-incubated for 1 hr at room temperature with the indicated concentrations of the peptides. 100 µl of the monoclonal antibody alone, or, alternatively, the monoclonal antibody mixed with peptides, was then added to 3028 coated wells and the ELISA carried out as described.

Interleukin-2 (IL-2) Induced Proliferation of PBMC in the Presence of Affinity Purified Rabbit Anti-3028

Cultures to test the immunomodulatory effect of affinity purified rabbit antibodies specific for 3028 was performed as described above for IL-2 induced proliferation with the following exceptions; 2% HSA was omitted from the washing medium and from the PBMC suspension medium. Serum containing culture medium (100 ul/well) was pre-incubated with 20 ug/ml of rabbit antibodies for 30 min at room temperature before the addition of 100 ul PBMC suspension to the culture wells.

Immunohistochemical Staining of Tumor Biopsies with Rabbit Anti-3028

Tissue sections were prepared from formalin fixed biopsies from cancer patients. Sections were de-paraffinased and blocked with 10% normal, human AB-serum in Hank's balanced salt solution supplemented with 0.01 M Hepes (BSS, GIBCO BRL) for one h prior to staining. Sections were then stained with 10 ug/ml affinity purified rabbit anti-3028 diluted in BSS with 2% AB-serum and 0.1 g/ml saponin for 30 min. After washing in BSS with 0.1 g/ml saponin, Ultravison One alkaline phosphatase polymer specific for mouse and rabbit Ig (Lab Vision Co., CA, USA) was added. Excess polymer was then washed from the sections with BSS with 0.1 g/ml saponin. Bound polymer complex was the detected by naphthol phosphate substrate and liquid Fast Red chromogen (Lab Vision Corp.) The sections were counter stained in Mayer's haematoxylin and mounted in Glycergel.

Effect of Albumin Peptides on Cytotoxic Activity of Natural Killer (NK) Cells from Healthy Blood Donors Mononuclear cells were separated by standard Ficoll-paque Plus (Pharmacia AB, Sweden) density gradient centrifugation from heparinized blood obtained from healthy donors. NK cell cytotoxic activity of the mononuclear cells was then tested using a commercial kit (NKTEST, Orpegen Pharma GmbH, Heidelberg, Germany) following the manufacturers protocol. Briefly, the kit contains cryopreserved, NK-sensitive target cells (K562) labelled with a lipophilic green fluorescent membrane dye, which enables discrimination of effector and target cells. After incubation with effector cells, killed target cells are identified by a DNA-stain, which penetrates and specifically stain the nuclei of dead target cells. This way the percentage of killed targets can be determined by flow cytometry. The mononuclear cells were pre-incubated for 30 min at 37° C. with the indicated peptides (peptides have been described previously) at 10 ug/ml. Target cells were then added, giving an effector:target ratio of 40:1, and the cell mixture incubated at 37° C. for 3-4 hours. Samples were analysed on a FACSCalibur (BD Biosciences, San Jose, Calif.).

| Low expression  | ～～～ | x - - x |
| High expression | ▬▬▬ | o - - o |

Figure 1:
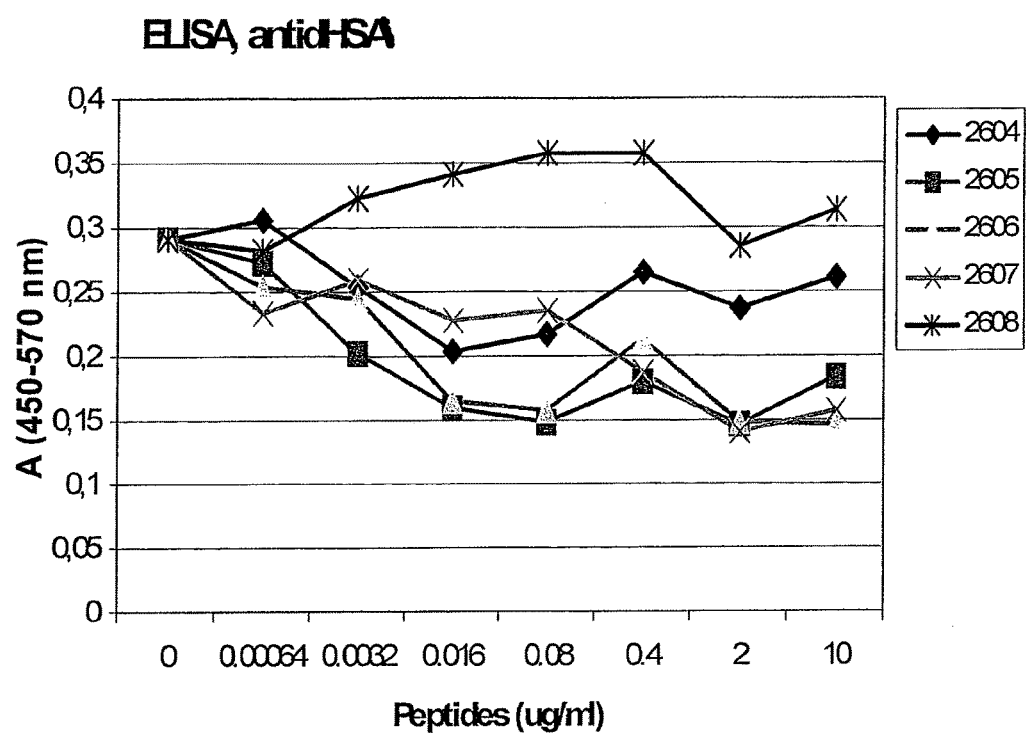
FIG. 1. This diagram shows that some peptides containing the E5K sequence inhibit the binding of mAb A to ELISA plates coated with dHSA. Obviously there is some differences in the inhibitory activity of the tested peptides.
Figure 2:
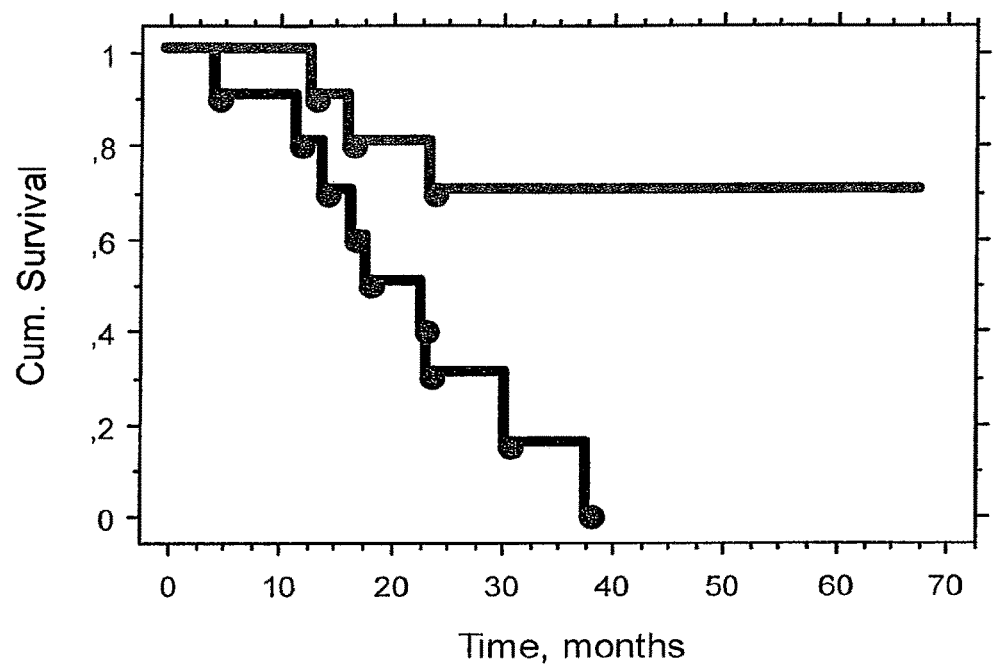
FIG. 2. Effect of expression of E5K detected by mAb A on survival of patients with metastatic malignant melanoma (p=0.009).
Figure 3A:
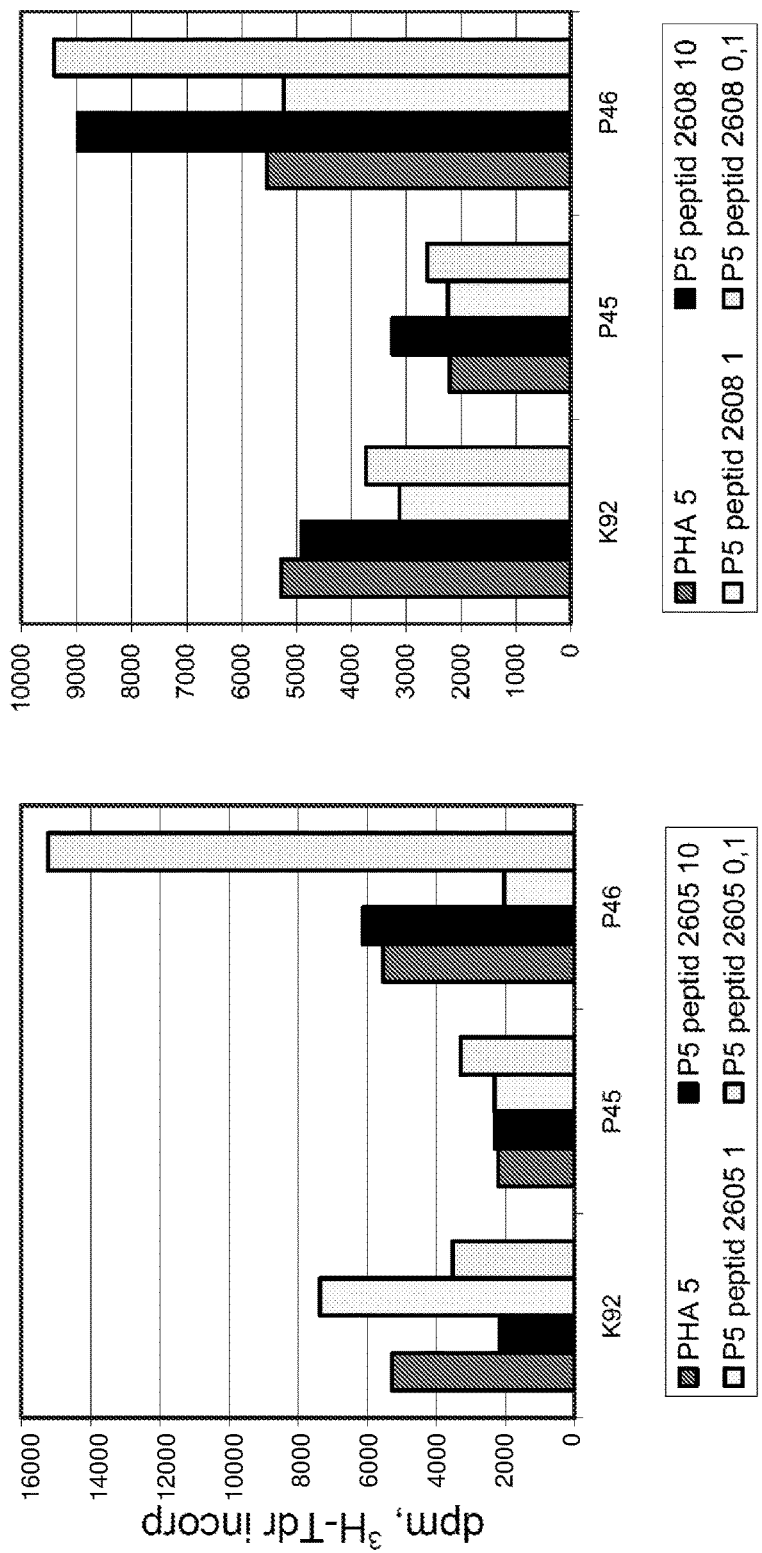
Figure 3B:
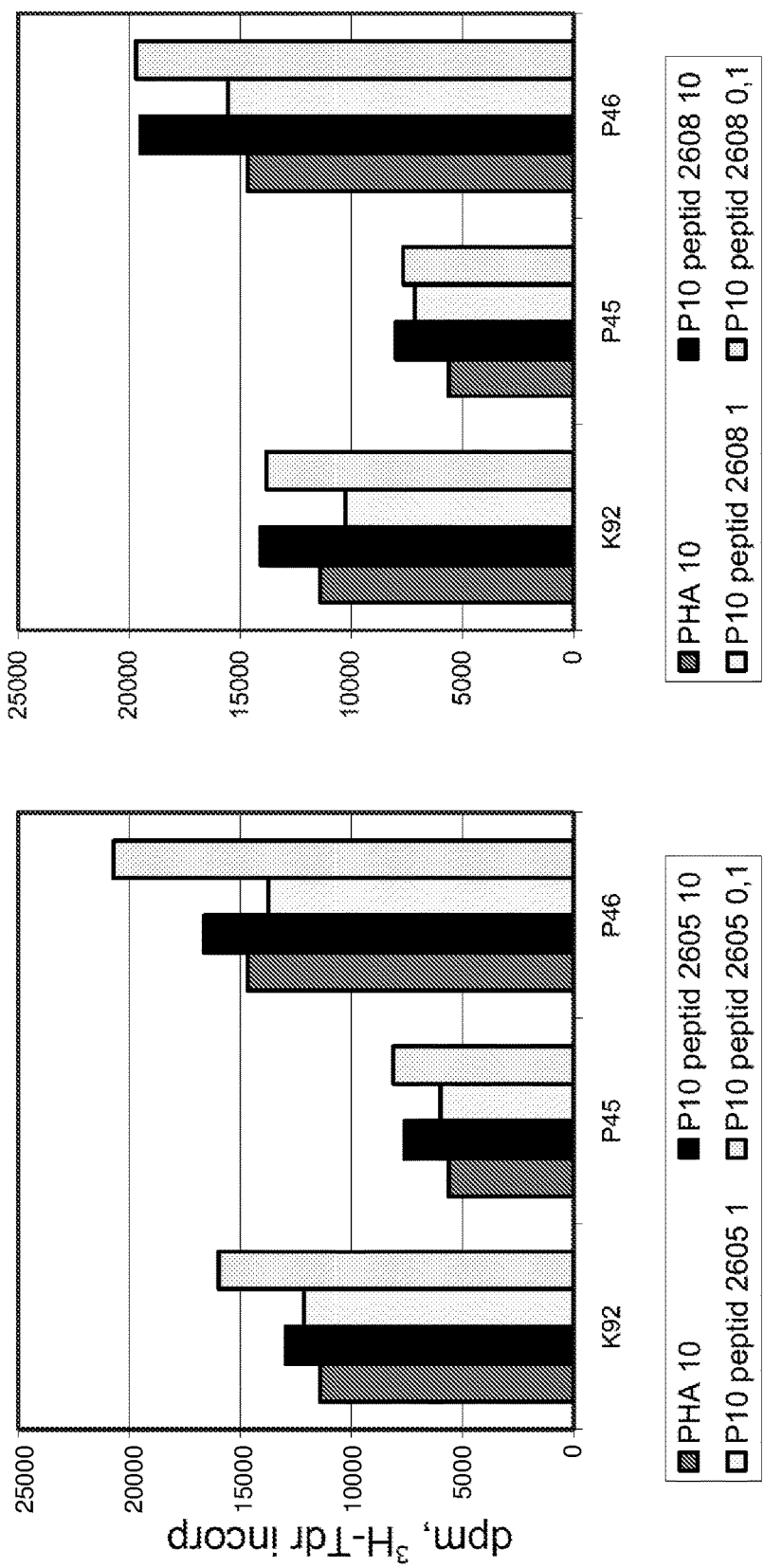

FIG. 3 A. Effect of two albumin peptides, 2605 and 2608, on PHA (5 μg/ml) induced proliferation of PBMCs from one healthy control and two cancer patients was tested. The three different concentrations of the peptides (μg/ml) are indicated in the figure. Patients P45 and 46 suffered from renal cell carcinoma and malignant melanoma.

FIG. 3 B. Effect of two albumin peptides, 2605 and 2608, on PHA (10 μg/ml) induced proliferation of PBMCs from one healthy control and two cancer patients was tested. The three peptide concentrations (μg/ml) used are indicated in the figure.

Figure 4:
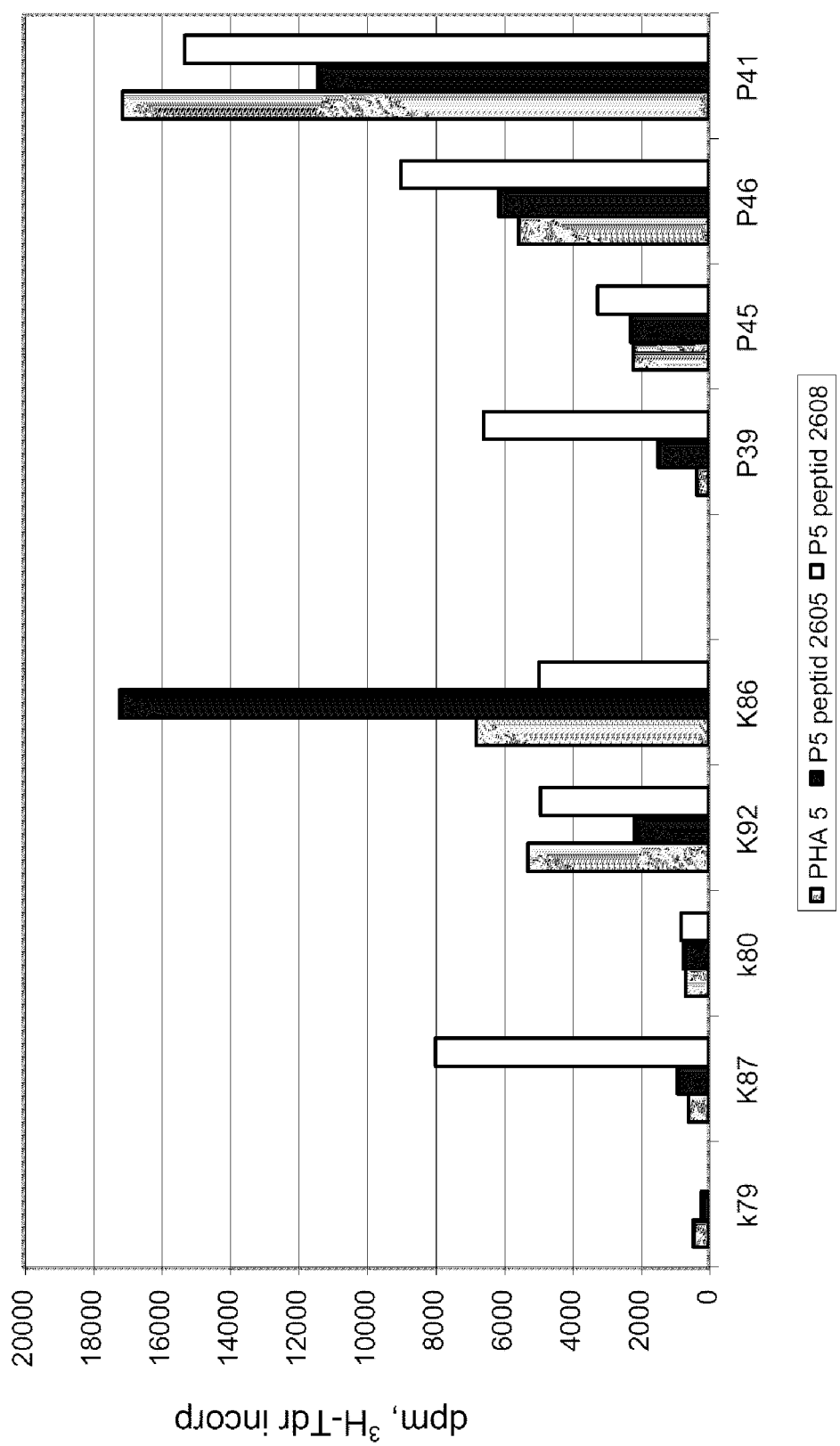

FIG. 4. Inter-individual variation in the effect of albumin peptides on PHA induced proliferation by PBMCs from healthy controls and cancer patients. PHA was used at a concentration of 5 μg/ml and the peptides at a concentration of 10 μg/ml. The patients had the following diagnoses: Malignant melanoma (P46) and renal cell carcinoma (P39, P 41 and P45).

Figure 5:
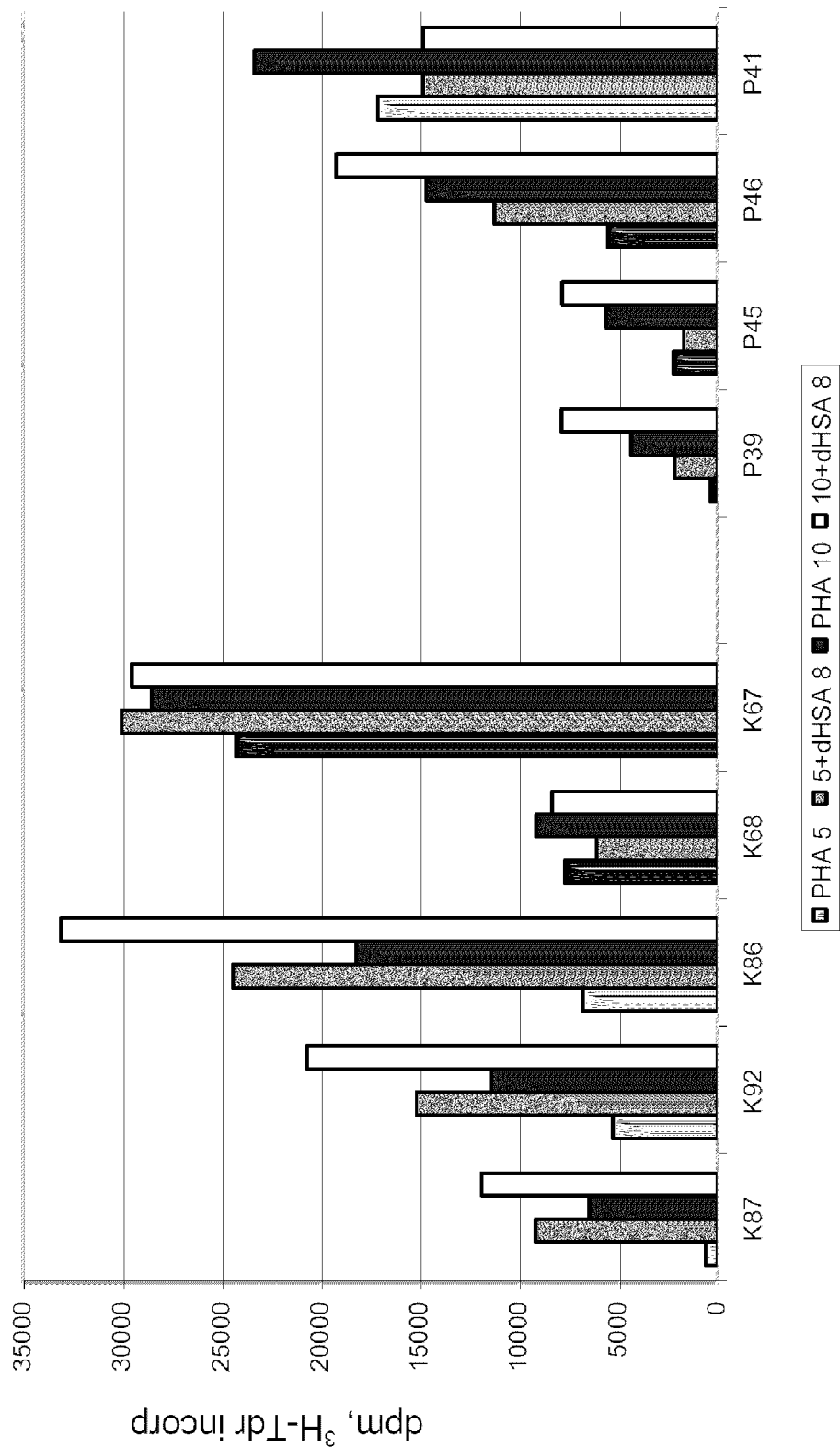

FIG. 5. Effect of dHSA, 8 μg/ml, on PHA induced proliferation of PBMCs from 5 controls and 4 cancer patients.

Figure 6A:
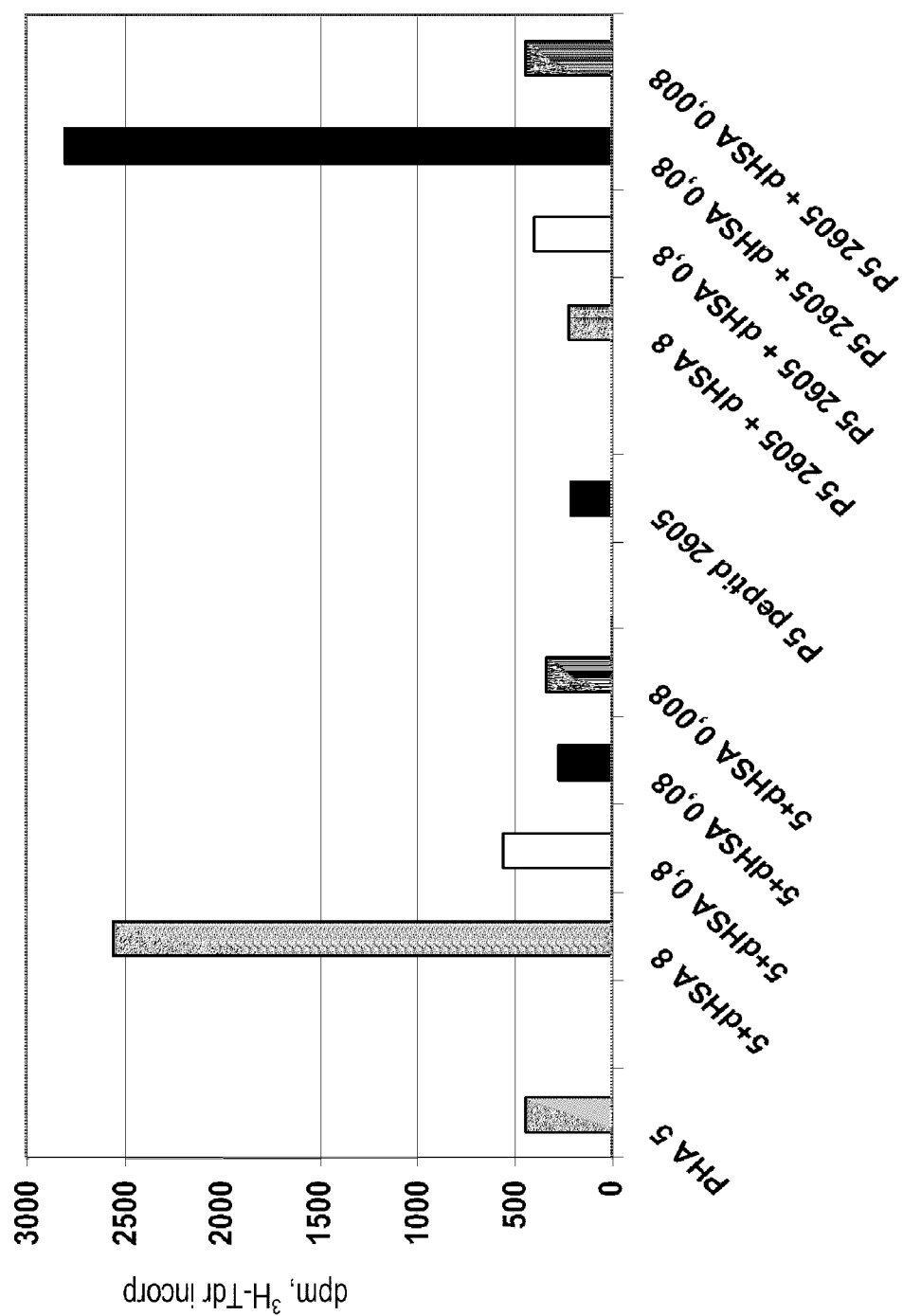
Figure 6B:
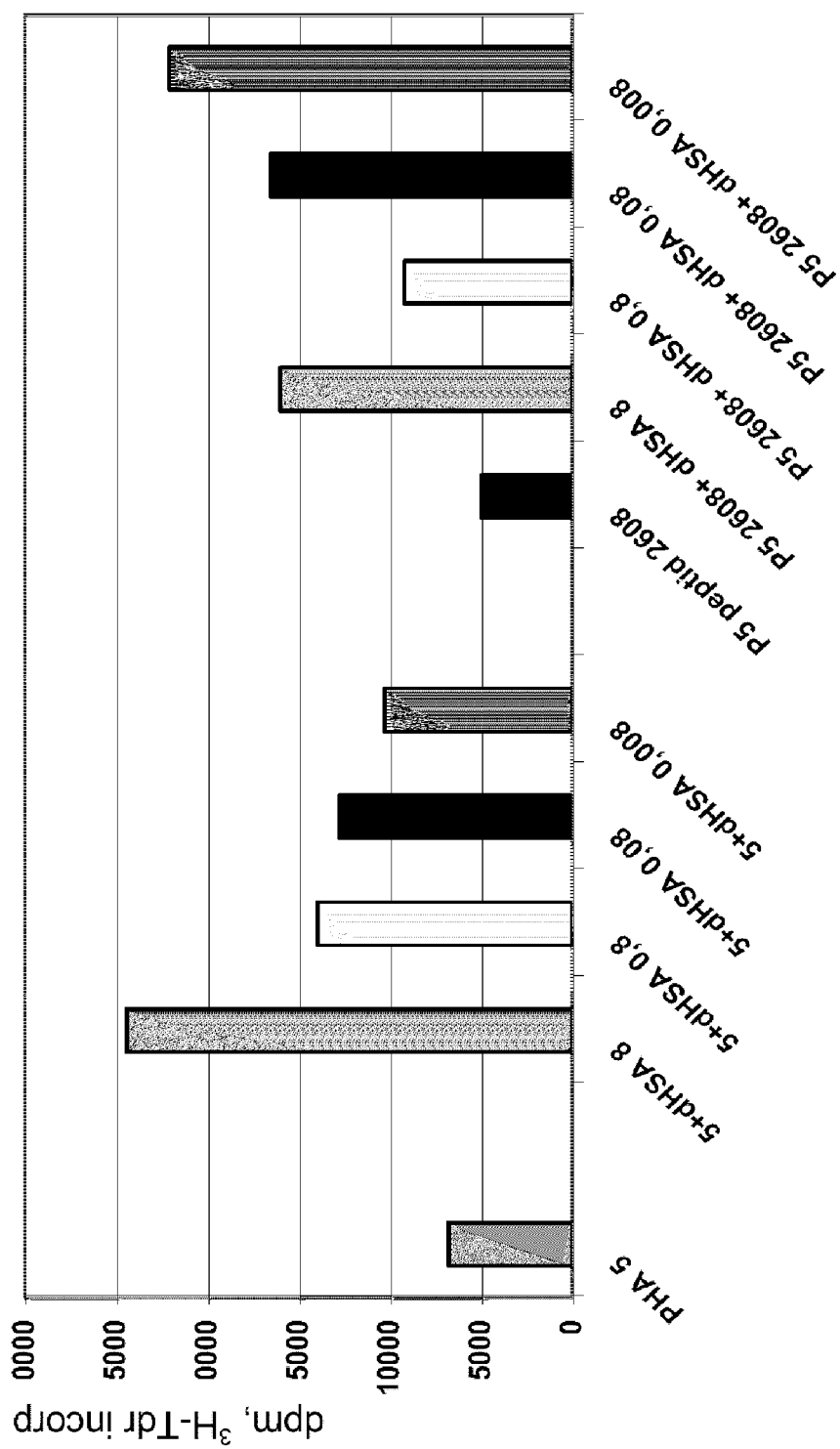

FIG. 6 A. Effect of peptide 2605 on dHSA enhanced PHA induced proliferation. The details are described in the text.

FIG. 6 B. Effect of peptide 2608 on dHSA enhanced PHA induced proliferation. The details are described in the text.

FIG. 7. Effect of albumin peptides on LPS-induced IL-6 production by PBMC from FIG. 7A a healthy donor, FIGS. 7B and 7C cancer patients with malignant melanoma. PBMC were stimulated with LPS for 24 h in the presence of the indicated peptides at 0.01 μg/ml (black bars), 0.1 μg/ml (grey bars), 1 μg/ml (white bars) or 10 μg/ml (hatched bars). The amount of IL-6 released into the culture medium was measured by ELISA. Results are expressed as percent of IL-6 released in control cultures without the addition of peptides. This was 1072 pg/ml, 997 pg/ml and 902 pg/ml in FIGS. 7A, 7B, and 7C, respectively.

FIG. 8 A-F. Effect of albumin peptides on the binding of antibodies to LFA-1 on immune cells. The monocytic cell line THP-1 (FIGS. 8A and 8B), PBMC from two healthy controls (FIGS. 8C, 8D, and 8E, 8F, respectively). Peptide 2606 was used in experiments shown in B and D and peptide 2605 was used in F.

FIG. 9. Effect of peptides on dHSA modulated PHA induced proliferation of PBMCs

Figure 10:
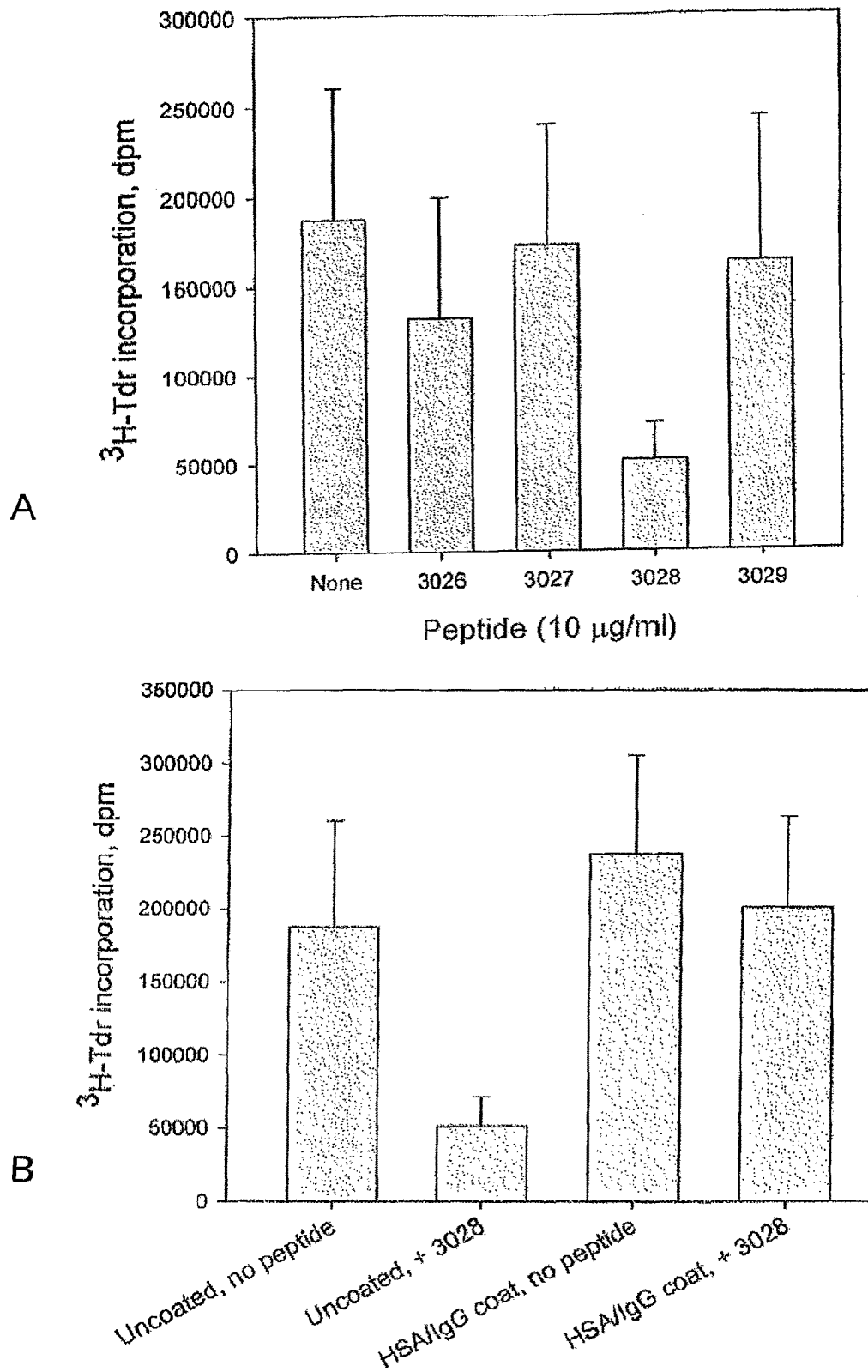

FIG. 10. Effect of the new series of peptides on IL-2 induced proliferation (A) and reversal of the inhibitory activity of peptide 3028 by Fc-receptor modulation (B).

FIG. 11. Effect of the new series of peptides on LPS induced IL-6 production by PBMCs from two healthy controls.

FIG. 12. Effect of the new series of peptides on LPS induced IL-6 production by PBMCs from three cancer patients, with malignant melanoma (MM) and with renal cell carcinoma (RCC).

Figure 13:
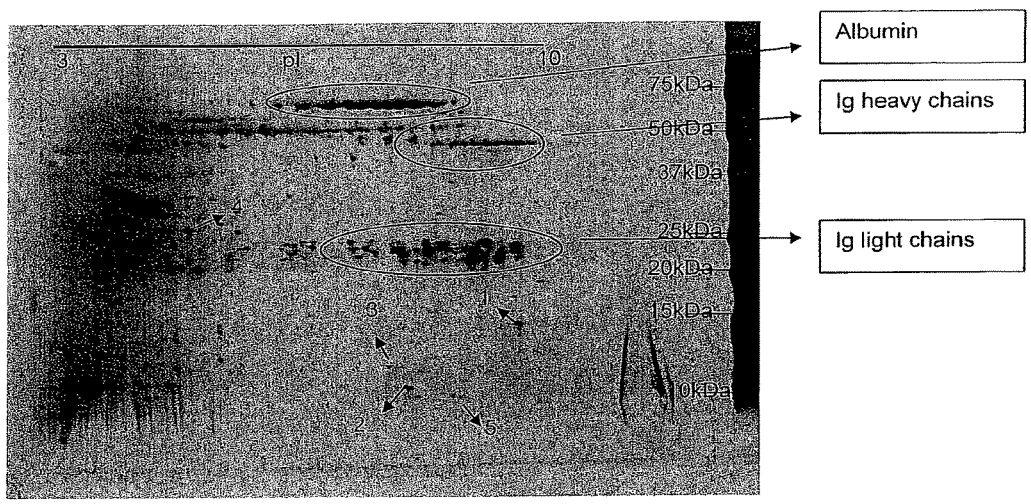

FIG. 13. 2-D gel electrophoresis of proteins from plasma after ACS affinity chromatography. The plasma was obtained from a patient with malignant melanoma.

Figure 14:
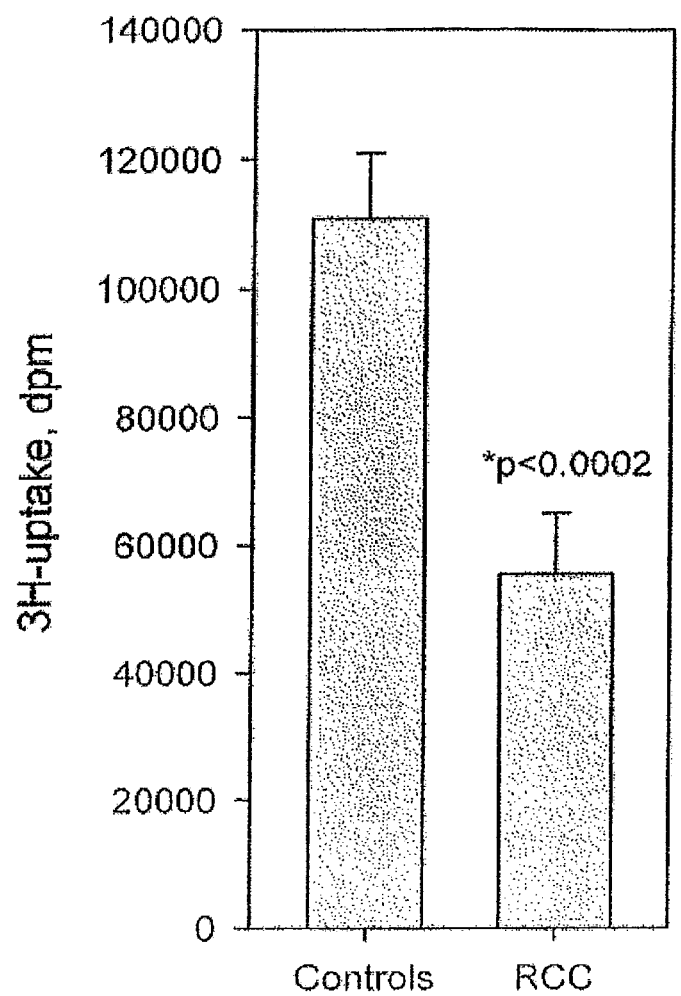

FIG. 14. IL-2 induced proliferation by PBMC from healthy controls and PBMC from renal cell carcinoma patients (RCC) cultured in 10% autologous sera.

Figure 15:
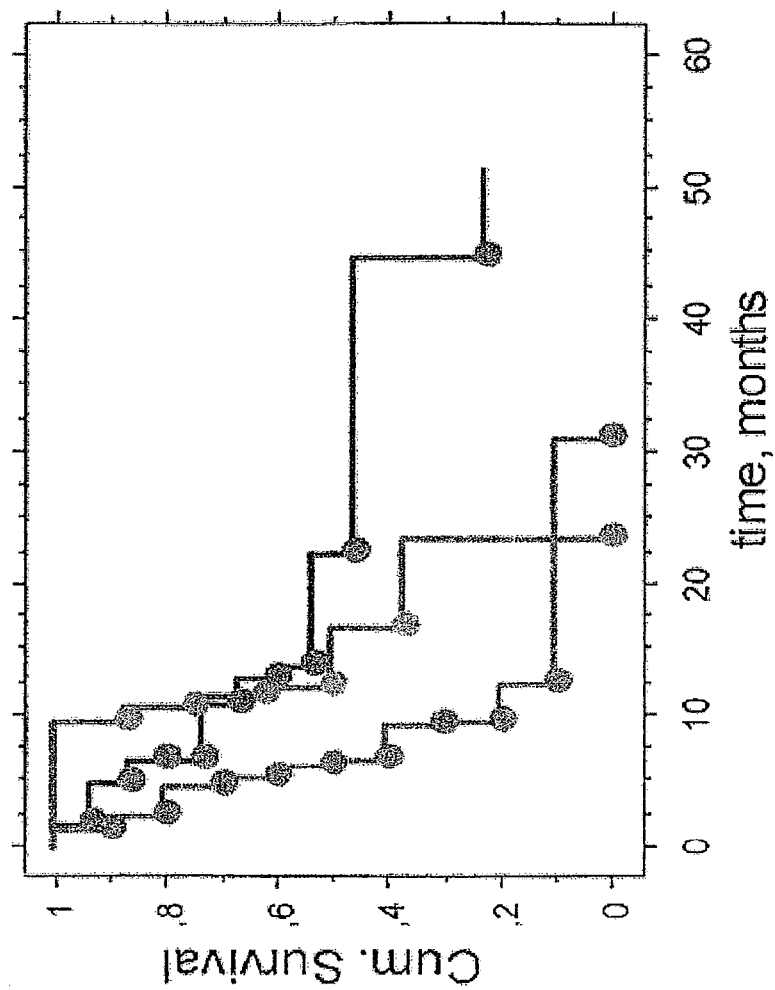

FIG. 15. A Kaplan Meyer analysis of renal cell carcinoma patients according to proliferative response to IL-2. A low proliferative rate indicates a poor survival.

Figure 16:
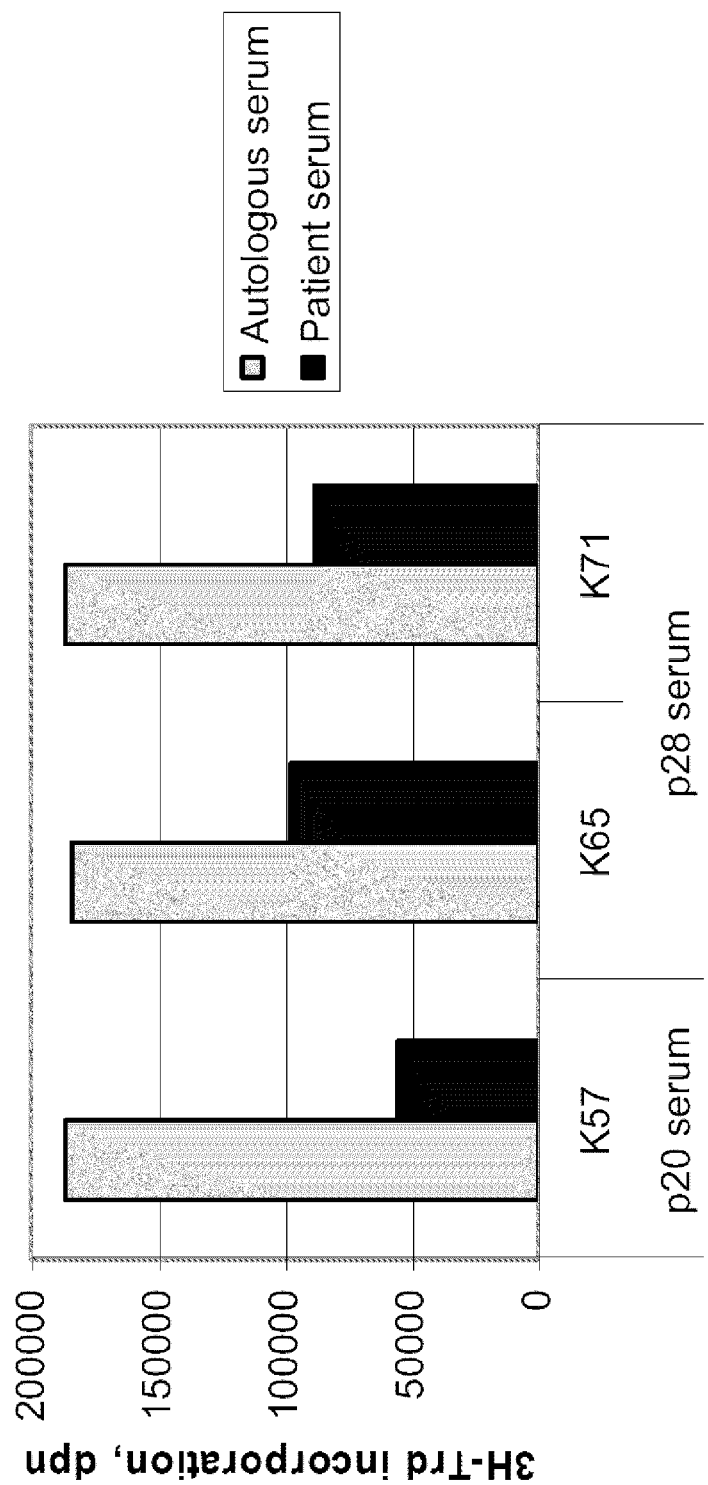

FIG. 16. Culture of PBMCs from healthy controls in sera from cancer patients known to have a suppressed response to IL-2 in the ex vivo model.

Figure 17:
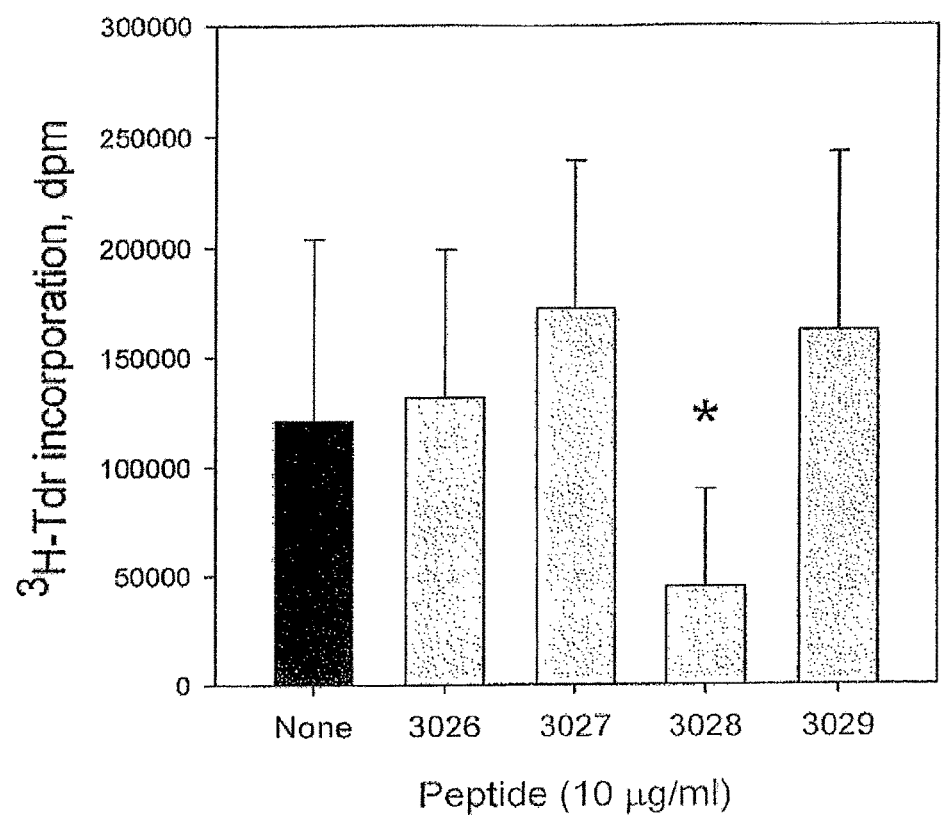

FIG. 17. Analysis of the effect of four different peptides on IL-2 induced proliferation of PBMCs from healthy controls. PBMCs were culture for 7 days in the presence of IL-2 (20 U/ml) and the peptides. Proliferation was measured as incorporation of $^3$H-thymidine during the final 18 hours. //Control PBMC, (None vs 3028, * p<0.0006, n=17) (Note, 3026, 3027, 3029 n=4 or 5).

Figure 18:
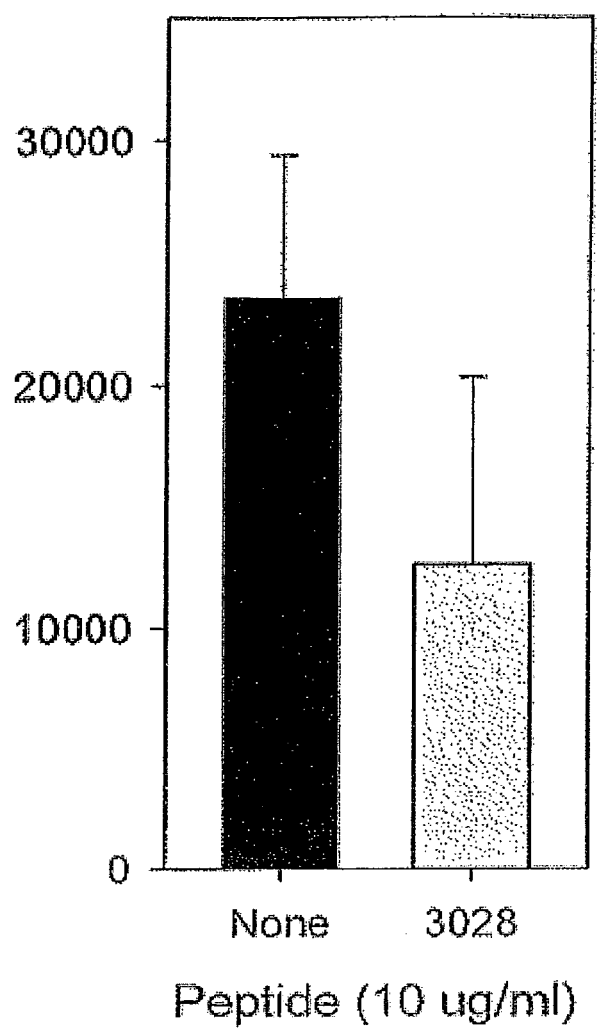

FIG. 18. Inhibition of the proliferative response to IL-2 by peptide 3028 in the human ex vivo model using cancer patient PBMCs.

Figure 19A:
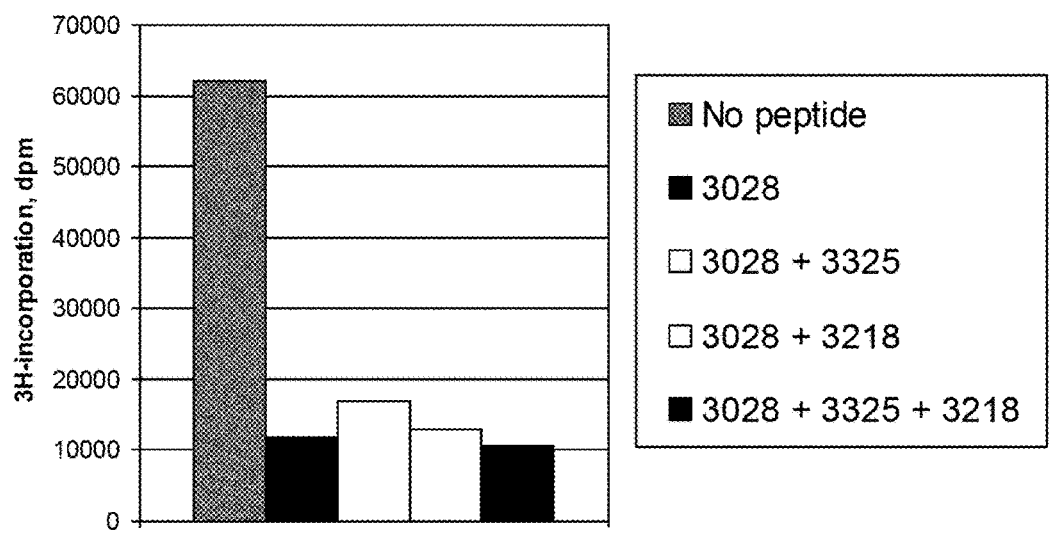
Figure 19B:
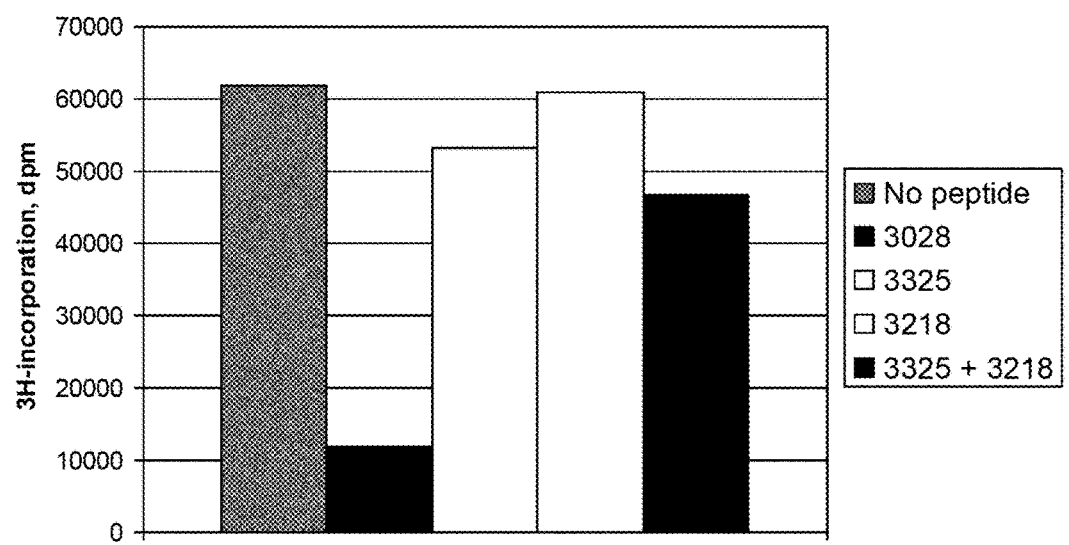

FIG. 19A. Effect of the C- (3218) and N-terminal (3325) parts of peptide 3028 on 11-2 induced proliferation in comparison with the effect of the whole/full length peptide 3028. One representative experiment is shown. FIG. 19B. The inhibitory effect of peptide 3028 on IL-2 induced proliferation is not neutralised by the C- (3218) and N-terminal (3325) parts of peptide 3028 alone or in combination.

Figure 20:
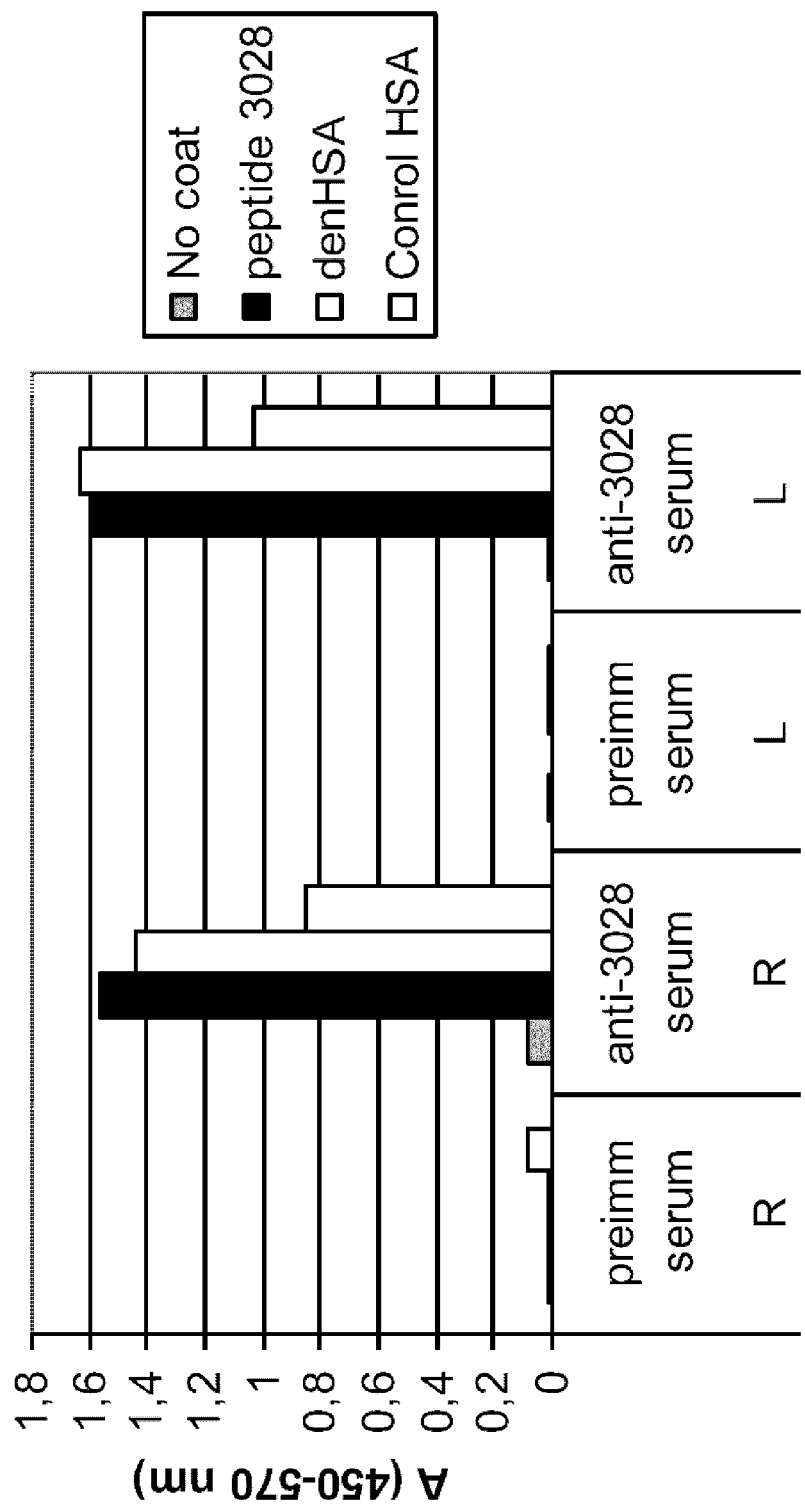

FIG. 20. Antisera, but not preimmune sera, from two rabbits immunized with the albumin peptide 3028 bind to wells coated with the 3028 peptide, denatured HSA (denHSA) and, to a lesser extent, to control treated (not denatured) HSA, which has been prepared just as the denatured HSA except for the denaturation procedure.

Figure 21:
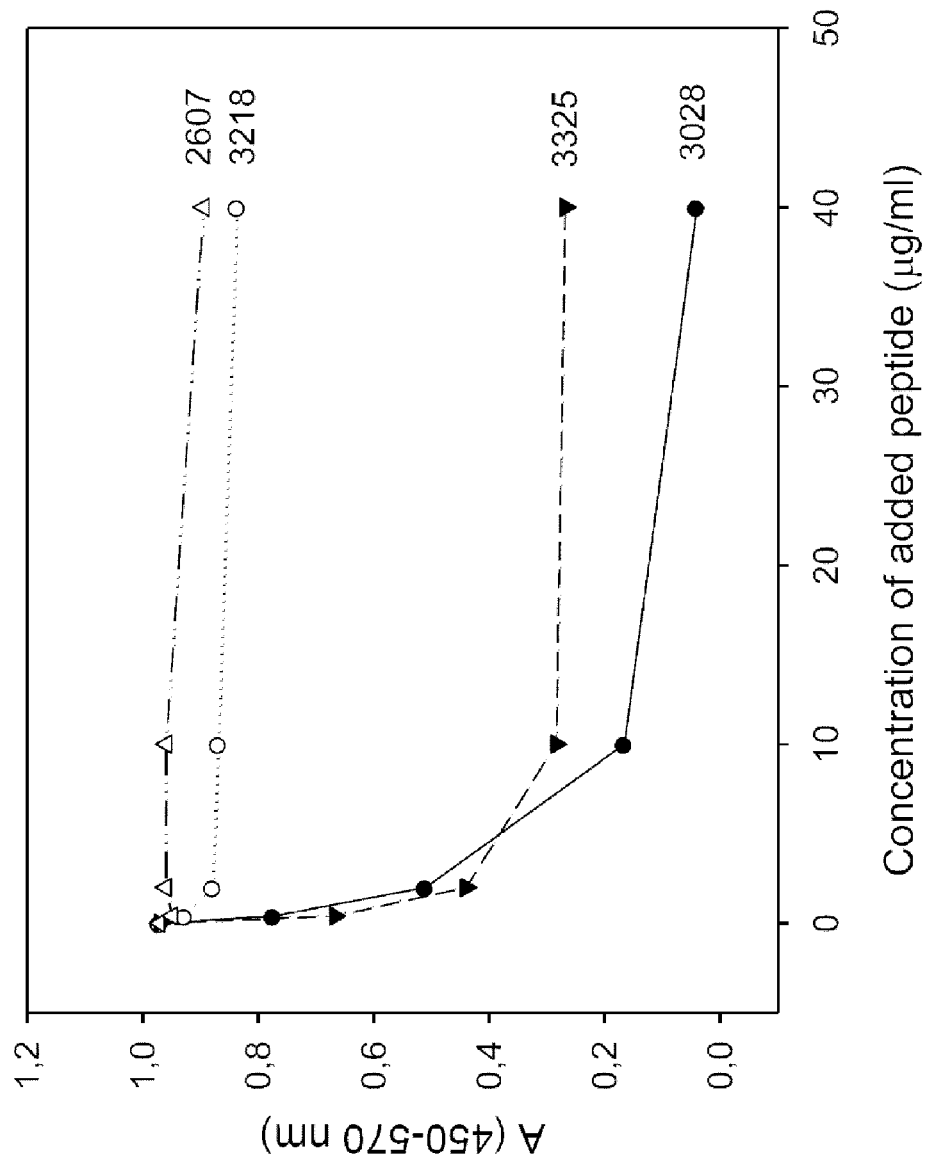

FIG. 21. Inhibition of the binding of rabbit-anti 3028 serum L to wells coated with the 3028 peptide in an ELISA by albumin peptides. Peptide 2607, containing the E5K structure, is used as a negative control.

FIG. 22. Effect of affinity purified antibodies directed against peptide 3028 on the proliferative response to IL-2 of PBMCs from immunosuppressed cancer patients and normal controls with down-regulation of immune reactivity. P21 has renal cell carcinoma and p26, p28 and p29 have malignant melanoma.

Figure 23:
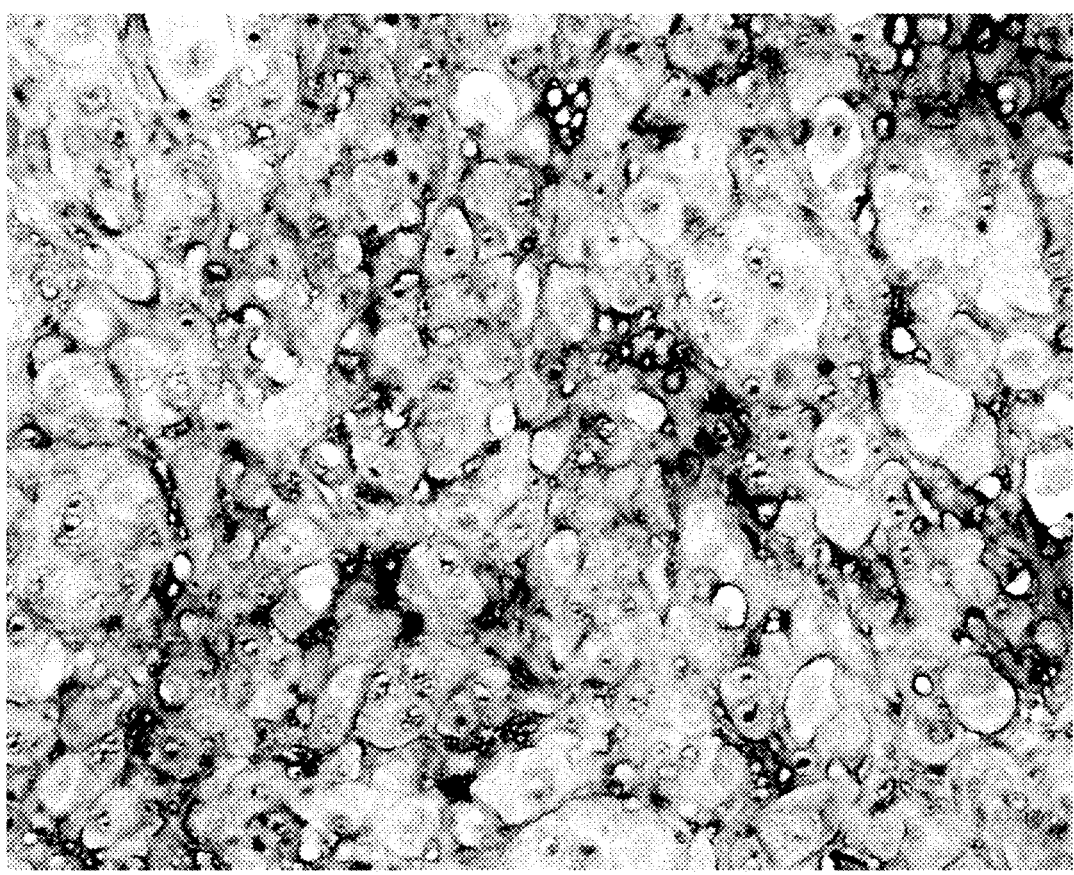

FIG. 23. Immunohistochemical staining of a malignant melanoma metastases using affinity purified rabbit antibodies directed to the 3028 epitope.

Figure 24:
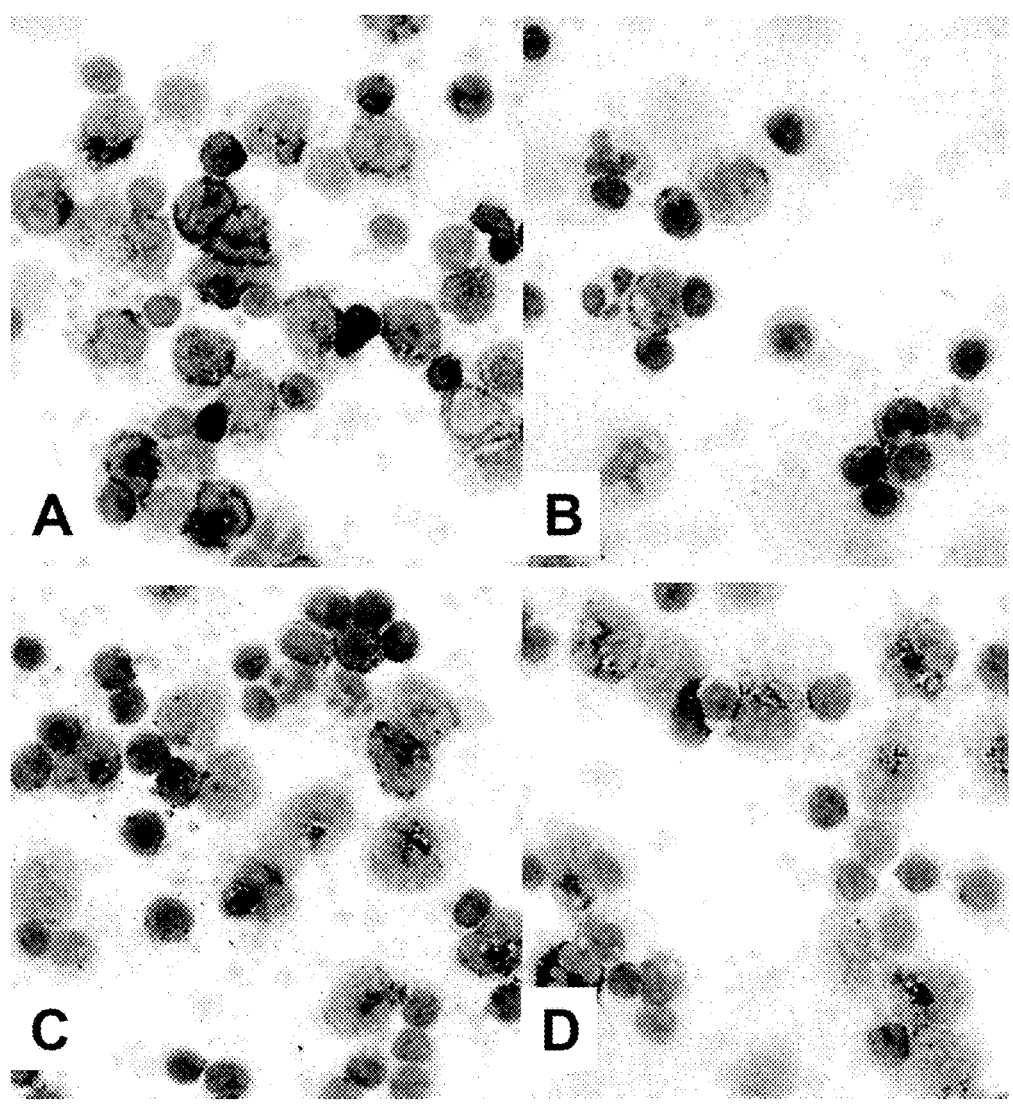

FIG. 24. Inhibition of the binding of anti-LFA-1, mab HI111, to mononuclear blood cells by 3028 peptide and fragments 3325 and 3218. A standard immunohistochemical staining procedure using acetone fixation, 10% human AB-serum for blocking, incubation with HI 111 and a secondary antibody (Ultravision, an alkaline phosphate conjugated polymer attached to Fab-fragments of goat anti-mouse Ig), followed by development with Fast Red. The slides were then mounted in Glycergel. Preincubation with peptides added to the AB serum was as follows: A. No peptide added, B. peptide 3028, C. The C-terminal part (3218), and D. The N-terminal part (3325).

Figure 25:
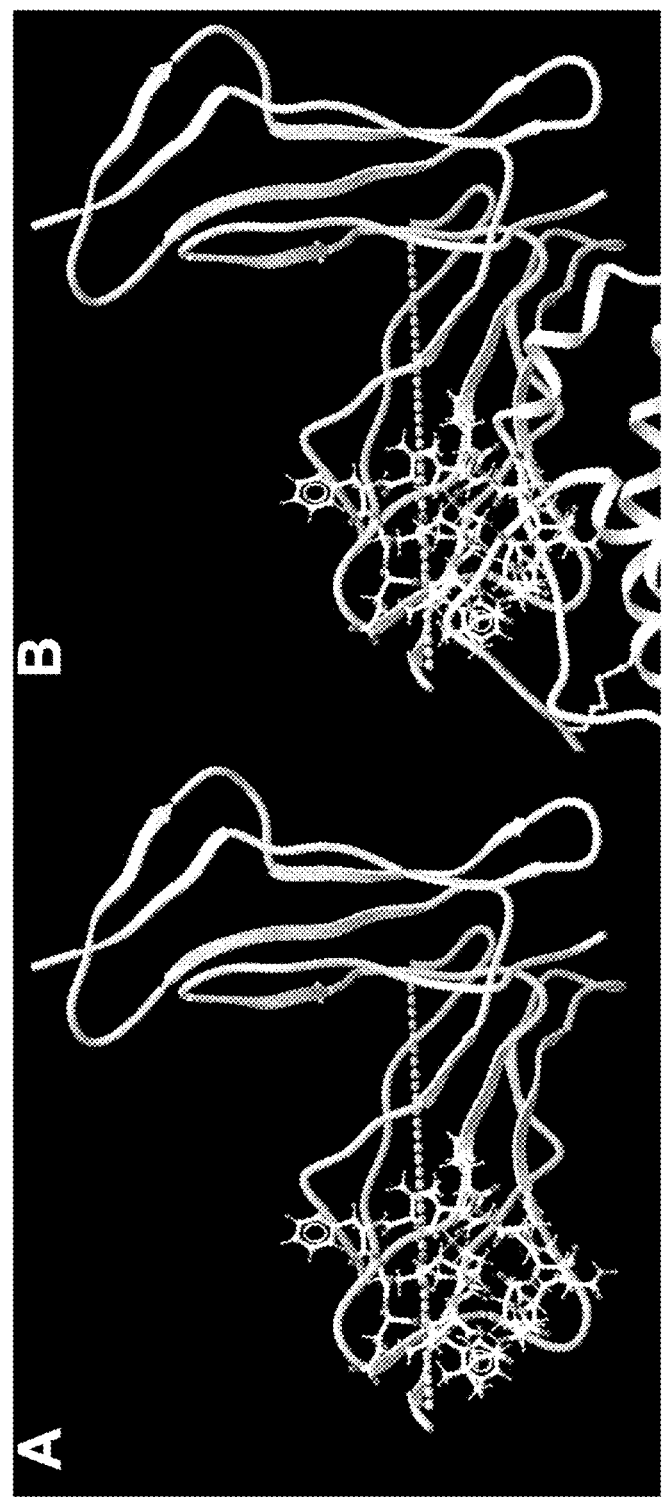

FIG. 25. Demonstration using computer assisted molecular modeling that peptide 3028 binds to CD25 at the IL-2 binding site The α-chain of the IL-2 receptor (CD25) binding peptide 3028 (A) at the IL-2 binding site (B). CD25 yellow and IL-2 blue.

FIG. 26. Difference in anti-proliferative activity of peptides 3218 an 3325, specificity of the affinity purified antibodies directed to peptide 3325 and not to peptide 3218, immunomodulatory activity these antibodies, and the effect of these peptides on the binding of the anti-LFA-1 mAb to immune cells) it can be concluded that neither of the minor peptides, 3218 or 3325, are as efficient as the complete peptide, 3028.

FIG. 27A-D. Effect of albumin peptides on cytotoxic activity of natural killer (NK) cells from healthy blood donors.

FIG. 28. Table 4A. E3-7K sequences in HSA.

FIG. 29. Table 4B. K3-7E sequences in HSA.

REFERENCE LISTING

1. Suckau D et al, PNAS, 1990, 87:9848.
2. Macht M et al, Biochemistry, 1996, 35:15633.
3. Kiselar J G and Downard K M, Anal Chem 1999, 71:1792.
4. Davis G E, Exp. Cell Res, 1992, 200; 242.
5. Doyen N et al. Mol Immunol, 1985, 22:1-10
6. Peterson N C. Advances in monoclonal antibody technology: Genetic engineering of mice, cells and immunoglobulins. ILAR Journal, 2005, 46:314-9.

The invention claimed is:

1. A method of treating a malignant tumor, the method comprising administering to a subject having a malignant tumor an effective amount of an antibody or fragment thereof with specificity against a peptide consisting of the amino acid sequence set forth in SEQ ID NO: 80.

2. The method of claim 1, wherein said antibody or fragment thereof is humanized.

3. The method of claim 1, wherein said antibody is a full-length antibody.

4. The method of claim 1, wherein said antibody is a monoclonal antibody.

5. The method of claim 1, wherein said malignant tumor is selected from the group consisting of: malignant melanoma, renal cell carcinoma and colorectal cancer.

* * * * *

```
                              SEQUENCE LISTING

<160> NUMBER OF SEQ ID NOS: 195

<210> SEQ ID NO 1
    <211> LENGTH: 5
    <212> TYPE: PRT
    <213> ORGANISM: HOMO SAPIENS

<400> SEQUENCE: 1

Glu Glu Asn Phe Lys
     1               5

<210> SEQ ID NO 2
    <211> LENGTH: 5
    <212> TYPE: PRT
    <213> ORGANISM: HOMO SAPIENS

<400> SEQUENCE: 2

Glu Asp His Val Lys
     1               5

<210> SEQ ID NO 3
    <211> LENGTH: 5
    <212> TYPE: PRT
    <213> ORGANISM: HOMO SAPIENS

<400> SEQUENCE: 3

Glu Asn Cys Asp Lys
     1               5

<210> SEQ ID NO 4
    <211> LENGTH: 5
    <212> TYPE: PRT
    <213> ORGANISM: HOMO SAPIENS

<400> SEQUENCE: 4

Glu Thr Phe Leu Lys
     1               5

<210> SEQ ID NO 5
    <211> LENGTH: 5
    <212> TYPE: PRT
    <213> ORGANISM: HOMO SAPIENS

<400> SEQUENCE: 5

Glu Arg Ala Phe Lys
     1               5

<210> SEQ ID NO 6
    <211> LENGTH: 5
    <212> TYPE: PRT
    <213> ORGANISM: HOMO SAPIENS
```

```
<400> SEQUENCE: 6

Glu Cys Cys Glu Lys
1               5

<210> SEQ ID NO 7
<211> LENGTH: 5
<212> TYPE: PRT
<213> ORGANISM: HOMO SAPIENS

<400> SEQUENCE: 7

Glu Cys Tyr Ala Lys
1               5

<210> SEQ ID NO 8
<211> LENGTH: 5
<212> TYPE: PRT
<213> ORGANISM: HOMO SAPIENS

<400> SEQUENCE: 8

Glu Arg Gln Ile Lys
1               5

<210> SEQ ID NO 9
<211> LENGTH: 5
<212> TYPE: PRT
<213> ORGANISM: HOMO SAPIENS

<400> SEQUENCE: 9

Glu Lys Cys Cys Lys
1               5

<210> SEQ ID NO 10
<211> LENGTH: 5
<212> TYPE: PRT
<213> ORGANISM: HOMO SAPIENS

<400> SEQUENCE: 10

Glu Glu Gly Lys Lys
1               5

<210> SEQ ID NO 11
<211> LENGTH: 6
<212> TYPE: PRT
<213> ORGANISM: HOMO SAPIENS

<400> SEQUENCE: 11

Glu Glu Thr Phe Leu Lys
1               5

<210> SEQ ID NO 12
<211> LENGTH: 6
<212> TYPE: PRT
<213> ORGANISM: HOMO SAPIENS

<400> SEQUENCE: 12

Glu Thr Phe Leu Lys Lys
1               5

<210> SEQ ID NO 13
<211> LENGTH: 6
<212> TYPE: PRT
<213> ORGANISM: HOMO SAPIENS

<400> SEQUENCE: 13
```

```
Glu Thr Thr Leu Glu Lys
  1               5

<210> SEQ ID NO 14
<211> LENGTH: 6
<212> TYPE: PRT
<213> ORGANISM: HOMO SAPIENS

<400> SEQUENCE: 14

Glu Thr Tyr Val Pro Lys
  1               5

<210> SEQ ID NO 15
<211> LENGTH: 6
<212> TYPE: PRT
<213> ORGANISM: HOMO SAPIENS

<400> SEQUENCE: 15

Glu Arg Gln Ile Lys Lys
  1               5

<210> SEQ ID NO 16
<211> LENGTH: 6
<212> TYPE: PRT
<213> ORGANISM: HOMO SAPIENS

<400> SEQUENCE: 16

Glu Leu Val Lys His Lys
  1               5

<210> SEQ ID NO 17
<211> LENGTH: 7
<212> TYPE: PRT
<213> ORGANISM: HOMO SAPIENS

<400> SEQUENCE: 17

Glu Val Ala His Arg Phe Lys
  1               5

<210> SEQ ID NO 18
<211> LENGTH: 7
<212> TYPE: PRT
<213> ORGANISM: HOMO SAPIENS

<400> SEQUENCE: 18

Glu Val Thr Glu Phe Ala Lys
  1               5

<210> SEQ ID NO 19
<211> LENGTH: 7
<212> TYPE: PRT
<213> ORGANISM: HOMO SAPIENS

<400> SEQUENCE: 19

Glu Cys Phe Leu Gln His Lys
  1               5

<210> SEQ ID NO 20
<211> LENGTH: 7
<212> TYPE: PRT
<213> ORGANISM: HOMO SAPIENS

<400> SEQUENCE: 20

Glu Glu Thr Phe Leu Lys Lys
```

1               5

<210> SEQ ID NO 21
<211> LENGTH: 7
<212> TYPE: PRT
<213> ORGANISM: HOMO SAPIENS

<400> SEQUENCE: 21

Glu Leu Leu Phe Phe Ala Lys
1               5

<210> SEQ ID NO 22
<211> LENGTH: 7
<212> TYPE: PRT
<213> ORGANISM: HOMO SAPIENS

<400> SEQUENCE: 22

Glu Leu Arg Asp Glu Gly Lys
1               5

<210> SEQ ID NO 23
<211> LENGTH: 7
<212> TYPE: PRT
<213> ORGANISM: HOMO SAPIENS

<400> SEQUENCE: 23

Glu Phe Ala Gly Val Ser Lys
1               5

<210> SEQ ID NO 24
<211> LENGTH: 7
<212> TYPE: PRT
<213> ORGANISM: HOMO SAPIENS

<400> SEQUENCE: 24

Glu Lys Pro Leu Leu Glu Lys
1               5

<210> SEQ ID NO 25
<211> LENGTH: 7
<212> TYPE: PRT
<213> ORGANISM: HOMO SAPIENS

<400> SEQUENCE: 25

Glu Ser Lys Asp Val Cys Lys
1               5

<210> SEQ ID NO 26
<211> LENGTH: 7
<212> TYPE: PRT
<213> ORGANISM: HOMO SAPIENS

<400> SEQUENCE: 26

Glu Pro Gln Asn Leu Ile Lys
1               5

<210> SEQ ID NO 27
<211> LENGTH: 7
<212> TYPE: PRT
<213> ORGANISM: HOMO SAPIENS

<400> SEQUENCE: 27

Glu Gln Leu Gly Glu Tyr Lys
1               5

<210> SEQ ID NO 28
<211> LENGTH: 7
<212> TYPE: PRT
<213> ORGANISM: HOMO SAPIENS

<400> SEQUENCE: 28

Glu Lys Glu Arg Gln Ile Lys
1               5

<210> SEQ ID NO 29
<211> LENGTH: 8
<212> TYPE: PRT
<213> ORGANISM: HOMO SAPIENS

<400> SEQUENCE: 29

Glu Ser Ala Glu Asn Cys Asp Lys
1               5

<210> SEQ ID NO 30
<211> LENGTH: 8
<212> TYPE: PRT
<213> ORGANISM: HOMO SAPIENS

<400> SEQUENCE: 30

Glu Met Ala Asp Cys Cys Ala Lys
1               5

<210> SEQ ID NO 31
<211> LENGTH: 8
<212> TYPE: PRT
<213> ORGANISM: HOMO SAPIENS

<400> SEQUENCE: 31

Glu Cys Cys Gln Ala Ala Asp Lys
1               5

<210> SEQ ID NO 32
<211> LENGTH: 8
<212> TYPE: PRT
<213> ORGANISM: HOMO SAPIENS

<400> SEQUENCE: 32

Glu Gly Lys Ala Ser Ser Ala Lys
1               5

<210> SEQ ID NO 33
<211> LENGTH: 8
<212> TYPE: PRT
<213> ORGANISM: HOMO SAPIENS

<400> SEQUENCE: 33

Glu Glu Pro Gln Asn Leu Ile Lys
1               5

<210> SEQ ID NO 34
<211> LENGTH: 8
<212> TYPE: PRT
<213> ORGANISM: HOMO SAPIENS

<400> SEQUENCE: 34

Glu Val Ser Arg Asn Leu Gly Lys
1               5

<210> SEQ ID NO 35

```
<211> LENGTH: 8
<212> TYPE: PRT
<213> ORGANISM: HOMO SAPIENS

<400> SEQUENCE: 35

Glu Lys Glu Arg Gln Ile Lys Lys
1               5

<210> SEQ ID NO 36
<211> LENGTH: 8
<212> TYPE: PRT
<213> ORGANISM: HOMO SAPIENS

<400> SEQUENCE: 36

Glu Leu Val Lys His Lys Pro Lys
1               5

<210> SEQ ID NO 37
<211> LENGTH: 9
<212> TYPE: PRT
<213> ORGANISM: HOMO SAPIENS

<400> SEQUENCE: 37

Glu Asn Gln Asp Ser Ile Ser Ser Lys
1               5

<210> SEQ ID NO 38
<211> LENGTH: 9
<212> TYPE: PRT
<213> ORGANISM: HOMO SAPIENS

<400> SEQUENCE: 38

Glu Lys Cys Cys Lys Ala Asp Asp Lys
1               5

<210> SEQ ID NO 39
<211> LENGTH: 9
<212> TYPE: PRT
<213> ORGANISM: HOMO SAPIENS

<400> SEQUENCE: 39

Glu Thr Cys Phe Ala Glu Glu Gly Lys
1               5

<210> SEQ ID NO 40
<211> LENGTH: 5
<212> TYPE: PRT
<213> ORGANISM: HOMO SAPIENS

<400> SEQUENCE: 40

Lys Asp Leu Gly Glu
1               5

<210> SEQ ID NO 41
<211> LENGTH: 5
<212> TYPE: PRT
<213> ORGANISM: HOMO SAPIENS

<400> SEQUENCE: 41

Lys Leu Val Asn Glu
1               5

<210> SEQ ID NO 42
<211> LENGTH: 5
<212> TYPE: PRT
```

<213> ORGANISM: HOMO SAPIENS

<400> SEQUENCE: 42

Lys Gln Glu Pro Glu
1               5

<210> SEQ ID NO 43
<211> LENGTH: 5
<212> TYPE: PRT
<213> ORGANISM: HOMO SAPIENS

<400> SEQUENCE: 43

Lys Tyr Leu Tyr Glu
1               5

<210> SEQ ID NO 44
<211> LENGTH: 5
<212> TYPE: PRT
<213> ORGANISM: HOMO SAPIENS

<400> SEQUENCE: 44

Lys Val His Thr Glu
1               5

<210> SEQ ID NO 45
<211> LENGTH: 5
<212> TYPE: PRT
<213> ORGANISM: HOMO SAPIENS

<400> SEQUENCE: 45

Lys Tyr Ile Cys Glu
1               5

<210> SEQ ID NO 46
<211> LENGTH: 5
<212> TYPE: PRT
<213> ORGANISM: HOMO SAPIENS

<400> SEQUENCE: 46

Lys Glu Cys Cys Glu
1               5

<210> SEQ ID NO 47
<211> LENGTH: 5
<212> TYPE: PRT
<213> ORGANISM: HOMO SAPIENS

<400> SEQUENCE: 47

Lys Pro Leu Leu Glu
1               5

<210> SEQ ID NO 48
<211> LENGTH: 5
<212> TYPE: PRT
<213> ORGANISM: HOMO SAPIENS

<400> SEQUENCE: 48

Lys Asn Tyr Ala Glu
1               5

<210> SEQ ID NO 49
<211> LENGTH: 5
<212> TYPE: PRT
<213> ORGANISM: HOMO SAPIENS

<400> SEQUENCE: 49

Lys Val Phe Asp Glu
 1               5

<210> SEQ ID NO 50
<211> LENGTH: 5
<212> TYPE: PRT
<213> ORGANISM: HOMO SAPIENS

<400> SEQUENCE: 50

Lys Pro Leu Val Glu
 1               5

<210> SEQ ID NO 51
<211> LENGTH: 5
<212> TYPE: PRT
<213> ORGANISM: HOMO SAPIENS

<400> SEQUENCE: 51

Lys Gln Asn Cys Glu
 1               5

<210> SEQ ID NO 52
<211> LENGTH: 5
<212> TYPE: PRT
<213> ORGANISM: HOMO SAPIENS

<400> SEQUENCE: 52

Lys Cys Cys Thr Glu
 1               5

<210> SEQ ID NO 53
<211> LENGTH: 5
<212> TYPE: PRT
<213> ORGANISM: HOMO SAPIENS

<400> SEQUENCE: 53

Lys Ala Thr Lys Glu
 1               5

<210> SEQ ID NO 54
<211> LENGTH: 6
<212> TYPE: PRT
<213> ORGANISM: HOMO SAPIENS

<400> SEQUENCE: 54

Lys Asp Leu Gly Glu Glu
 1               5

<210> SEQ ID NO 55
<211> LENGTH: 6
<212> TYPE: PRT
<213> ORGANISM: HOMO SAPIENS

<400> SEQUENCE: 55

Lys Lys Tyr Leu Tyr Glu
 1               5

<210> SEQ ID NO 56
<211> LENGTH: 6
<212> TYPE: PRT
<213> ORGANISM: HOMO SAPIENS

<400> SEQUENCE: 56

Lys Ala Ala Phe Thr Glu
1               5

<210> SEQ ID NO 57
<211> LENGTH: 6
<212> TYPE: PRT
<213> ORGANISM: HOMO SAPIENS

<400> SEQUENCE: 57

Lys Ala Glu Phe Ala Glu
1               5

<210> SEQ ID NO 58
<211> LENGTH: 6
<212> TYPE: PRT
<213> ORGANISM: HOMO SAPIENS

<400> SEQUENCE: 58

Lys Pro Leu Val Glu Glu
1               5

<210> SEQ ID NO 59
<211> LENGTH: 6
<212> TYPE: PRT
<213> ORGANISM: HOMO SAPIENS

<400> SEQUENCE: 59

Lys Glu Phe Asn Ala Glu
1               5

<210> SEQ ID NO 60
<211> LENGTH: 6
<212> TYPE: PRT
<213> ORGANISM: HOMO SAPIENS

<400> SEQUENCE: 60

Lys Ala Asp Asp Lys Glu
1               5

<210> SEQ ID NO 61
<211> LENGTH: 7
<212> TYPE: PRT
<213> ORGANISM: HOMO SAPIENS

<400> SEQUENCE: 61

Lys Thr Cys Val Ala Asp Glu
1               5

<210> SEQ ID NO 62
<211> LENGTH: 7
<212> TYPE: PRT
<213> ORGANISM: HOMO SAPIENS

<400> SEQUENCE: 62

Lys Leu Lys Glu Cys Cys Glu
1               5

<210> SEQ ID NO 63
<211> LENGTH: 7
<212> TYPE: PRT
<213> ORGANISM: HOMO SAPIENS

<400> SEQUENCE: 63

Lys Ser His Cys Ile Ala Glu
1               5

<210> SEQ ID NO 64
<211> LENGTH: 7
<212> TYPE: PRT
<213> ORGANISM: HOMO SAPIENS

<400> SEQUENCE: 64

Lys Cys Cys Lys His Pro Glu
1               5

<210> SEQ ID NO 65
<211> LENGTH: 7
<212> TYPE: PRT
<213> ORGANISM: HOMO SAPIENS

<400> SEQUENCE: 65

Lys Arg Met Pro Cys Ala Glu
1               5

<210> SEQ ID NO 66
<211> LENGTH: 7
<212> TYPE: PRT
<213> ORGANISM: HOMO SAPIENS

<400> SEQUENCE: 66

Lys Gln Thr Ala Leu Val Glu
1               5

<210> SEQ ID NO 67
<211> LENGTH: 7
<212> TYPE: PRT
<213> ORGANISM: HOMO SAPIENS

<400> SEQUENCE: 67

Lys Pro Lys Ala Thr Lys Glu
1               5

<210> SEQ ID NO 68
<211> LENGTH: 7
<212> TYPE: PRT
<213> ORGANISM: HOMO SAPIENS

<400> SEQUENCE: 68

Lys Glu Thr Cys Phe Ala Glu
1               5

<210> SEQ ID NO 69
<211> LENGTH: 8
<212> TYPE: PRT
<213> ORGANISM: HOMO SAPIENS

<400> SEQUENCE: 69

Lys Leu Val Asn Glu Val Thr Glu
1               5

<210> SEQ ID NO 70
<211> LENGTH: 8
<212> TYPE: PRT
<213> ORGANISM: HOMO SAPIENS

<400> SEQUENCE: 70

Lys Gln Glu Pro Glu Arg Asn Glu
1               5

```
<210> SEQ ID NO 71
<211> LENGTH: 8
<212> TYPE: PRT
<213> ORGANISM: HOMO SAPIENS

<400> SEQUENCE: 71

Lys Leu Asp Glu Leu Arg Asp Glu
1               5

<210> SEQ ID NO 72
<211> LENGTH: 8
<212> TYPE: PRT
<213> ORGANISM: HOMO SAPIENS

<400> SEQUENCE: 72

Lys Thr Tyr Glu Thr Thr Leu Glu
1               5

<210> SEQ ID NO 73
<211> LENGTH: 8
<212> TYPE: PRT
<213> ORGANISM: HOMO SAPIENS

<400> SEQUENCE: 73

Lys Gln Asn Cys Glu Leu Phe Glu
1               5

<210> SEQ ID NO 74
<211> LENGTH: 8
<212> TYPE: PRT
<213> ORGANISM: HOMO SAPIENS

<400> SEQUENCE: 74

Lys Lys Gln Thr Ala Leu Val Glu
1               5

<210> SEQ ID NO 75
<211> LENGTH: 8
<212> TYPE: PRT
<213> ORGANISM: HOMO SAPIENS

<400> SEQUENCE: 75

Lys Glu Thr Cys Phe Ala Glu Glu
1               5

<210> SEQ ID NO 76
<211> LENGTH: 9
<212> TYPE: PRT
<213> ORGANISM: HOMO SAPIENS

<400> SEQUENCE: 76

Lys Arg Tyr Lys Ala Ala Phe Thr Glu
1               5

<210> SEQ ID NO 77
<211> LENGTH: 9
<212> TYPE: PRT
<213> ORGANISM: HOMO SAPIENS

<400> SEQUENCE: 77

Lys Asp Val Cys Lys Asn Tyr Ala Glu
1               5

<210> SEQ ID NO 78
<211> LENGTH: 9
```

```
<212> TYPE: PRT
<213> ORGANISM: HOMO SAPIENS

<400> SEQUENCE: 78

Lys His Lys Pro Lys Ala Thr Lys Glu
1               5

<210> SEQ ID NO 79
<211> LENGTH: 9
<212> TYPE: PRT
<213> ORGANISM: HOMO SAPIENS

<400> SEQUENCE: 79

Glu Lys Asp Asp Ala Lys Cys Cys Lys
1               5

<210> SEQ ID NO 80
<211> LENGTH: 17
<212> TYPE: PRT
<213> ORGANISM: HOMO SAPIENS

<400> SEQUENCE: 80

Val Phe Asp Glu Phe Lys Pro Leu Val Glu Glu Pro Gln Asn Leu Ile
1               5                   10                  15

Lys

<210> SEQ ID NO 81
<211> LENGTH: 10
<212> TYPE: PRT
<213> ORGANISM: HOMO SAPIENS

<400> SEQUENCE: 81

Val Phe Asp Glu Phe Lys Pro Leu Val Glu
1               5                   10

<210> SEQ ID NO 82
<211> LENGTH: 10
<212> TYPE: PRT
<213> ORGANISM: HOMO SAPIENS

<400> SEQUENCE: 82

Leu Val Asn Glu Val Thr Glu Phe Ala Lys
1               5                   10

<210> SEQ ID NO 83
<211> LENGTH: 27
<212> TYPE: PRT
<213> ORGANISM: HOMO SAPIENS

<400> SEQUENCE: 83

Cys Tyr Ala Lys Val Phe Asp Glu Phe Lys Pro Leu Val Glu Glu Pro
1               5                   10                  15

Gln Asn Leu Ile Lys Gln Asn Cys Glu Leu Phe
            20                  25

<210> SEQ ID NO 84
<211> LENGTH: 9
<212> TYPE: PRT
<213> ORGANISM: HOMO SAPIENS

<400> SEQUENCE: 84

Ser Leu His Thr Leu Phe Gly Asp Lys
1               5
```

<210> SEQ ID NO 85
<211> LENGTH: 8
<212> TYPE: PRT
<213> ORGANISM: HOMO SAPIENS

<400> SEQUENCE: 85

Leu Cys Thr Val Ala Thr Leu Arg
 1               5

<210> SEQ ID NO 86
<211> LENGTH: 12
<212> TYPE: PRT
<213> ORGANISM: HOMO SAPIENS

<400> SEQUENCE: 86

Glu Thr Tyr Gly Glu Met Ala Asp Cys Cys Ala Lys
 1               5                  10

<210> SEQ ID NO 87
<211> LENGTH: 7
<212> TYPE: PRT
<213> ORGANISM: HOMO SAPIENS

<400> SEQUENCE: 87

Tyr Leu Tyr Glu Ile Ala Arg
 1               5

<210> SEQ ID NO 88
<211> LENGTH: 9
<212> TYPE: PRT
<213> ORGANISM: HOMO SAPIENS

<400> SEQUENCE: 88

Leu Asp Glu Leu Arg Asp Glu Gly Lys
 1               5

<210> SEQ ID NO 89
<211> LENGTH: 12
<212> TYPE: PRT
<213> ORGANISM: HOMO SAPIENS

<400> SEQUENCE: 89

Tyr Ile Cys Glu Asn Gln Asp Ser Ile Ser Ser Lys
 1               5                  10

<210> SEQ ID NO 90
<211> LENGTH: 12
<212> TYPE: PRT
<213> ORGANISM: HOMO SAPIENS

<400> SEQUENCE: 90

Leu Lys Glu Cys Cys Glu Lys Pro Leu Leu Glu Lys
 1               5                  10

<210> SEQ ID NO 91
<211> LENGTH: 11
<212> TYPE: PRT
<213> ORGANISM: HOMO SAPIENS

<400> SEQUENCE: 91

His Pro Asp Tyr Ser Val Val Leu Leu Leu Arg
 1               5                  10

<210> SEQ ID NO 92

```
<211> LENGTH: 13
<212> TYPE: PRT
<213> ORGANISM: HOMO SAPIENS

<400> SEQUENCE: 92

Cys Cys Ala Ala Ala Asp Pro His Glu Cys Tyr Ala Lys
1               5                   10

<210> SEQ ID NO 93
<211> LENGTH: 13
<212> TYPE: PRT
<213> ORGANISM: HOMO SAPIENS

<400> SEQUENCE: 93

Gln Asn Cys Glu Leu Phe Glu Gln Leu Gly Glu Tyr Lys
1               5                   10

<210> SEQ ID NO 94
<211> LENGTH: 8
<212> TYPE: PRT
<213> ORGANISM: HOMO SAPIENS

<400> SEQUENCE: 94

Phe Gln Asn Ala Leu Leu Val Arg
1               5

<210> SEQ ID NO 95
<211> LENGTH: 9
<212> TYPE: PRT
<213> ORGANISM: HOMO SAPIENS

<400> SEQUENCE: 95

Cys Cys Thr Glu Ser Leu Val Asn Arg
1               5

<210> SEQ ID NO 96
<211> LENGTH: 12
<212> TYPE: PRT
<213> ORGANISM: HOMO SAPIENS

<400> SEQUENCE: 96

Ala Val Met Asp Asp Phe Ala Ala Phe Val Glu Lys
1               5                   10

<210> SEQ ID NO 97
<211> LENGTH: 7
<212> TYPE: PRT
<213> ORGANISM: HOMO SAPIENS

<400> SEQUENCE: 97

Leu Ser Gln Arg Phe Pro Lys
1               5

<210> SEQ ID NO 98
<211> LENGTH: 7
<212> TYPE: PRT
<213> ORGANISM: HOMO SAPIENS

<400> SEQUENCE: 98

Tyr Leu Tyr Glu Ile Ala Arg
1               5

<210> SEQ ID NO 99
<211> LENGTH: 8
<212> TYPE: PRT
```

-continued

```
<213> ORGANISM: HOMO SAPIENS

<400> SEQUENCE: 99

Leu Cys Thr Val Ala Thr Leu Arg
1               5

<210> SEQ ID NO 100
<211> LENGTH: 8
<212> TYPE: PRT
<213> ORGANISM: HOMO SAPIENS

<400> SEQUENCE: 100

Asp Asp Asn Pro Asn Leu Pro Arg
1               5

<210> SEQ ID NO 101
<211> LENGTH: 8
<212> TYPE: PRT
<213> ORGANISM: HOMO SAPIENS

<400> SEQUENCE: 101

Phe Gln Asn Ala Leu Leu Val Arg
1               5

<210> SEQ ID NO 102
<211> LENGTH: 9
<212> TYPE: PRT
<213> ORGANISM: HOMO SAPIENS

<400> SEQUENCE: 102

Leu Asp Glu Leu Arg Asp Glu Gly Lys
1               5

<210> SEQ ID NO 103
<211> LENGTH: 9
<212> TYPE: PRT
<213> ORGANISM: HOMO SAPIENS

<400> SEQUENCE: 103

Cys Cys Thr Glu Ser Leu Val Asn Arg
1               5

<210> SEQ ID NO 104
<211> LENGTH: 10
<212> TYPE: PRT
<213> ORGANISM: HOMO SAPIENS

<400> SEQUENCE: 104

Leu Val Asn Glu Val Thr Glu Phe Ala Lys
1               5                   10

<210> SEQ ID NO 105
<211> LENGTH: 18
<212> TYPE: PRT
<213> ORGANISM: HOMO SAPIENS

<400> SEQUENCE: 105

Asp His Val Lys Leu Val Asn Glu Val Thr Glu Phe Ala Lys Thr Cys
1               5                   10                  15

Val Ala

<210> SEQ ID NO 106
<211> LENGTH: 12
<212> TYPE: PRT
```

```
<213> ORGANISM: HOMO SAPIENS

<400> SEQUENCE: 106

Lys Leu Val Asn Glu Val Thr Glu Phe Ala Lys Thr
1               5                   10

<210> SEQ ID NO 107
<211> LENGTH: 22
<212> TYPE: PRT
<213> ORGANISM: HOMO SAPIENS

<400> SEQUENCE: 107

Thr Leu Arg Glu Thr Tyr Gly Glu Met Ala Asp Cys Cys Ala Lys Gln
1               5                   10                  15

Glu Pro Glu Arg Asn Glu
            20

<210> SEQ ID NO 108
<211> LENGTH: 12
<212> TYPE: PRT
<213> ORGANISM: HOMO SAPIENS

<400> SEQUENCE: 108

Glu Met Ala Asp Cys Cys Ala Lys Gln Glu Pro Glu
1               5                   10

<210> SEQ ID NO 109
<211> LENGTH: 21
<212> TYPE: PRT
<213> ORGANISM: HOMO SAPIENS

<400> SEQUENCE: 109

Phe His Asp Asn Glu Glu Thr Phe Leu Lys Lys Tyr Leu Tyr Glu Ile
1               5                   10                  15

Ala Arg Arg His Pro
            20

<210> SEQ ID NO 110
<211> LENGTH: 12
<212> TYPE: PRT
<213> ORGANISM: HOMO SAPIENS

<400> SEQUENCE: 110

Asn Glu Glu Thr Phe Leu Lys Lys Tyr Leu Tyr Glu
1               5                   10

<210> SEQ ID NO 111
<211> LENGTH: 18
<212> TYPE: PRT
<213> ORGANISM: HOMO SAPIENS

<400> SEQUENCE: 111

Leu Leu Pro Lys Leu Asp Glu Leu Arg Asp Glu Gly Lys Ala Ser Ser
1               5                   10                  15

Ala Lys

<210> SEQ ID NO 112
<211> LENGTH: 12
<212> TYPE: PRT
<213> ORGANISM: HOMO SAPIENS

<400> SEQUENCE: 112

Lys Leu Asp Glu Leu Arg Asp Glu Gly Lys Ala Ser
```

1               5                    10

<210> SEQ ID NO 113
<211> LENGTH: 24
<212> TYPE: PRT
<213> ORGANISM: HOMO SAPIENS

<400> SEQUENCE: 113

Gln Asn Cys Glu Leu Phe Glu Gln Leu Gly Glu Tyr Lys Phe Gln Asn
1               5                   10                  15

Ala Leu Leu Val Arg Tyr Thr Lys
            20

<210> SEQ ID NO 114
<211> LENGTH: 11
<212> TYPE: PRT
<213> ORGANISM: HOMO SAPIENS

<400> SEQUENCE: 114

Glu Leu Phe Glu Gln Leu Gly Glu Tyr Lys Phe
1               5                   10

<210> SEQ ID NO 115
<211> LENGTH: 8
<212> TYPE: PRT
<213> ORGANISM: HOMO SAPIENS

<400> SEQUENCE: 115

Lys Tyr Leu Tyr Glu Ile Ala Arg
1               5

<210> SEQ ID NO 116
<211> LENGTH: 15
<212> TYPE: PRT
<213> ORGANISM: HOMO SAPIENS

<400> SEQUENCE: 116

Lys Val Pro Gln Val Ser Thr Pro Thr Leu Val Glu Val Ser Arg
1               5                   10                  15

<210> SEQ ID NO 117
<211> LENGTH: 17
<212> TYPE: PRT
<213> ORGANISM: HOMO SAPIENS

<400> SEQUENCE: 117

Val Phe Asp Glu Phe Lys Pro Leu Val Glu Glu Pro Gln Asn Leu Ile
1               5                   10                  15

Lys

<210> SEQ ID NO 118
<211> LENGTH: 14
<212> TYPE: PRT
<213> ORGANISM: HOMO SAPIENS

<400> SEQUENCE: 118

Val Pro Gln Val Ser Thr Pro Thr Leu Val Glu Val Ser Arg
1               5                   10

<210> SEQ ID NO 119
<211> LENGTH: 16
<212> TYPE: PRT
<213> ORGANISM: HOMO SAPIENS

```
<400> SEQUENCE: 119

Arg Pro Cys Phe Ser Ala Leu Glu Val Asp Glu Thr Tyr Val Pro Lys
1               5                   10                  15

<210> SEQ ID NO 120
<211> LENGTH: 8
<212> TYPE: PRT
<213> ORGANISM: HOMO SAPIENS

<400> SEQUENCE: 120

Phe Gln Asn Ala Leu Leu Val Arg
1               5

<210> SEQ ID NO 121
<211> LENGTH: 9
<212> TYPE: PRT
<213> ORGANISM: HOMO SAPIENS

<400> SEQUENCE: 121

Ser Leu His Thr Leu Phe Gly Asp Lys
1               5

<210> SEQ ID NO 122
<211> LENGTH: 12
<212> TYPE: PRT
<213> ORGANISM: HOMO SAPIENS

<400> SEQUENCE: 122

Leu Lys Glu Cys Cys Glu Lys Pro Leu Leu Glu Lys
1               5                   10

<210> SEQ ID NO 123
<211> LENGTH: 8
<212> TYPE: PRT
<213> ORGANISM: HOMO SAPIENS

<400> SEQUENCE: 123

Leu Cys Thr Val Ala Thr Leu Arg
1               5

<210> SEQ ID NO 124
<211> LENGTH: 7
<212> TYPE: PRT
<213> ORGANISM: HOMO SAPIENS

<400> SEQUENCE: 124

Tyr Leu Tyr Glu Ile Ala Arg
1               5

<210> SEQ ID NO 125
<211> LENGTH: 13
<212> TYPE: PRT
<213> ORGANISM: HOMO SAPIENS

<400> SEQUENCE: 125

Cys Cys Ala Ala Ala Asp Pro His Glu Cys Tyr Ala Lys
1               5                   10

<210> SEQ ID NO 126
<211> LENGTH: 12
<212> TYPE: PRT
<213> ORGANISM: HOMO SAPIENS

<400> SEQUENCE: 126
```

Ala Ala Phe Thr Glu Cys Cys Gln Ala Ala Asp Lys
1               5                   10

<210> SEQ ID NO 127
<211> LENGTH: 9
<212> TYPE: PRT
<213> ORGANISM: HOMO SAPIENS

<400> SEQUENCE: 127

Cys Cys Thr Glu Ser Leu Val Asn Arg
1               5

<210> SEQ ID NO 128
<211> LENGTH: 13
<212> TYPE: PRT
<213> ORGANISM: HOMO SAPIENS

<400> SEQUENCE: 128

Gln Glu Pro Glu Arg Asn Glu Cys Phe Leu Gln His Lys
1               5                   10

<210> SEQ ID NO 129
<211> LENGTH: 12
<212> TYPE: PRT
<213> ORGANISM: HOMO SAPIENS

<400> SEQUENCE: 129

Ala Val Met Asp Asp Phe Ala Ala Phe Val Glu Lys
1               5                   10

<210> SEQ ID NO 130
<211> LENGTH: 8
<212> TYPE: PRT
<213> ORGANISM: HOMO SAPIENS

<400> SEQUENCE: 130

Asn Glu Cys Phe Leu Gln His Lys
1               5

<210> SEQ ID NO 131
<211> LENGTH: 13
<212> TYPE: PRT
<213> ORGANISM: HOMO SAPIENS

<400> SEQUENCE: 131

Gln Asn Cys Glu Leu Phe Glu Gln Leu Gly Glu Tyr Lys
1               5                   10

<210> SEQ ID NO 132
<211> LENGTH: 13
<212> TYPE: PRT
<213> ORGANISM: HOMO SAPIENS

<400> SEQUENCE: 132

Gln Glu Pro Glu Arg Asn Glu Cys Phe Leu Gln His Lys
1               5                   10

<210> SEQ ID NO 133
<211> LENGTH: 17
<212> TYPE: PRT
<213> ORGANISM: HOMO SAPIENS

<400> SEQUENCE: 133

Val His Thr Glu Cys Cys His Gly Asp Leu Leu Glu Cys Ala Asp Asp
1               5                   10                  15

Arg

<210> SEQ ID NO 134
<211> LENGTH: 10
<212> TYPE: PRT
<213> ORGANISM: HOMO SAPIENS

<400> SEQUENCE: 134

Phe Lys Asp Leu Gly Glu Glu Asn Phe Lys
1               5                   10

<210> SEQ ID NO 135
<211> LENGTH: 12
<212> TYPE: PRT
<213> ORGANISM: HOMO SAPIENS

<400> SEQUENCE: 135

Tyr Ile Cys Glu Asn Gln Asp Ser Ile Ser Ser Lys
1               5                   10

<210> SEQ ID NO 136
<211> LENGTH: 9
<212> TYPE: PRT
<213> ORGANISM: HOMO SAPIENS

<400> SEQUENCE: 136

Leu Asp Glu Leu Arg Asp Glu Gly Lys
1               5

<210> SEQ ID NO 137
<211> LENGTH: 8
<212> TYPE: PRT
<213> ORGANISM: HOMO SAPIENS

<400> SEQUENCE: 137

Asp Asp Asn Pro Asn Leu Pro Arg
1               5

<210> SEQ ID NO 138
<211> LENGTH: 10
<212> TYPE: PRT
<213> ORGANISM: HOMO SAPIENS

<400> SEQUENCE: 138

Leu Val Asn Glu Val Thr Glu Phe Ala Lys
1               5                   10

<210> SEQ ID NO 139
<211> LENGTH: 12
<212> TYPE: PRT
<213> ORGANISM: HOMO SAPIENS

<400> SEQUENCE: 139

Glu Thr Tyr Gly Glu Met Ala Asp Cys Cys Ala Lys
1               5                   10

<210> SEQ ID NO 140
<211> LENGTH: 14
<212> TYPE: PRT
<213> ORGANISM: HOMO SAPIENS

<400> SEQUENCE: 140

Tyr Lys Ala Ala Phe Thr Glu Cys Cys Gln Ala Ala Asp Lys
1               5                   10

<210> SEQ ID NO 141
<211> LENGTH: 8
<212> TYPE: PRT
<213> ORGANISM: HOMO SAPIENS

<400> SEQUENCE: 141

Lys Tyr Leu Tyr Glu Ile Ala Arg
 1               5

<210> SEQ ID NO 142
<211> LENGTH: 15
<212> TYPE: PRT
<213> ORGANISM: HOMO SAPIENS

<400> SEQUENCE: 142

Lys Val Pro Gln Val Ser Thr Pro Thr Leu Val Glu Val Ser Arg
 1               5                  10                  15

<210> SEQ ID NO 143
<211> LENGTH: 16
<212> TYPE: PRT
<213> ORGANISM: HOMO SAPIENS

<400> SEQUENCE: 143

Val Phe Asp Glu Phe Lys Pro Leu Val Glu Glu Pro Gln Asn Leu Ile
 1               5                  10                  15

<210> SEQ ID NO 144
<211> LENGTH: 13
<212> TYPE: PRT
<213> ORGANISM: HOMO SAPIENS

<400> SEQUENCE: 144

Gln Asn Cys Glu Leu Phe Glu Gln Leu Gly Glu Tyr Lys
 1               5                  10

<210> SEQ ID NO 145
<211> LENGTH: 23
<212> TYPE: PRT
<213> ORGANISM: HOMO SAPIENS

<400> SEQUENCE: 145

Asn Glu Glu Thr Phe Leu Lys Lys Tyr Leu Tyr Glu Ile Ala Arg Arg
 1               5                  10                  15

His Pro Tyr Phe Tyr Ala Pro
            20

<210> SEQ ID NO 146
<211> LENGTH: 15
<212> TYPE: PRT
<213> ORGANISM: HOMO SAPIENS

<400> SEQUENCE: 146

Lys Val Pro Gln Val Ser Thr Pro Thr Leu Val Glu Val Ser Arg
 1               5                  10                  15

<210> SEQ ID NO 147
<211> LENGTH: 18
<212> TYPE: PRT
<213> ORGANISM: HOMO SAPIENS

<400> SEQUENCE: 147

Glu Leu Phe Glu Gln Leu Gly Glu Tyr Lys Phe Gln Asn Ala Leu Leu

```
                1               5                  10                  15

Val Arg

<210> SEQ ID NO 148
<211> LENGTH: 12
<212> TYPE: PRT
<213> ORGANISM: HOMO SAPIENS

<400> SEQUENCE: 148

Asn Glu Glu Thr Phe Leu Lys Lys Tyr Leu Tyr Glu
  1               5                  10

<210> SEQ ID NO 149
<211> LENGTH: 11
<212> TYPE: PRT
<213> ORGANISM: HOMO SAPIENS

<400> SEQUENCE: 149

Glu Leu Phe Glu Gln Leu Gly Glu Tyr Lys Phe
  1               5                  10

<210> SEQ ID NO 150
<211> LENGTH: 18
<212> TYPE: PRT
<213> ORGANISM: HOMO SAPIENS

<400> SEQUENCE: 150

Asp His Val Lys Leu Val Asn Glu Val Thr Glu Phe Ala Lys Thr Cys
  1               5                  10                  15

Val Ala

<210> SEQ ID NO 151
<211> LENGTH: 24
<212> TYPE: PRT
<213> ORGANISM: HOMO SAPIENS

<400> SEQUENCE: 151

Asp Asp Lys Glu Thr Cys Phe Ala Glu Glu Gly Lys Lys Leu Val Ala
  1               5                  10                  15

Ala Ser Gln Ala Ala Leu Gly Leu
            20

<210> SEQ ID NO 152
<211> LENGTH: 23
<212> TYPE: PRT
<213> ORGANISM: HOMO SAPIENS

<400> SEQUENCE: 152

Asp Arg Val Thr Lys Cys Cys Thr Glu Ser Leu Val Asn Arg Arg Pro
  1               5                  10                  15

Cys Phe Ser Ala Leu Glu Val
            20

<210> SEQ ID NO 153
<211> LENGTH: 17
<212> TYPE: PRT
<213> ORGANISM: HOMO SAPIENS

<400> SEQUENCE: 153

Asp Glu Thr Tyr Val Pro Lys Glu Phe Asn Ala Glu Thr Phe Thr His
  1               5                  10                  15

Ala
```

```
<210> SEQ ID NO 154
<211> LENGTH: 27
<212> TYPE: PRT
<213> ORGANISM: HOMO SAPIENS

<400> SEQUENCE: 154

Asp Ser Ile Ser Ser Lys Leu Lys Glu Cys Cys Glu Lys Pro Leu Leu
1               5                   10                  15

Glu Lys Ser His Cys Ile Ala Glu Val Glu Asn
            20                  25

<210> SEQ ID NO 155
<211> LENGTH: 16
<212> TYPE: PRT
<213> ORGANISM: HOMO SAPIENS

<400> SEQUENCE: 155

Asp Lys Leu Cys Thr Val Ala Thr Leu Arg Glu Thr Tyr Gly Glu Met
1               5                   10                  15

<210> SEQ ID NO 156
<211> LENGTH: 34
<212> TYPE: PRT
<213> ORGANISM: HOMO SAPIENS

<400> SEQUENCE: 156

Tyr Ser Val Val Leu Leu Leu Arg Leu Ala Lys Thr Tyr Glu Thr Thr
1               5                   10                  15

Leu Glu Lys Cys Cys Ala Ala Ala Asp Pro His Glu Cys Tyr Ala Lys
            20                  25                  30

Val Phe

<210> SEQ ID NO 157
<211> LENGTH: 34
<212> TYPE: PRT
<213> ORGANISM: HOMO SAPIENS

<400> SEQUENCE: 157

Lys Leu Cys Thr Val Ala Thr Leu Arg Glu Thr Tyr Gly Glu Met Ala
1               5                   10                  15

Asp Cys Cys Ala Lys Gln Glu Pro Glu Arg Asn Glu Cys Phe Leu Glu
            20                  25                  30

His Lys

<210> SEQ ID NO 158
<211> LENGTH: 36
<212> TYPE: PRT
<213> ORGANISM: HOMO SAPIENS

<400> SEQUENCE: 158

Ile Cys Thr Leu Ser Glu Lys Glu Arg Gln Ile Lys Lys Gln Thr Ala
1               5                   10                  15

Leu Val Glu Leu Val Lys His Lys Pro Lys Ala Thr Lys Glu Gln Leu
            20                  25                  30

Lys Ala Val Met
        35

<210> SEQ ID NO 159
<211> LENGTH: 36
<212> TYPE: PRT
```

```
<213> ORGANISM: HOMO SAPIENS

<400> SEQUENCE: 159

Leu Ala Lys Tyr Ile Cys Glu Asn Gln Asp Ser Ile Ser Ser Lys Leu
1               5                   10                  15
Lys Glu Cys Cys Glu Lys Pro Leu Leu Glu Lys Ser His Cys Ile Ala
            20                  25                  30
Glu Val Glu Asn
        35

<210> SEQ ID NO 160
<211> LENGTH: 40
<212> TYPE: PRT
<213> ORGANISM: HOMO SAPIENS

<400> SEQUENCE: 160

Val Phe Leu Gly Met Phe Leu Tyr Glu Tyr Ala Arg Arg His Pro Asp
1               5                   10                  15
Tyr Ser Val Val Leu Leu Leu Arg Leu Ala Lys Thr Tyr Glu Thr Thr
            20                  25                  30
Leu Glu Lys Cys Cys Ala Ala Ala
        35                  40

<210> SEQ ID NO 161
<211> LENGTH: 42
<212> TYPE: PRT
<213> ORGANISM: HOMO SAPIENS

<400> SEQUENCE: 161

Leu Gly Glu Glu Asn Phe Lys Ala Leu Val Leu Ile Ala Phe Ala Gln
1               5                   10                  15
Tyr Leu Gln Gln Cys Pro Phe Glu Asp His Val Lys Leu Val Asn Glu
            20                  25                  30
Val Thr Glu Phe Ala Lys Thr Cys Val Ala
        35                  40

<210> SEQ ID NO 162
<211> LENGTH: 40
<212> TYPE: PRT
<213> ORGANISM: HOMO SAPIENS

<400> SEQUENCE: 162

Arg Val Thr Lys Cys Cys Thr Glu Ser Leu Val Asn Arg Arg Pro Cys
1               5                   10                  15
Phe Ser Ala Leu Glu Val Asp Glu Thr Tyr Val Pro Lys Glu Phe Asn
            20                  25                  30
Ala Glu Thr Phe Thr Phe His Ala
        35                  40

<210> SEQ ID NO 163
<211> LENGTH: 42
<212> TYPE: PRT
<213> ORGANISM: HOMO SAPIENS

<400> SEQUENCE: 163

Tyr Leu Ser Val Val Leu Asn Gln Leu Cys Val Leu His Glu Lys Thr
1               5                   10                  15
Pro Val Ser Asp Arg Val Thr Lys Cys Cys Thr Glu Ser Leu Val Asn
            20                  25                  30
Arg Arg Pro Cys Phe Ser Ala Leu Glu Val
```

35                40

<210> SEQ ID NO 164
<211> LENGTH: 32
<212> TYPE: PRT
<213> ORGANISM: HOMO SAPIENS

<400> SEQUENCE: 164

Pro His Glu Cys Tyr Ala Lys Val Phe Asp Glu Phe Lys Pro Leu Val
1               5                   10                  15

Glu Glu Pro Gln Asn Leu Ile Lys Gln Asn Cys Glu Leu Phe Glu Gln
            20                  25                  30

<210> SEQ ID NO 165
<211> LENGTH: 31
<212> TYPE: PRT
<213> ORGANISM: HOMO SAPIENS

<400> SEQUENCE: 165

Pro His Glu Cys Tyr Ala Lys Val Phe Asp Glu Phe Lys Pro Leu Val
1               5                   10                  15

Glu Glu Pro Gln Asn Leu Ile Lys Gln Asn Cys Glu Leu Phe Glu
            20                  25                  30

<210> SEQ ID NO 166
<211> LENGTH: 30
<212> TYPE: PRT
<213> ORGANISM: HOMO SAPIENS

<400> SEQUENCE: 166

Pro His Glu Cys Tyr Ala Lys Val Phe Asp Glu Phe Lys Pro Leu Val
1               5                   10                  15

Glu Glu Pro Gln Asn Leu Ile Lys Gln Asn Cys Glu Leu Phe
            20                  25                  30

<210> SEQ ID NO 167
<211> LENGTH: 29
<212> TYPE: PRT
<213> ORGANISM: HOMO SAPIENS

<400> SEQUENCE: 167

Pro His Glu Cys Tyr Ala Lys Val Phe Asp Glu Phe Lys Pro Leu Val
1               5                   10                  15

Glu Glu Pro Gln Asn Leu Ile Lys Gln Asn Cys Glu Leu
            20                  25

<210> SEQ ID NO 168
<211> LENGTH: 28
<212> TYPE: PRT
<213> ORGANISM: HOMO SAPIENS

<400> SEQUENCE: 168

Pro His Glu Cys Tyr Ala Lys Val Phe Asp Glu Phe Lys Pro Leu Val
1               5                   10                  15

Glu Glu Pro Gln Asn Leu Ile Lys Gln Asn Cys Glu
            20                  25

<210> SEQ ID NO 169
<211> LENGTH: 27
<212> TYPE: PRT
<213> ORGANISM: HOMO SAPIENS

<400> SEQUENCE: 169

```
Pro His Glu Cys Tyr Ala Lys Val Phe Asp Glu Phe Lys Pro Leu Val
  1               5                   10                  15

Glu Glu Pro Gln Asn Leu Ile Lys Gln Asn Cys
            20                  25

<210> SEQ ID NO 170
<211> LENGTH: 26
<212> TYPE: PRT
<213> ORGANISM: HOMO SAPIENS

<400> SEQUENCE: 170

Pro His Glu Cys Tyr Ala Lys Val Phe Asp Glu Phe Lys Pro Leu Val
  1               5                   10                  15

Glu Glu Pro Gln Asn Leu Ile Lys Gln Asn
            20                  25

<210> SEQ ID NO 171
<211> LENGTH: 25
<212> TYPE: PRT
<213> ORGANISM: HOMO SAPIENS

<400> SEQUENCE: 171

Pro His Glu Cys Tyr Ala Lys Val Phe Asp Glu Phe Lys Pro Leu Val
  1               5                   10                  15

Glu Glu Pro Gln Asn Leu Ile Lys Gln
            20                  25

<210> SEQ ID NO 172
<211> LENGTH: 23
<212> TYPE: PRT
<213> ORGANISM: HOMO SAPIENS

<400> SEQUENCE: 172

His Glu Cys Tyr Ala Lys Val Phe Asp Glu Phe Lys Pro Leu Val Glu
  1               5                   10                  15

Glu Pro Gln Asn Leu Ile Lys
            20

<210> SEQ ID NO 173
<211> LENGTH: 22
<212> TYPE: PRT
<213> ORGANISM: HOMO SAPIENS

<400> SEQUENCE: 173

Glu Cys Tyr Ala Lys Val Phe Asp Glu Phe Lys Pro Leu Val Glu Glu
  1               5                   10                  15

Pro Gln Asn Leu Ile Lys
            20

<210> SEQ ID NO 174
<211> LENGTH: 21
<212> TYPE: PRT
<213> ORGANISM: HOMO SAPIENS

<400> SEQUENCE: 174

Cys Tyr Ala Lys Val Phe Asp Glu Phe Lys Pro Leu Val Glu Glu Pro
  1               5                   10                  15

Gln Asn Leu Ile Lys
            20

<210> SEQ ID NO 175
```

<211> LENGTH: 20
<212> TYPE: PRT
<213> ORGANISM: HOMO SAPIENS

<400> SEQUENCE: 175

Tyr Ala Lys Val Phe Asp Glu Phe Lys Pro Leu Val Glu Glu Pro Gln
1               5                   10                  15

Asn Leu Ile Lys
            20

<210> SEQ ID NO 176
<211> LENGTH: 19
<212> TYPE: PRT
<213> ORGANISM: HOMO SAPIENS

<400> SEQUENCE: 176

Ala Lys Val Phe Asp Glu Phe Lys Pro Leu Val Glu Glu Pro Gln Asn
1               5                   10                  15

Leu Ile Lys

<210> SEQ ID NO 177
<211> LENGTH: 18
<212> TYPE: PRT
<213> ORGANISM: HOMO SAPIENS

<400> SEQUENCE: 177

Lys Val Phe Asp Glu Phe Lys Pro Leu Val Glu Glu Pro Gln Asn Leu
1               5                   10                  15

Ile Lys

<210> SEQ ID NO 178
<211> LENGTH: 24
<212> TYPE: PRT
<213> ORGANISM: HOMO SAPIENS

<400> SEQUENCE: 178

Pro His Glu Cys Tyr Ala Lys Val Phe Asp Glu Phe Lys Pro Leu Val
1               5                   10                  15

Glu Glu Pro Gln Asn Leu Ile Lys
            20

<210> SEQ ID NO 179
<211> LENGTH: 30
<212> TYPE: PRT
<213> ORGANISM: HOMO SAPIENS

<400> SEQUENCE: 179

His Glu Cys Tyr Ala Lys Val Phe Asp Glu Phe Lys Pro Leu Val Glu
1               5                   10                  15

Glu Pro Gln Asn Leu Ile Lys Gln Asn Cys Glu Leu Phe Glu
            20                  25                  30

<210> SEQ ID NO 180
<211> LENGTH: 28
<212> TYPE: PRT
<213> ORGANISM: HOMO SAPIENS

<400> SEQUENCE: 180

Glu Cys Tyr Ala Lys Val Phe Asp Glu Phe Lys Pro Leu Val Glu Glu
1               5                   10                  15

Pro Gln Asn Leu Ile Lys Gln Asn Cys Glu Leu Phe
            20                  25

```
<210> SEQ ID NO 181
<211> LENGTH: 27
<212> TYPE: PRT
<213> ORGANISM: HOMO SAPIENS

<400> SEQUENCE: 181

Glu Cys Tyr Ala Lys Val Phe Asp Glu Phe Lys Pro Leu Val Glu Glu
1               5                   10                  15

Pro Gln Asn Leu Ile Lys Gln Asn Cys Glu Leu
            20                  25

<210> SEQ ID NO 182
<211> LENGTH: 26
<212> TYPE: PRT
<213> ORGANISM: HOMO SAPIENS

<400> SEQUENCE: 182

Cys Tyr Ala Lys Val Phe Asp Glu Phe Lys Pro Leu Val Glu Glu Pro
1               5                   10                  15

Gln Asn Leu Ile Lys Gln Asn Cys Glu Leu
            20                  25

<210> SEQ ID NO 183
<211> LENGTH: 24
<212> TYPE: PRT
<213> ORGANISM: HOMO SAPIENS

<400> SEQUENCE: 183

Tyr Ala Lys Val Phe Asp Glu Phe Lys Pro Leu Val Glu Glu Pro Gln
1               5                   10                  15

Asn Leu Ile Lys Gln Asn Cys Glu
            20

<210> SEQ ID NO 184
<211> LENGTH: 23
<212> TYPE: PRT
<213> ORGANISM: HOMO SAPIENS

<400> SEQUENCE: 184

Tyr Ala Lys Val Phe Asp Glu Phe Lys Pro Leu Val Glu Glu Pro Gln
1               5                   10                  15

Asn Leu Ile Lys Gln Asn Cys
            20

<210> SEQ ID NO 185
<211> LENGTH: 17
<212> TYPE: PRT
<213> ORGANISM: HOMO SAPIENS

<400> SEQUENCE: 185

Pro His Glu Cys Tyr Ala Lys Val Phe Asp Glu Phe Lys Pro Leu Val
1               5                   10                  15

Glu

<210> SEQ ID NO 186
<211> LENGTH: 16
<212> TYPE: PRT
<213> ORGANISM: HOMO SAPIENS

<400> SEQUENCE: 186

His Glu Cys Tyr Ala Lys Val Phe Asp Glu Phe Lys Pro Leu Val Glu
```

```
1               5                   10                  15
```

<210> SEQ ID NO 187
<211> LENGTH: 15
<212> TYPE: PRT
<213> ORGANISM: HOMO SAPIENS

<400> SEQUENCE: 187

```
Glu Cys Tyr Ala Lys Val Phe Asp Glu Phe Lys Pro Leu Val Glu
1               5                   10                  15
```

<210> SEQ ID NO 188
<211> LENGTH: 14
<212> TYPE: PRT
<213> ORGANISM: HOMO SAPIENS

<400> SEQUENCE: 188

```
Cys Tyr Ala Lys Val Phe Asp Glu Phe Lys Pro Leu Val Glu
1               5                   10
```

<210> SEQ ID NO 189
<211> LENGTH: 13
<212> TYPE: PRT
<213> ORGANISM: HOMO SAPIENS

<400> SEQUENCE: 189

```
Tyr Ala Lys Val Phe Asp Glu Phe Lys Pro Leu Val Glu
1               5                   10
```

<210> SEQ ID NO 190
<211> LENGTH: 12
<212> TYPE: PRT
<213> ORGANISM: HOMO SAPIENS

<400> SEQUENCE: 190

```
Ala Lys Val Phe Asp Glu Phe Lys Pro Leu Val Glu
1               5                   10
```

<210> SEQ ID NO 191
<211> LENGTH: 11
<212> TYPE: PRT
<213> ORGANISM: HOMO SAPIENS

<400> SEQUENCE: 191

```
Lys Val Phe Asp Glu Phe Lys Pro Leu Val Glu
1               5                   10
```

<210> SEQ ID NO 192
<211> LENGTH: 21
<212> TYPE: PRT
<213> ORGANISM: HOMO SAPIENS

<400> SEQUENCE: 192

```
Ala Lys Val Phe Asp Glu Phe Lys Pro Leu Val Glu Glu Pro Gln Asn
1               5                   10                  15

Leu Ile Lys Gln Asn
            20
```

<210> SEQ ID NO 193
<211> LENGTH: 19
<212> TYPE: PRT
<213> ORGANISM: HOMO SAPIENS

<400> SEQUENCE: 193

```
Lys Val Phe Asp Glu Phe Lys Pro Leu Val Glu Glu Pro Gln Asn Leu
1               5                   10                  15
Ile Lys Gln

<210> SEQ ID NO 194
<211> LENGTH: 7
<212> TYPE: PRT
<213> ORGANISM: HOMO SAPIENS

<400> SEQUENCE: 194

Glu Leu Lys Pro Leu Glu Glu
1               5

<210> SEQ ID NO 195
<211> LENGTH: 31
<212> TYPE: PRT
<213> ORGANISM: HOMO SAPIENS

<400> SEQUENCE: 195

Ser Ile Ser Ser Lys Leu Lys Glu Cys Cys Glu Lys Pro Leu Leu Glu
1               5                   10                  15
Lys Ser His Cys Ile Ala Glu Val Glu Asn Asp Glu Met Pro Ala
                20                  25                  30
```